United States Patent
Skelly et al.

(10) Patent No.: US 11,798,661 B2
(45) Date of Patent: *Oct. 24, 2023

(54) METHODS FOR LOWERING BLOOD PRESSURE WITH A DIHYDROPYRIDINE-TYPE CALCIUM CHANNEL BLOCKER PHARMACEUTICAL COMPOSITION

(71) Applicant: AstraZeneca UK Limited, Cambridge (GB)

(72) Inventors: Richard L. Skelly, Flourtown, PA (US); Judy Firor, Landenberg, PA (US)

(73) Assignee: ASTRAZENECA UK LIMITED, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/862,342

(22) Filed: Jul. 11, 2022

(65) Prior Publication Data

US 2023/0046548 A1 Feb. 16, 2023

Related U.S. Application Data

(63) Continuation of application No. 16/440,319, filed on Jun. 13, 2019, now Pat. No. 11,417,416.

(Continued)

(51) Int. Cl.
*G16H 10/20* (2018.01)
*G16H 10/40* (2018.01)
(Continued)

(52) U.S. Cl.
CPC ............ *G16H 10/20* (2018.01); *G16H 10/40* (2018.01); *G16H 10/60* (2018.01); *G16H 20/10* (2018.01);

(Continued)

(58) Field of Classification Search
None
See application file for complete search history.

(56) References Cited

U.S. PATENT DOCUMENTS

| 4,572,909 A | 2/1986 | Campbell et al. |
| 5,519,012 A | 5/1996 | Fercej-Temeljotov et al. |

(Continued)

FOREIGN PATENT DOCUMENTS

WO WO 2010/041052 A1 4/2010

OTHER PUBLICATIONS

Chang J, Lizer A, Patel I, Bhatia D, Tan X, Balkrishnan R. Prescription to over-the-counter switches in the United States. J Res Pharm Pract, . Jul.-Sep. 2016;5 (3):149-54. (Year: 2016).*

(Continued)

*Primary Examiner* — Rachel L. Porter
(74) *Attorney, Agent, or Firm* — Brett A. Lovejoy; Andrew J. Antczak; Morgan, Lewis & Bockius LLP

(57) ABSTRACT

A method is provided for lowering blood pressure in a subject in need thereof by administering a dihydropyridine-type calcium channel blocker pharmaceutical composition to a subject qualified for over-the-counter access to the dihydropyridine-type calcium channel blocker pharmaceutical composition. In some embodiments, the dihydropyridine-type calcium channel blocker pharmaceutical composition includes isradipine, nifedipine, or nisoldipine. In some embodiments, the dihydropyridine-type calcium channel blocker pharmaceutical composition includes 3-O-ethyl 5-O-methyl 2-(2-aminoethoxymethyl)-4-(2-chlorophenyl)-6-methyl-1,4-dihydropyridine-3,5-dicarboxylate or a pharmaceutically acceptable salt thereof.

19 Claims, 21 Drawing Sheets

Related U.S. Application Data

(60) Provisional application No. 62/685,209, filed on Jun. 14, 2018.

(51) Int. Cl.
    *G16H 10/60* (2018.01)
    *G16H 70/40* (2018.01)
    *G16H 20/10* (2018.01)
    *G16H 15/00* (2018.01)
    *A61K 31/4422* (2006.01)

(52) U.S. Cl.
    CPC .......... *G16H 70/40* (2018.01); *A61K 31/4422* (2013.01); *G16H 15/00* (2018.01)

(56) References Cited

U.S. PATENT DOCUMENTS

| | | | |
|---|---|---|---|
| 7,493,264 | B1 | 2/2009 | Kelly et al. |
| 10,325,678 | B2* | 6/2019 | Blasetto ............... G16H 70/20 |
| 2005/0108053 | A1 | 5/2005 | Jones |
| 2009/0125324 | A1 | 5/2009 | Keravich et al. |
| 2011/0166876 | A1 | 7/2011 | Chapman |
| 2011/0178812 | A1 | 7/2011 | Lindsay |
| 2018/0125828 | A1 | 5/2018 | Banait et al. |
| 2018/0197622 | A1 | 7/2018 | Blasetto et al. |
| 2020/0160958 | A1* | 5/2020 | Huser ................ G16H 50/20 |

OTHER PUBLICATIONS

International Search Report and Written Opinion for International Patent Application No. PCT/US2019/036977, dated Oct. 21, 2019, 29 pages.

Fares et al., "Amlodipine in hypertension: a first-line agent with efficacy for improving blood pressure and patient outcomes", Open Heart, vol. 3, No. 2, Sep. 28, 2016, p. e000473.

Hermida et al., Chronotherapy With Nifedipine GITS in Hypertensive Patients: Improved Efficacy and Safety With Bedtime Dosing:, American Journal of Hypertension, vol. 21, No. 8, Jul. 3, 2008, pp. 948-954.

Goff et al., "2013 ACC/AHA Guideline on the Assessment of Cardiovascular Risk A Report of the American College of Cardiology/American Heart Association Task Force on Practice Guidelines", Journal of the American College of Cardiology, Elsevier, New York, NY, vol. 63, No. 25, Nov. 12, 2013.

Perk et al., "European Guidelines on cardiovascular disease prevention in clinical practice (version 2012): The Fifth Joint Task Force of the European Society of Cardiovascular Disease Prevention in Clinical Practice", European Heart Journal, vol. 33, No. 13, May 3, 2021.

Ramkumar, S. et al., Acta Cardiol. Sin., 32(6):631-39 (2016).

Barlas S. FDA Considers a New Paradigm for Over-the-Counter Medications: More Power—but More Burdens—for Pharmacists and Pharmacies. P T. May 2012;37(5):300-5. PubMed PMID: 22876088; PubMed Central PMCID: PMC3411219.

Crestor, Full Prescribing Information, 2012, AstraZeneca Pharmaceuticals LP.

Dyer O., "FDA Rejects sale of over the counter Statins", BMJ, Jan. 22, 2005; 330(7484):164.

May 9, 2013, power point presentations from the Engelberg Center for Health Care Reform.

Pfizer Wants Atorvastatin Available Over the Counter—Medscape—Aug. 4, 2011, downloaded from the Internet Nov. 30, 2018.

PR Newswire Association, "Americans Should Pay More Attention to Over-the-Counter (OTC) medicine Labels According to New Survey", Oct. 15, 2015 (citing McNeil Consumer Healthcare research).

Norvasc (amlodipine besylate) Tablets Prescribing Information, (Pfizer Labs) May 2011, [online], [retrieved on Feb. 28, 2021], Retrieved from the Internet: <URL: https://www.accessdata.fda.gov/drugsatfda_docs/label/2011/019787s047lbl.pdf>.

Dynacirc (isradipine) Capsules Prescribing Information (Sandoz Pharmaceuticals Corporation) Nov. 28, 1990, [online], [retrieved on Feb. 28, 2021] Retrieved from the Internet: <URL: https://www.accessdata.fda.gov/drugsatfda_docs/nda/pre96/19-546_Isradipine_Approv.pdf >.

Procardia XL (nifedipine) Tablets Prescribing Information (Pfizer Labs), Feb. 2010, [online], [retrieved on Feb. 28, 2021] Retrieved from the Internet: <URL: https://www.accessdata.fda.gov/drugsatfda_docs/label/2010/019684s023lbl.pdf >.

Sular (nisoldipine) Tablets Prescribing Information (Covis Pharma) 2016, [online], [retrieved on Feb. 28, 2021] Retrieved from the Internet: <URL: https://www.accessdata.fda.gov/drugsatfda_docs/label/2017/020356s027lbl.pdf >.

EMA Amlodipine Label: Amlodipine/Valsartan Mylan Tablets—Summary of Product Characteristics; European Medicines Agency (EMA) https://www.ema.europa.eu/en/medicines/human/EPAR/amlodipine-valsartan-mylan#product-information-section (53 pgs) (May 7, 2021).

Norvasc (amlodipine besylate) Drug Facts Label: https://www.accessdata.fda.gov/drugsatfda_docs/label/2011/019787s047lbl_(12 pgs) (May 2011).

Both et al., Analysis of licensed over-the-counter (OTC) antibiotics in the European Union and Norway. Euro Surveill (2015).

Chang et al., Prescription to over-the-counter switches in the United States. Journal of Research in Pharmacy Practice. (2016).

Ferris et al., Over-the-Counter Antifungal Drug Misuse Associated With Patient-Diagnosed Vulvovaginal Candidiasis. Antifungal Drug Misuse. Obstetrics & Gynecology. vol. 99, No. 3, (2002) The American College of Obstetricians and Gynecologists.

Stomberg et al., Utilization effects of Rx-OTC switches and implications for future switches. Health. vol. 5, No. 10, 1667-1680 (2013).

Yuen and Chong, Rx-to-OTC Switch—An Overview and its Implications to Public Health. Pharmacy Education & Practice. vol. 25, No. 4 (2018).

* cited by examiner (402) A computer system for qualifying a human subject for over-the-counter delivery of a dihydropyridine-type calcium channel blocker pharmaceutical composition for lowering blood pressure. The computer system comprises one or more processors and a memory. The memory comprises non-transitory instructions which, when executed by the one or more processor, perform a method.

(404) The dihydropyridine-type calcium channel blocker pharmaceutical composition has a structure of structure (I).

(406) The dihydropyridine-type calcium channel blocker pharmaceutical composition includes amlodipine or a pharmaceutically acceptable salt thereof.

(408) The dihydropyridine-type calcium channel blocker pharmaceutical composition includes amlodipine besylate.

(410) The dihydropyridine-type calcium channel blocker pharmaceutical composition includes a composition selected from the group consisting of felodipine, isradipine, nifedipine, and nisoldipine.

(412) The lowering blood pressure is to treat or prevent heart disease.

(414) Conduct a first survey of the subject thereby obtaining a first plurality of survey results.

(416) The first plurality of survey results comprise whether the subject is one of (i) pregnant, (ii) breastfeeding, or (iii) planning to become pregnant, whether the subject is taking a dihydropyridine-type calcium channel blocker, a systolic blood pressure of the subject, a diastolic blood pressure of the subject, whether the subject has ever had an atherosclerotic cardiovascular event or had a heart procedure, a gender of the subject, an age of the subject, a race of the subject, whether the subject is taking any blood pressure medications, a diabetes status of the subject, a smoking status of the subject, a total cholesterol level of the subject, a high-density lipoprotein (HDL) cholesterol level of the subject, whether the subject has ever had a liver problem, and whether the subject is taking a medication that interacts with the dihydropyridine-type calcium channel blocker pharmaceutical composition.

Fig. 4A

*(418)* Run all or a portion of the first plurality of survey results against a first plurality of filters of a first category class. When a respective filter in the first plurality of filters is fired, the subject is deemed not qualified for delivery of the dihydropyridine-type calcium channel blocker pharmaceutical composition and the method is terminated without delivery of the dihydropyridine-type calcium channel blocker pharmaceutical composition to the subject.

*(420)* The first plurality of filters comprises a first pregnancy filter that is fired at least when the first plurality of survey results indicates that the subject is pregnant or the subject is breastfeeding.

*(422)* The first pregnancy filter is also fired when the first plurality of survey results indicates that the subject is planning to become pregnant.

*(424)* The first plurality of filters comprises a dihydropyridine medication filter that is fired at least when the first plurality of survey results indicates that the subject is taking a dihydropyridine-type calcium channel blocker.

*(426)* The dihydropyridine medication filter is fired when the first plurality of survey results indicates that the subject is taking amlodipine, felodipine, isradipine, or nifedipine.

*(428)* The first plurality of filters comprises a first blood pressure filter that is fired at least when the first plurality of survey results indicates the subject has normal blood pressure or the subject has severe hypertension.

*(430)* The first blood pressure filter is fired when the first plurality of survey results indicates that the systolic blood pressure of the subject is greater than a ceiling systolic pressure, the diastolic blood pressure of the subject is greater than a ceiling diastolic pressure, or the systolic blood pressure of the subject is less than a baseline systolic pressure and the diastolic blood pressure of the subject is less than a baseline diastolic pressure.

*(432)* The ceiling systolic pressure is 139 mm Hg, the ceiling diastolic pressure is 89 mm Hg, the baseline systolic pressure is 130 mm Hg, and the baseline diastolic pressure is 80 mm Hg.

(434) When the first plurality of survey results indicate that the subject has elevated blood pressure but is not hypertensive, fire the first blood pressure filter, and transmit, to the subject, advice to manage their blood pressure by eating healthy and exercising.

(436) When the first plurality of survey results indicate that the subject has stage two hypertension, fire the first blood pressure filter, and transmit, to the subject, advice to visit a doctor to discuss taking a prescription-strength blood pressure medication.

(438) When the first plurality of survey results indicate that the subject is in hypertension crisis, fire the first blood pressure filter, and transmit, to the subject, advice to seek emergency medical attention.

(440) The first plurality of filters comprises an age filter.

(442) The age filter is fired when the first plurality of survey results indicates that the subject is less than eighteen years old.

(444) The first plurality of filters comprises a pooled cohort equation filter that incorporates the gender of the subject, the age of the subject, the race of the subject, the blood pressure medication status of the subject, the diabetes status of the subject, the smoking status of the subject, the total cholesterol level of the subject, and the HDL cholesterol level of the subject to derive a risk for atherosclerotic cardiovascular disease.

(446) The pooled cohort equation filter is fired when the first plurality of survey results indicates the subject is younger than forty years old, or the subject has a 10-year risk for atherosclerotic cardiovascular disease, as determined using the pooled cohort equation, that is less than 10%.

(448) The pooled cohort equation is implemented as a multivariable Cox proportional hazard regression.

(450) When the first plurality of survey results indicate that the subject is at least 80 years old, that the subject has had an atherosclerotic cardiovascular event, or that the subject has had a heart procedure, bypass the pooled cohort equation filter.

*(452)* The first plurality of survey results further comprises whether the subject is allergic to the dihydropyridine-type calcium channel blocker pharmaceutical composition, and the first plurality of filters includes an adverse reaction filter that is fired when the first plurality of survey results indicates that the subject is allergic to the dihydropyridine-type calcium channel blocker pharmaceutical composition.

*(454)* Run all or a portion of the first plurality of survey results against a second plurality of filters of a second category class. When a respective filter in the second plurality of filters is fired, the subject is provided with a warning corresponding to the respective filter.

*(456)* The second plurality of filters comprises a first liver disease filter that is fired at least when the first plurality of survey results indicates that the subject has had a liver problem.

*(458)* The second plurality of filters comprises a first drug interaction filter that is fired at least when the first plurality of survey results indicates that the subject is taking a medication that interacts with the dihydropyridine-type calcium channel blocker pharmaceutical composition.

*(460)* The drug interaction filter is fired when the first plurality of survey results indicates that the subject is taking a medication selected from the group consisting of simvastatin, cyclosporine, tacrolimus, sildenafil, and a CYP3A inhibitor.

*(462)* The warning corresponding to a respective filter in the second plurality of filters comprises a prompt for the subject to indicate whether they have discussed the risk factor underlying the respective filter in the second plurality of filters that was fired with a health care provider. Acknowledgement is obtained from the subject when the subject indicates that they have discussed the risk factor underlying the respective filter in the second plurality of filters that was fired with a health care provider.

*(464)* Obtain acknowledgment from the subject for the warning issued to the subject by any filter in the second plurality of filters.

Fig. 4D

(466) Proceed with a fulfillment process when no filter in the first plurality of filters has been fired and the subject has acknowledged each warning associated with each filter in the second plurality of filters that was fired.

(468) The fulfillment process comprises storing an indication in a subject profile of an initial order for the dihydropyridine-type calcium channel blocker pharmaceutical composition, communicating an over the counter drug facts label for the dihydropyridine-type calcium channel blocker pharmaceutical composition to the subject, and authorizing, upon confirmation from the subject that the over the counter drug facts label has been received and read, provision of the dihydropyridine-type calcium channel blocker pharmaceutical composition to the subject.

(470) Upon confirmation from the subject that the over the counter drug facts label has been received and read, the subject is authorized for provision of a dosage of from 1 mg to 10 mg of dihydropyridine-type calcium channel blocker no more than once per day.

(472) Upon confirmation from the subject that the over the counter drug facts label has been received and read, the subject is authorized for provision of a dosage of from 2.5 mg to 5 mg of dihydropyridine-type calcium channel blocker no more than once per day.

(474) The fulfillment process further comprises storing a destination associated with the subject in the subject profile.

(476) The fulfillment process further comprises coordinating shipping of the dihydropyridine-type calcium channel blocker pharmaceutical composition to a physical address associated with the subject.

Fig. 4E

(484) Run all or a portion of the second plurality of survey results against a third plurality of filters of the first category class. When a respective filter in the third plurality of filters is fired, the subject is deemed not qualified for the dihydropyridine-type calcium channel blocker pharmaceutical composition and the re-fulfillment process is terminated without delivery of the dihydropyridine-type calcium channel blocker pharmaceutical composition to the subject.

(486) The third plurality of filters comprises a second pregnancy filter that is fired at least when the second plurality of survey results indicates that the subject is pregnant or the subject is breastfeeding.

(488) When the subject profile for the subject does not include a recent blood pressure for the subject, obtain, in the second plurality of survey results, a blood pressure status of the subject. The third plurality of filters of the first category class includes a second blood pressure filter that is fired at least when the second plurality of survey results indicates that the subject has hypertension.

(490) The second blood pressure filter is fired when the second plurality of survey results indicates that the systolic blood pressure of the subject is above 130 mm Hg, or the diastolic blood pressure of the subject is above 80 mm Hg.

(492) When the second plurality of survey results indicates that the subject has hypertension, fire the second blood pressure filter and transmit, to the subject, advice to visit a doctor to discuss taking a prescription-strength blood pressure medication.

(494) Obtain, in the second plurality of survey results, a blood pressure status of the subject. Include, in the third plurality of filters of the first category class, a second blood pressure filter that is fired at least when the second plurality of survey results indicates that the subject has hypertension.

(490) The second blood pressure filter is fired when the second plurality of survey results indicates that the systolic blood pressure of the subject is above 130 mm Hg, or the diastolic blood pressure of the subject is above 80 mm Hg.

(492) When the second plurality of survey results indicate that the subject has hypertension, fire the second blood pressure filter and transmit, to the subject, advice to visit a doctor to discuss taking a prescription-strength blood pressure medication.

Fig. 4G (E)

(496) Run all or a portion of the second plurality of survey results against a fourth plurality of filters of the second category class. When a respective filter in the fourth plurality of filters is fired, the subject is provided with a warning corresponding to the respective filter.

(498) The fourth plurality of filters comprise an atherosclerotic cardiovascular event filter that is fired at least when the second plurality of survey results indicates that the subject has experienced an atherosclerotic cardiovascular event or the subject has had a heart procedure since receiving their last provision of the dihydropyridine-type calcium channel blocker pharmaceutical composition, a second drug interaction filter that is fired at least when the second plurality of survey results indicates that the subject has started taking a medication that interacts with the dihydropyridine-type calcium channel blocker pharmaceutical composition since receiving their last provision of the dihydropyridine-type calcium channel blocker pharmaceutical composition, and a second liver disease filter that is fired at least when the second plurality of survey results indicates that the subject has developed symptoms of liver disease since receiving their last provision of the dihydropyridine-type calcium channel blocker pharmaceutical composition.

(500) The second plurality of survey results further comprises whether the subject has experienced a side effect associated with the dihydropyridine-type calcium channel blocker pharmaceutical composition since receiving their last provision of the dihydropyridine-type calcium channel blocker pharmaceutical composition. The fourth plurality of filters further comprises a side effect filter that is fired at least when the second plurality of survey results indicates that the subject has experienced, since receiving their last provision of the dihydropyridine-type calcium channel blocker pharmaceutical composition, a side effect selected from the group consisting of swelling of the legs, swelling of the ankles, tiredness, extreme sleepiness, stomach pain, nausea, dizziness, flushing, arrhythmia, heart palpitations, muscle rigidity, tremors, and abnormal muscle movement.

(502) When a respective filter in the third plurality of filters or fourth plurality of filters is fired, store a record associated with the firing of the respective filter in an adverse event profile comprising records of filter firing events associated with a plurality of subjects.

(504) Obtain acknowledgment from the subject for the warning issued to the subject by any filter in the fourth plurality of filters.

(506) Proceed with the re-fulfillment process when the re-fulfillment process is not already terminated by the firing of a filter in the third plurality of filters and the subject has acknowledged each warning associated with each filter in the fourth plurality of filters that was fired.

(508) The re-fulfillment process further comprises storing an indication in the subject profile of a re-order for the dihydropyridine-type calcium channel blocker pharmaceutical composition, communicating the over the counter drug facts label for the dihydropyridine-type calcium channel blocker pharmaceutical composition to the subject, and authorizing, upon confirmation from the subject that the over the counter drug facts label has been received and read, a re-order provision of the dihydropyridine-type calcium channel blocker pharmaceutical composition to the subject.

Fig. 4I

— 502
Are you or do you plan to become pregnant? Are you breastfeeding or planning to breastfeed?
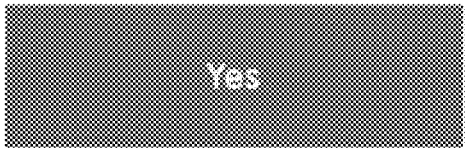 
Fig. 5A
— 504
Amlodipine OTC should be used in pregnancy only if the potential benefits justifies the potential risk to the baby. Only a doctor can decide that. Do not breast-feed while taking Amlodipine OTC.
Thank you for visiting the site.
Fig. 5B Are you taking a blood pressure drug called either amlodipine, nfedipine, or isradipine? —506

—508

Systolic / Diastolic

Continue

Are you taking any of the following:
sildenafil (A medicine to treat erectile dysfunction)
simvastatin (A medicine to treat cholesterol)
cyclosporine (A medicine for immune system)
tacrolimus (A medicine for immune system)
CYP3A Inhibitors (such as diltiazem, itraconazole, clarithromycin)

— 510

Yes  Yes  Yes  Yes  Yes
No   No   No   No   No

Fig. 5E

Amlodipine OTC may not be right for you. Based on your answers, it is important to talk to your doctor about potential risks of taking Amlodipine OTC. It may be helpful to have your summary of answers when talking to your doctor.

Has your doctor said it is OK for you to take Amlodipine OTC?

— 602

METHODS FOR LOWERING BLOOD PRESSURE WITH A DIHYDROPYRIDINE-TYPE CALCIUM CHANNEL BLOCKER PHARMACEUTICAL COMPOSITION

CROSS REFERENCE TO RELATED APPLICATIONS

This application is a Continuation of U.S. application Ser. No. 16/440,319 filed Jun. 13, 2019, which claims priority to U.S. Provisional Patent Application Ser. No. 62/685,209, filed Jun. 14, 2018, both of which are hereby incorporated by reference in their entireties.

TECHNICAL FIELD

The present disclosure relates generally to methods for lowering blood pressure, e.g., thereby treating and/or preventing heart disease, by administering an over-the-counter dihydropyridine-type calcium channel blocker pharmaceutical composition to a subject in need thereof, who has been qualified for over-the-counter access to the composition.

BACKGROUND

Hypertension, e.g., high blood pressure, is the leading cause of death worldwide and the second-leading cause of preventable death in the United States. Roberts, N., et al., Emitro Health, "Feeling the Pressure of New Guidelines for the Treatment of Hypertension," (2017). As of 2014, according to the CDC, 1 in 3 adults in the U.S. was inflicted with high blood pressure and about 46% of those individuals did not have their blood pressure under control. Merai R., et al., MMWR Morb Mortal Wkly Rep, 65:1261-1264 (2016). Of the approximately 35 million U.S. citizens that do not have their blood pressure under control, about 20% are aware that they have high blood pressure, yet are not being treated. Id. The CDC estimates that $49 billion is spent annually in direct and indirect medical expenses relating to uncontrolled hypertension. Id.

Fortunately, hypertension can be managed, for example, using dihydropyridine-type calcium channel blockers, which are well established prescription pharmaceuticals used to lower blood pressure, thereby preventing heart disease. For instance, the efficacy of amlodipine, which was first approved in the U.S. for the treatment of hypertension in 1992, to lower blood pressure has been demonstrated in at least 15 double-blind, placebo-controlled, randomized studies. However, access to dihydropyridine-type calcium channel blockers is restricted by the requirement for a prescription. Unfortunately, long-term trends demonstrate many people avoid prescription medications, including dihydropyridine-type calcium channel blockers.

One approach to making dihydropyridine-type calcium channel blockers more accessible is to make them available without a prescription, e.g., over the counter ("OTC"). There are a variety of health benefits derived from switching a drug from prescription to OTC including, but not limited to, generating wider availably to therapies, providing a greater number of therapeutic approaches, providing direct and rapid access to treatments, providing patients with an active role in their own health care, and allowing patients to become self-reliant in preventing and relieving minor symptoms or conditions (World Health Organization, 2000, "Guidelines for the Regulatory Assessment of Medicinal Products for use in Self-Medication," Print). Given the large number of individuals with uncontrolled high blood pressure, providing access to OTC dihydropyridine-type calcium channel blockers could provide significant societal health benefits.

However, switching distribution of a pharmaceutical from prescription-only to OTC creates a significant risk that the patient population will be unable to appropriately self-select themselves for safe use of the pharmaceutical use and then self-medicate using the drug in a responsible manner. The manifestations embodied within these concerns include incorrect self-diagnosis, incorrect drug-qualification, unrecognized drug-drug interactions (DDI), unanticipated adverse drug reactions and/or side-effects, improper dosing and/or administration, masking of a disease, addiction, inappropriate drug dependency, substance abuse, and patient delay in seeking necessary medical attention. Ruiz et al., Current Drug Safety, 5(4):315 (2010).

In order to ensure the safety of OTC distribution of dihydropyridine-type calcium channel blockers, prospective patients must effectively self-select themselves for the drug. Recent studies, however, found that many prospective patients do not pay consistent attention to guidelines printed on the packaging of OTC drugs, to ensure safe and responsible use. PR Newswire Association, "Americans Should Pay More Attention to Over-the-Counter (OTC) medicine Labels According to New Survey," Oct. 15 (2015) (citing McNeil Consumer Healthcare research). According to these studies, 40% of prospective patients consider the directions as just guidelines and 80% of patients do not re-read the label of an OTC medicine they have used before. Even more troubling, only 58% of men surveyed found it very important to pay attention to restrictions on an OTC label.

Currently, there are two regulatory pathways for legal marketing of an OTC drug in the United States. In the first pathway, marketing occurs in compliance with an OTC drug monograph, that sets regulatory standards for non-prescription drugs that are not covered by human drug applications, e.g., a New Drug Application (NDA) or Abbreviated New Drug Application (ANDA). An OTC monograph is created as a result of a three phase OTC drug review by the FDA. In phase I of the review, an advisory review panel determines whether ingredients in the proposed OTC composition could be generally recognized as safe and effective for use in self-treatment. In the second pathway, marketing occurs under the authority of an approved product-specific new drug application (NDA), or an abbreviated new drug application (ANDA). In order to support an over-the-counter label for a drug for which regulatory approval is being sought through an NDA, a consumer research study is required to assess the consumer's ability to select and deselect themselves as appropriate users of the drug, based on the proposed labeling for the drug. Oliver, A., Regulatory Rapporteur, 10(3):4-9 (2013), which is incorporated by reference herein.

However, attempts at switching distribution of cardiovascular drugs having potentially far-reaching benefits for societal health, from prescription-only to an OTC model, have repeatedly failed, in large part due to concerns over inappropriate patient selection and medication. Possibly the best documented cases relate to statins used to treat high cholesterol.

For instance, Merck has had at least three applications for sale of over the counter lovastatin rejected by the FDA, in 2000, 2005, and 2007. In 2005, their proposal to permit over the counter sales of lovastatin was rejected by an expert advisory panel at the FDA in 2005. The panel was concerned by a marketing study performed to support the proposal in which approximately one third of 3316 customers who were offered the drug over the counter decided they would purchase the drug. After reviewing the data, the panel concluded that 45% of the purchases would have been inappropriate for a variety of reasons, including the age of the subject, the subject's lack of knowledge about their condition, and contraindications associated with their condition. Dyer O., BMJ, 330(7484):164 (2005). In 2007, the board again concluded that the ability of consumers to appropriately self-select and to adequately comply with chronic MEVACOR® therapy without the intervention of a physician had not been demonstrated. Division of Metabolic and Endocrine Drug Products, 2005, "NDA 21-213 Non-prescription MEVACOR® 20 mg Joint Advisory Committee Meeting."

Similarly, Pfizer announced in 2011 its intention to switch LIPITOR® from prescription-only to OTC status. Sett OTC bulletin, 16 Nov. 2011, page 7. However, they abandoned their attempt in 2014 when a phase 3 "actual use" trial, intended to simulate the OTC use of LIPITOR® (atorvastatin calcium) 10 mg, failed to meet its primary objectives on the basis that patient compliance with the direction to check their low-density lipoprotein cholesterol (LDL-C) level and, after checking their LDL-C level, take appropriate action based on their test results was unsatisfactory. Pfizer Inc., "Pfizer Reports Second-Quarter 2015 Results," (2015).

In fact, in the nearly two decades since Bristol-Myers Squibb and Merck & Co first failed in their attempts to switch PRAVACHOL® and lovastatin, respectively, to OTC, a statin has never been granted OTC status in the United States. This is despite that nearly 40 million adults in the U.S. who are eligible for cholesterol-lowering medications, under the current guidelines, are not taking anything.

The information disclosed in this Background section is only for enhancement of understanding of the general background of the invention and should not be taken as an acknowledgment or any form of suggestion that this information forms the prior art already known to a person skilled in the art.

SUMMARY

Given the above background, what is needed in the art are systems and methods for qualifying a human subject for delivery of a dihydropyridine-type calcium channel blocker pharmaceutical composition over-the-counter to lower blood pressure, e.g., thereby, treating or preventing heart disease.

The present disclosure addresses the need in the art for systems and methods configured for qualifying a human subject for over-the-counter delivery of a dihydropyridine-type calcium channel blocker pharmaceutical composition (e.g., amlodipine) in order to treat or prevent heart disease, e.g., by lowering blood pressure. In the present disclosure, systems and methods are provided for over-the-counter delivery of a dihydropyridine-type calcium channel blocker pharmaceutical composition to a subject. Survey results from the subject are run against a first plurality of filters. When a filter in the first plurality is fired, the subject is deemed not qualified for delivery of the dihydropyridine-type calcium channel blocker pharmaceutical composition. The survey results are also run against a second plurality of filters. When a respective filter in the second plurality is fired, the subject is provided with a corresponding warning. The method proceeds to a fulfillment process when no filter in the first plurality is fired and the subject has acknowledged each warning associated with each fired filter in the second plurality of filters. The fulfillment process stores the composition order, communicates a drug facts label for the dihydropyridine-type calcium channel blocker pharmaceutical composition to the subject, and authorizes, upon subject confirmation that the label has been read, provision of the dihydropyridine-type calcium channel blocker pharmaceutical composition to the subject.

Accordingly, one aspect of the present disclosure provides a method for qualifying a subject for over-the-counter delivery of a dihydropyridine-type calcium channel blocker pharmaceutical composition in order to lower the blood pressure of the subject. The method includes conducting a first survey of the subject in order to obtain a variety of survey results. In some embodiments, the survey results include one or more of: whether the subject is pregnant, breastfeeding, or planning to become pregnant, whether the subject is already taking another dihydropyridine-type calcium channel blocker, the current systolic blood pressure of the subject, the current diastolic blood pressure of the subject, whether the subject has ever had an atherosclerotic cardiovascular event or had a heart procedure, the gender of the subject, the age of the subject, the subject's race, whether the subject is taking any blood pressure medications, the diabetes status of the subject, whether the subject smokes, the total cholesterol level of the subject, the high-density lipoprotein (HDL) cholesterol level of the subject, whether the subject has ever had a liver problem, and whether the subject is taking a medication that interacts (e.g., a pharmacokinetic interaction and/or a pharmacodynamic interaction) with the dihydropyridine-type calcium channel blocker pharmaceutical composition.

The method also includes running all or a portion of the survey results against a first plurality of filters of a first category class. When a respective filter in the first plurality of filters is fired, the subject is deemed not qualified for delivery of the dihydropyridine-type calcium channel blocker pharmaceutical composition. The method is then terminated accordingly without delivery of the dihydropyridine-type calcium channel blocker pharmaceutical composition to the subject. In some embodiments, the first plurality of filters includes one or more of a first pregnancy filter, a dihydropyridine medication filter, a first blood pressure filter, an age filter, and a pooled cohort equation filter.

The method also includes running all or a portion of the survey results against a second plurality of filters of a second category class. When a respective filter in the second plurality of filters is fired, the subject is provided with a warning corresponding to the respective filter. In some embodiments, the second plurality of filters includes one or more of a first liver disease filter and a first drug interaction filter. However, unlike filters in the first plurality of filters, filters in the second plurality of filters do not automatically terminate the process without delivery of the dihydropyridine-type calcium channel blocker pharmaceutical composition to the subject.

The method continues by obtaining acknowledgment from the subject for the warning issued to the subject by any filter in the second plurality of filters. In some embodiments, acknowledgment from the subject is a written acknowledgement, a verbal acknowledgment, or an electronic acknowledgment such as an electronic signature.

The method continues by proceeding with a fulfillment process when no filter in the first plurality of filters has been fired and the subject has acknowledged each warning associated with each filter in the second plurality of filters that was fired.

In some embodiments, the fulfillment process includes storing an indication in a subject profile of an initial order for the dihydropyridine-type calcium channel blocker pharmaceutical composition, communicating an over-the-counter drug label for the dihydropyridine-type calcium channel blocker pharmaceutical composition, and authorizing, upon confirmation from the subject that the over-the-counter drug label has been received and read, provision of the dihydropyridine-type calcium channel blocker pharmaceutical composition to the subject.

In some embodiments, the dihydropyridine-type calcium channel blocker pharmaceutical composition has the structure:

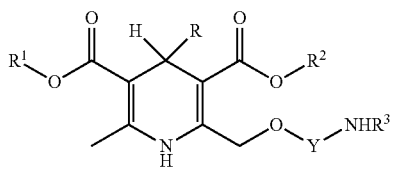

where,
Y is —(CH$_2$)$_2$—, —(CH$_2$)$_3$—, —CH$_2$CH(CH$_3$)—, or —CH$_2$C(CH$_3$)$_2$—;
R is aryl;
R$^1$ and R$^2$ are each independently C$_1$-C$_4$ alkyl or 2-methoxyethyl;
R$^3$ is hydrogen, C$_1$-C$_4$ alkyl, 2—(C$_1$-C$_4$ alkoxy)ethyl, cyclopropylmethyl, benzyl, or —(CH$_2$)$_m$COR$_4$ where m is 1, 2 or 3, and
R$^4$ is hydroxy, C$_1$-C$_4$ alkoxy or —NR$^5$R$^6$ where R$^5$ and R$^6$ are each independently hydrogen or C$_1$-C$_4$ alkyl.
In such embodiments, aryl is phenyl, the phenyl substituted by one or two of nitro, halo, C$_1$-C$_4$ alkyl, C$_1$-C$_4$ alkoxy, hydroxy, trifluoromethyl or cyano, 1-naphthyl, or 2-naphthyl.

In some embodiments, the dihydropyridine-type calcium channel blocker pharmaceutical composition includes amlodipine or a pharmaceutically acceptable salt thereof (e.g., mesylate, maleate, etc.) In some embodiments, the dihydropyridine-type calcium channel blocker pharmaceutical composition includes amlodipine besylate. In some embodiments, the dihydropyridine-type calcium channel blocker pharmaceutical composition includes isradipine, nifedipine, or nisoldipine.

In one aspect, the present disclosure provides a method for qualifying a subject (e.g., a subject who was previously qualified to receive a provision of the dihydropyridine-type calcium channel blocker pharmaceutical composition) for a re-order of the dihydropyridine-type calcium channel blocker pharmaceutical composition (e.g., which is optionally performed in conjunction with a method for qualifying the subject for a first order of the dihydropyridine-type calcium channel blocker pharmaceutical composition). The method includes a re-fulfillment procedure. The re-fulfillment procedure includes conducting a second survey of the subject in order to obtain a second plurality of survey results. In some embodiments, the second survey results includes one or more of: whether the subject is one of pregnant, breastfeeding, or planning to become pregnant, whether the subject has experienced an atherosclerotic cardiovascular event or had a heart procedure since receiving their last provision of the dihydropyridine-type calcium channel blocker pharmaceutical composition, whether the subject has started taking a medication that interacts with the dihydropyridine-type calcium channel blocker pharmaceutical composition since receiving their last provision of the dihydropyridine-type calcium channel blocker pharmaceutical composition, and whether the subject has developed a liver problem since receiving their last provision of the dihydropyridine-type calcium channel blocker pharmaceutical composition.

The method also includes running all or a portion of the second plurality of survey results against a third plurality of filters of the first category class. When a respective filter in the third plurality of filters is fired, the subject is deemed not qualified for the dihydropyridine-type calcium channel blocker pharmaceutical composition. Accordingly, the re-fulfillment process is terminated without delivery of the dihydropyridine-type calcium channel blocker pharmaceutical composition to the subject. In some embodiments, the third plurality of filters comprises a second pregnancy filter that is fired at least when the second plurality of survey results indicates that the subject is pregnant or the subject is breastfeeding.

The method also includes running all or a portion of the second plurality of survey results against a fourth plurality of filters of the second category class. When a respective filter in the fourth plurality of filters is fired the subject is provided with a warning corresponding to the respective filter. In some embodiments, the fourth plurality of filters includes one or more of an atherosclerotic cardiovascular event filter, a second drug interaction filter, and a second liver disease filter.

The method continues by obtaining acknowledgment from the subject for the warning issued to the subject by any filter in the fourth plurality of filters. When the re-fulfillment process is not already terminated by the firing of a filter in the third plurality of filters and the subject has acknowledged each warning associated with each filter in the fourth plurality of filters that was fired, the method continues with a re-fulfillment procedure.

In some embodiments, the re-fulfillment procedure includes storing an indication in the subject profile of a re-order for the dihydropyridine-type calcium channel blocker pharmaceutical composition, communicating an over-the-counter drug facts label for the dihydropyridine-type calcium channel blocker pharmaceutical composition to the subject, and authorizing, upon confirmation from the subject that the over-the-counter drug facts label has been received and read, a re-order provision of the dihydropyridine-type calcium channel blocker pharmaceutical composition to the subject.

In some embodiments, e.g., when the subject profile for the subject does not include a recent blood pressure for the subject, the method includes obtaining a blood pressure status of the subject, e.g., in the second survey, and running the blood pressure status against a second blood pressure filter, e.g., in the third plurality of filters of the first category class.

In some embodiments, the second survey results further include whether the subject has developed a side effect associated with the dihydropyridine-type calcium channel blocker pharmaceutical composition since receiving their last provision of the dihydropyridine-type calcium channel blocker pharmaceutical composition, and the method includes running the result against a side effect filter, e.g., in the fourth plurality of filters of the second category class.

BRIEF DESCRIPTION OF THE DRAWINGS

FIGS. 4A, 4B, 4C, 4D, 4E, 4F, 4G, 4H, and 4I collectively provide a flow chart of processes for qualifying a human subject for over-the-counter delivery of a dihydropyridine-type calcium channel blocker pharmaceutical composition to lower blood pressure, where elements in dashed boxes are optional, in accordance with various embodiments of the present disclosure.

FIGS. 5A, 5B, 5C, 5D, and 5E collectively illustrate a first survey of a subject for obtaining a first plurality of survey results in accordance with an embodiment of the present disclosure.

Figure 1:
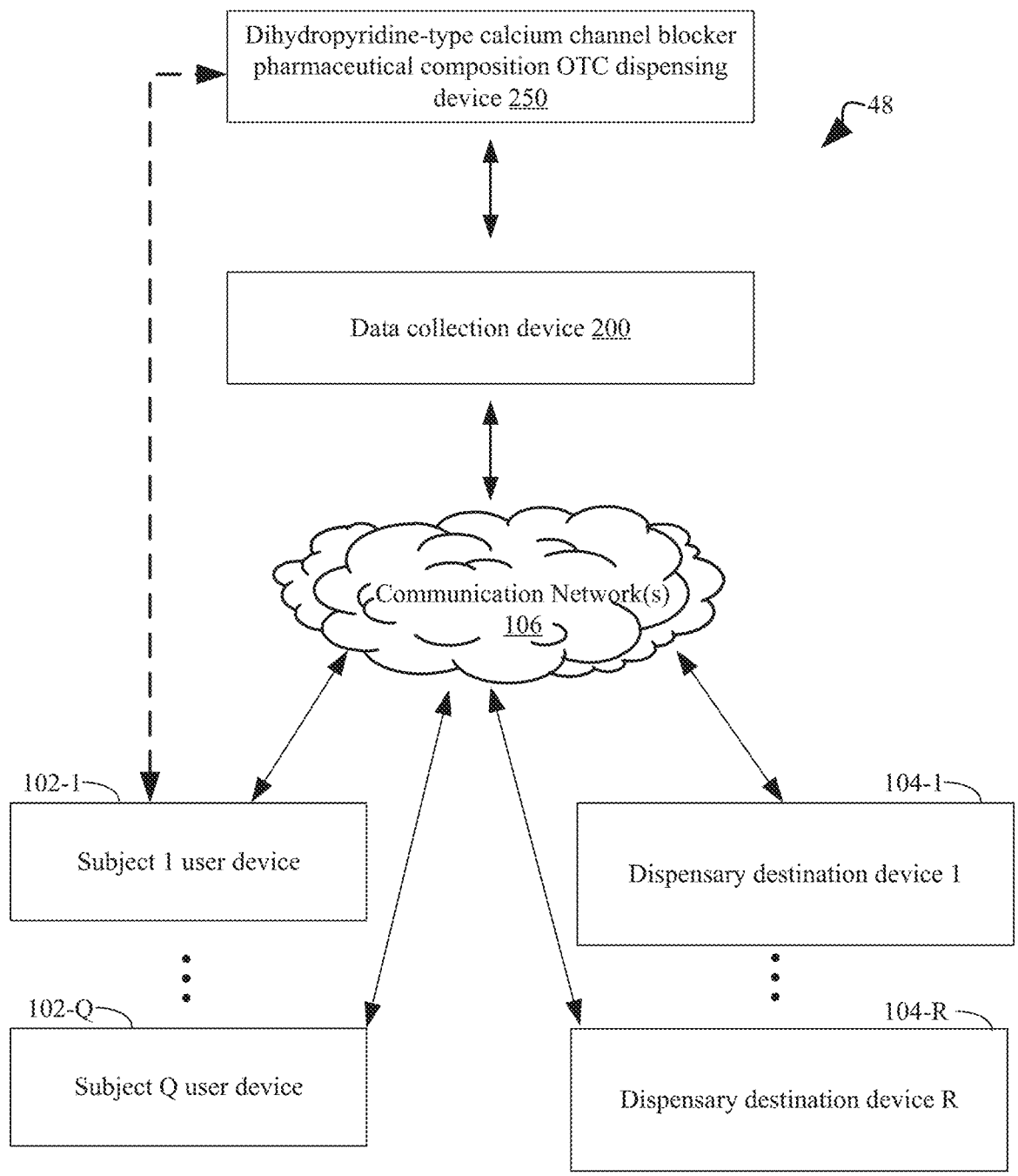
FIG. 1 illustrates an exemplary system topology that includes a dihydropyridine-type calcium channel blocker pharmaceutical composition over-the-counter (OTC) dispensing device for qualifying a human subject for over-the-counter delivery of a dihydropyridine-type calcium channel blocker pharmaceutical composition to lower blood pressure, a data collection device for collecting subject data, one or more user devices associated with human subjects, and one or more dispensary destinations for distributing the dihydropyridine-type calcium channel blocker pharmaceutical composition over-the-counter, where the above-identified components are interconnected, optionally through a communications network, in accordance with an embodiment of the present disclosure.

In the figures, reference numbers refer to the same or equivalent parts of the present invention throughout the several figures of the drawing.

DETAILED DESCRIPTION

Hypertension is a growing health problem, in the United States and worldwide. Although hypertension can be effectively treated and/or prevented using established pharmaceutical compositions, access to these drugs is hindered by to the requirement for a prescription, as many individuals do not have adequate access and/or avoid the healthcare system for a variety of reasons. Accordingly, many people are not managing their hypertension or conditions related to hypertension appropriately. While over-the-counter alternatives to these prescription pharmaceuticals would increase access to these compositions, thereby improving population management of hypertension and conditions related to hypertension around the world, patients often have difficulty self-selecting themselves for an appropriate over-the-counter medication. Because inappropriate use of these drugs can result in ineffective treatment and/or serious side-effects, better methods for selecting for, and treating patients with, other-the-counter hypertension medications are needed. The present disclosure provides, among other aspects, methods, systems, and computer readable media that solve these problems.

Reference will now be made in detail to implementations, examples of which are illustrated in the accompanying drawings. In the following detailed description of implementations, numerous specific details are set forth in order to provide a thorough understanding of the present invention. However, it will be apparent to one of ordinary skill in the art that the present invention may be practiced without these specific details.

It will also be understood that, although the terms first, second, etc. may be used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "over-the-counter" means to provide by retail purchase, subject to the constraints disclosed herein, but without a prescription or license from a physician or medical practitioner.

As used herein, the term "pharmaceutical compound" refers to any physical state of a material. Pharmaceutical compounds include but are not limited to capsules, tablets, liquids, topical formulations, and inhaled formulations.

As used herein, the term "contraindication" refers to a condition that makes a treatment, e.g., over-the-counter use of a dihydropyridine-type calcium channel blocker pharmaceutical composition, inadvisable. Contraindications include physical characteristics of a subject, e.g., pregnancy or liver disease, and contemporaneous drug use, e.g., dihydropyridine-type calcium channel blocker pharmaceutical composition use. In the present context, identification of a contraindication fires a filter of a first category class, which prevents authorizing provision of a dihydropyridine-type calcium channel blocker pharmaceutical composition, in accordance with some implementations of the methods, systems, and software disclosed herein.

As used herein, the term "risk factor" refers to a condition that makes a treatment, e.g., over-the-counter use of a dihydropyridine-type calcium channel blocker pharmaceutical composition, possibly inadvisable. Risk factors include physical characteristics of a subject, e.g., a blood pressure reading, and contemporaneous drug use, e.g., use of a blood pressure medication. In the present context, identification of a risk factor fires a filter of a second category class, which prevents authorizing provision of a dihydropyridine-type calcium channel blocker pharmaceutical composition without confirmation that the subject has discussed the risk factor with a medical professional, in accordance with some implementations of the methods, systems, and software disclosed herein.

As used herein, "drug interactions," e.g., with a dihydropyridine-type calcium channel blocker, include pharmacokinetic drug interactions and pharmacodynamics drug interactions. Generally, a pharmacokinetic drug interaction is an interaction between two drugs (e.g., a dihydropyridine-type calcium channel blocker and a second drug) that result in alterations in the absorption, transport, distribution, metabolism, and/or excretion of either drug. Generally, a pharmacokinetic drug interaction is an interaction between two drugs (e.g., a dihydropyridine-type calcium channel blocker and a second drug) that result in a direct change in the effect or either drug. For a more comprehensive summary of pharmacokinetic drug interactions and pharmacodynamics drug interactions, see, Cascorbi, I, Dtsch Arztebl Int., 109 (33-34):546-55 (2012), the content of which is hereby incorporated by reference.

In the context of the present disclosure, classification of a condition as either a contraindication or a risk factor is specific to a particular identity and dose of a dihydropyridine-type calcium channel blocker pharmaceutical composition being authorized for over-the-counter use. Classification of a particular condition, e.g., contemporaneous dihydropyridine-type calcium channel blocker pharmaceutical composition use, may vary between different dihydropyridine-type calcium channel blocker pharmaceutical compositions (e.g., it may be classified as a contraindication for a first dihydropyridine-type calcium channel blocker, a risk factor for a second dihydropyridine-type calcium channel blocker, and/or neither for a third dihydropyridine-type calcium channel blocker). Likewise, a particular condition may be classified as a contraindication for use of a particular dihydropyridine-type calcium channel blocker at a first over-the-counter dosage, classified as a risk factor for the same particular dihydropyridine-type calcium channel blocker at a second (e.g., lower) over-the-counter dosage, and/or classified as neither for the same particular dihydropyridine-type calcium channel blocker at a third (e.g., lowest) over-the-counter dosage.

As used herein, whether a subject "has developed" a condition since receiving their last provision of a dihydropyridine-type calcium channel blocker refers to both conditions that are new to the subject, i.e., a condition that the subject did not have at the time they received their last provision of the dihydropyridine-type calcium channel blocker, and conditions that have been newly diagnosed, regardless of whether the condition existed when the subject received their last provision of the dihydropyridine-type calcium channel blocker, i.e., a condition that the subject was not aware of when they received their last provision of the dihydropyridine-type calcium channel blocker.

The term "alkyl," by itself or as part of another substituent, means, unless otherwise stated, a straight or branched chain, or cyclic hydrocarbon radical, or combination thereof, which may be fully saturated, mono- or polyunsaturated and can include di-, tri- and multivalent radicals, having the number of carbon atoms designated (e.g. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to optionally include those derivatives of alkyl defined in more detail below, such as "heteroalkyl." Alkyl groups that are limited to hydrocarbon groups are termed "homoalkyl". Exemplary alkyl groups include the monounsaturated $C_{9-10}$, oleoyl chain or the diunsaturated $C_{9-10}$, 12-13 linoeyl chain.

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "cycloalkyl" and "heterocycloalkyl," by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Further exemplary cycloalkyl groups include steroids, e.g., cholesterol and its derivatives. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl substituent groups (or rings) that contain from one to four heteroatoms selected from N, O, S, Si and B, wherein the nitrogen and sulfur atoms are optionally oxidized, and the nitrogen atom(s) are optionally quaternized. An exemplary heteroaryl group is a six-membered azine, e.g., pyridinyl, diazinyl and triazinyl. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes aryl, heteroaryl and heteroarene rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl, and "heteroaryl") are meant to optionally include both substituted and unsubstituted forms of the indicated species. Exemplary substituents for these species are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: H, substituted or unsubstituted aryl, substituted or unsubstituted heteroaryl, substituted or unsubstituted heterocycloalkyl, —OR', =O, =NR', =N—OR', —NR'R", —SR', halogen, —SiR'R"R'", —OC(O)R', —C(O)R', —CO$_2$R', —CONR'R", —OC(O)NR"R'", —NR"C(O)R', —NR'—C(O)NR"R'", —NR"C(O)$_2$R', —NR—C(NR'R"R'")=NR"", NR C(NR'R")=NR'", —S(O)R', —S(O)$_2$R', —S(O)$_2$NR'R", NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). These terms encompass groups considered exemplary "alkyl group substituents," which are components of exemplary "substituted alkyl" and "substituted heteroalkyl" moieties.

Similar to the substituents described for the alkyl radical, substituents for the aryl heteroaryl and heteroarene groups are generically referred to as "aryl group substituents." The substituents are selected from, for example: groups attached to the heteroaryl or heteroarene nucleus through carbon or a heteroatom (e.g., P, N, O, S, Si, or B) including, without limitation, substituted or unsubstituted alkyl, substituted or unsubstituted aryl, substituted or unsubstituted heteroaryl, substituted or unsubstituted heterocycloalkyl, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', NR' C(O)NR"R'", —NR"C(O)$_2$R', NR—C(NR'R"R'")=NR"", NR C(NR'R")=NR'", —S(O)R', —S(O)$_2$R', —S(O)$_2$NR'R", NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system. Each of the above-named groups is attached to the heteroarene or heteroaryl nucleus directly or through a heteroatom (e.g., P, N, O, S, Si, or B); and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

As used herein, the term "heteroatom" includes oxygen (O), nitrogen (N), sulfur (S) and silicon (Si), boron (B) and phosphorous (P).

The symbol "R" is a general abbreviation that represents a substituent group that is selected from H, substituted or unsubstituted alkyl, substituted or unsubstituted heteroalkyl, substituted or unsubstituted aryl, substituted or unsubstituted heteroaryl, and substituted or unsubstituted heterocycloalkyl groups.

The term "salt(s)" includes salts of the compounds prepared by the neutralization of acids or bases, depending on the particular ligands or substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium calcium, ammonium, organic amino, or magnesium salt, or a similar salt. Examples of acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids, and the like, as well as the salts derived from relatively nontoxic organic acids like acetic, propionic, isobutyric, butyric, maleic, malic, malonic, benzoic, succinic, suberic, fumaric, lactic, mandelic, phthalic, benzenesulfonic, p-tolylsulfonic, citric, tartaric, methanesulfonic, and the like. Certain specific compounds of the present invention contain both basic and acidic functionalities that allow the compounds to be converted into either base or acid addition salts. Hydrates of the salts are also included.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure or be stereoisomeric mixtures. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

In one aspect of the present disclosure survey of a subject is conducted to obtain survey results in order to determine if the subject qualifies for an over-the-counter (OTC) dihydropyridine-type calcium channel (e.g., L-type calcium channel, DHP channel) blocker pharmaceutical composition for lowering blood pressure, e.g., thereby, treating or preventing an atherosclerotic cardiovascular disease. The survey results are used as the basis for running filters of a first category class. If the triggering conditions of any of the filters in the first category class are fired, the subject does not qualify for the OTC dihydropyridine-type calcium channel blocker pharmaceutical composition. The survey results are also used as the basis for running filters of a second category class. If the triggering conditions of any of the filters in the second category class are fired, the subject is provided with warning messages associated with the respective filters of the second category class that have been fired. If none of the filters in the first category class are fired and the subject successfully addresses the warning messages associated with the respective filters of the second category class that have been fired a fulfillment process is initiated for OTC delivery of the dihydropyridine-type calcium channel blocker pharmaceutical composition.

FIG. 1 illustrates an example of an integrated system 48 for conducting one or more surveys of subjects in order to qualifying the subjects for OTC delivery of a dihydropyridine-type calcium channel blocker pharmaceutical composition. The integrated system 48 includes one or more connected user devices 102. The user devices 102 are configured for entering survey data and making requests for the dihydropyridine-type calcium channel blocker pharmaceutical composition. The system 48 also includes one or more dispensary destination devices 104 that are configured to receive instructions in order to provide the dihydropyridine-type calcium channel blocker pharmaceutical composition to qualifying subjects. Furthermore, the system 48 includes a dihydropyridine-type calcium channel blocker pharmaceutical composition over-the-counter (OTC) dispensing device 250 and one or more data collection devices 200 that are configured for collecting subject data.

Throughout the present disclosure, the data collection device 200 and the dihydropyridine-type calcium channel blocker pharmaceutical composition OTC dispensing device 250 will be referenced as separate devices solely for purposes of clarity. That is, the disclosed functionality of the data collection device 200 and the disclosed functionality of the dihydropyridine-type calcium channel blocker pharmaceutical composition OTC dispensing device 250 are contained in separate devices as illustrated in FIG. 1. However, it will be appreciated that, in fact, in some embodiments, the disclosed functionality of the data collection device 200 and the disclosed functionality of the dihydropyridine-type calcium channel blocker pharmaceutical composition OTC dispensing device 250 are contained in a single device.

With the integrated system 48, survey results from the subjects are run against a first plurality of filters (e.g., filter 216-1, filter 216-2, filter 216-4, etc.) When a filter in the first plurality of filters (e.g., filter 216) is fired for a respective subject, the respective subject is deemed not qualified for the dihydropyridine-type calcium channel blocker pharmaceutical composition. The survey results are also run against a second plurality of filters (e.g., filter 222-1, filter 222-2, filter 222-6, etc.) When a respective filter in the second plurality is fired for a respective subject, the respective subject is provided with a warning (e.g., filter warning 226) associated with the respective filter. In some embodiments the survey results are run against the first plurality of filters and the second plurality of filters concurrently. In some embodiments the survey results are run against the first plurality of filters and then against the second plurality of filters. The method enabled by the integrated system 48 proceeds to a fulfillment process when no filter in the first plurality fires and the subject has acknowledged, or otherwise successfully addressed, each warning associated with each filter in the second plurality of filters that fired. As part of the fulfillment process, the composition order is stored (e.g., in a user profile 234 associated with the subject to receive the drug), a drug facts label (e.g., drug facts label 230) for the dihydropyridine-type calcium channel blocker is communicated to the qualifying subject. Upon subject confirmation that the label has been read, authorization is granted to dispense the dihydropyridine-type calcium channel blocker.

Referring to FIG. 1, the dihydropyridine-type calcium channel blocker pharmaceutical composition OTC dispensing device 250 qualifies a subject for over-the-counter delivery of a dihydropyridine-type calcium channel blocker pharmaceutical composition to lower blood pressure. To accomplish this, the data collection device 200, which is in electrical communication with the dihydropyridine-type calcium channel blocker pharmaceutical composition OTC dispensing device 250, receives survey results originating from one or more user devices 102 associated with corresponding subjects. In some embodiments, the data collection device 200 receives such survey results directly from the user devices 102. For instance, in some embodiments the data collection device 200 receives this data wirelessly through radio-frequency signals. In some embodiments, such signals are in accordance with an 802.11 (Wi-Fi), Bluetooth, or ZigBee standard. In some embodiments, the data collection device 200 receives such data directly, analyzes the data, and passes the analyzed data to the dihydropyridine-type calcium channel blocker pharmaceutical composition OTC dispensing device 250.

In some embodiments, the data collection device 200 and/or the dihydropyridine-type calcium channel blocker pharmaceutical composition OTC dispensing device 250 is not proximate to the subject and/or does not have wireless capabilities or such wireless capabilities are not used for the purpose of acquiring survey results. In such embodiments, a communication network 106 may be used to survey questions (e.g., survey questions 208, 212) from the dihydropyridine-type calcium channel blocker pharmaceutical composition OTC dispensing device 250 to user devices 102 and the answers to such survey questions from the user devices 102 to the data collection device 200 and/or the dihydropyridine-type calcium channel blocker pharmaceutical composition OTC dispensing device 250. Further, in some embodiments the communication network 106 is used to communicate authorization to dispense the dihydropyridine-type calcium channel blocker survey questions from the dihydropyridine-type calcium channel blocker pharmaceutical composition OTC dispensing device 250 to dispensary destination devices 104.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 are possible. For instance, rather than relying on a communications network 106, the one or more user devices 102 and the one or more dispensary destination devices 104 may communicate directly to the data collection device 200 and/or the dihydropyridine-type calcium channel blocker pharmaceutical composition OTC dispensing device 250. Further, the data collection device 200 and/or the dihydropyridine-type calcium channel blocker pharmaceutical composition OTC dispensing device 250 may constitute a portable electronic device, a server computer, or in fact constitute several computers that are linked together in a network, be a virtual machine in a cloud computing context, be a container in a cloud computer context, or a combination thereof. As such, the exemplary topology shown in FIG. 1 merely serves to describe the features of an embodiment of the present disclosure in a manner that will be readily understood to one of skill in the art.

Figure 2:
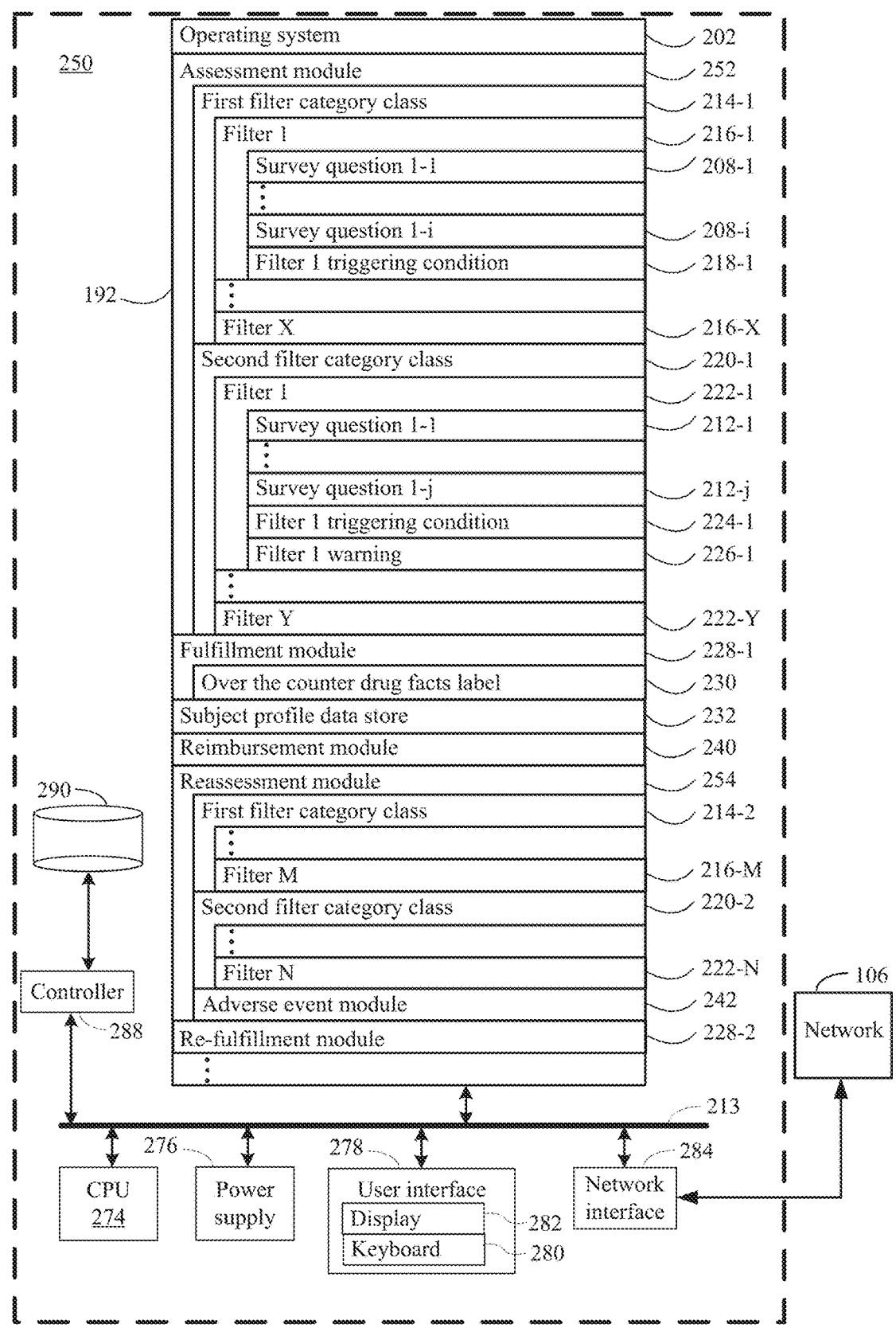
FIG. 2 illustrates an example device for qualifying a human subject for delivery of a dihydropyridine-type calcium channel blocker pharmaceutical composition over-the-counter to lower cholesterol in accordance with various embodiments of the present disclosure.

Turning to FIG. 2 with the foregoing in mind, an exemplary dihydropyridine-type calcium channel blocker pharmaceutical composition OTC dispensing device 250 configured for determining whether a subject is qualified for OTC delivery of a dihydropyridine-type calcium channel blocker is depicted. Referring to FIG. 2, in typical embodiments, the dihydropyridine-type calcium channel blocker pharmaceutical composition OTC dispensing device 250 comprises one or more computers. For purposes of illustration in FIG. 2, the dihydropyridine-type calcium channel blocker pharmaceutical composition OTC dispensing device 250 is represented as a single computer that includes all of the functionality for qualifying a human subject for over-the-counter delivery of a dihydropyridine-type calcium channel blocker pharmaceutical composition to lower blood pressure. However, the present disclosure is not limited thereto. In some embodiments, the functionality for qualifying a human subject for over-the-counter delivery of a dihydropyridine-type calcium channel blocker pharmaceutical composition to lower blood pressure is spread across any number of networked computers and/or resides on each of several networked computers, is hosted on one or more virtual machines at a remote location accessible across the communications network 106, and/or is hosted on one or more containers at a remote location accessible across the communications network 106. One of skill in the art will appreciate that any of a wide array of different computer topologies are used for the application and all such topologies are within the scope of the present disclosure.

The dihydropyridine-type calcium channel blocker pharmaceutical composition OTC dispensing device 250 of FIG. 2 is configured to conduct a first survey (e.g., using assessment module 252 to perform an initial qualification of the subject for provision of a dihydropyridine-type calcium channel blocker pharmaceutical composition) and/or a second survey (e.g., using reassessment module 254 to perform a re-qualification of the subject for provision of a dihydropyridine-type calcium channel blocker pharmaceutical composition). The first survey (e.g., the assessment) comprises a variety of questions 208, 212 associated with filters 216, 222 within a plurality of filters of the first filter category class 214 and a plurality of filters in the second filter category class 220, respectively. Answers to the questions in the first survey received by the device are run against filters of a first category class 216-1 and filters of a second category class 220-1 within the first and second pluralities of filters 214-1, 216-1, respectively. Similarly, the second survey (e.g., the reassessment) also comprises a variety of questions associated with filters 216, 222 within a plurality of filters of a first category class 214-2 and a plurality of filters of a second category class 220-2, respectively. Answers to the questions in the second survey received by the device are run against filters of a first category class 216-2 and filters of a second category class 220-2, e.g., within the first and second pluralities of filters, respectively. Filters 216 of the first filter category class 214 are configured to terminate the qualification process when fired. Filters 222 of the second filter category class 220 are configured to provide the subject with a warning associated with a corresponding survey question. In other words, the device of FIG. 2 is configured to accumulate results from a survey (e.g., survey questions 208 and survey questions 212) and run the results against corresponding filters (e.g., filters 216 and filters 222, respectively) in order to determine if a subject is qualified for OTC delivery of a dihydropyridine-type calcium channel blocker pharmaceutical composition.

In the present disclosure, a plurality of filters refers to a series, or set, or filters in either the first filter category class or the second category class. For instance, in some embodiments, a plurality of filters of the first filter category class 214 can comprise any subset of filters 216 of the first filter category class. As an example, in some embodiments a plurality of filters of the first category class comprises filters 216-1, 216-2, 216-3, . . . , 216-$i$, or any combination thereof. Similarly, a plurality of filters of the second filter category class 220 can comprise any set of filters 222 of the second filter category class. Moreover, in some embodiments a plurality of filters of the second category class comprises filters **222-1, 222-2, 222-3, . . . , 222-*i***, or any combination thereof.

Continuing to refer to FIG. 2, in some embodiments, the dispensing device 250 comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the dihydropyridine-type calcium channel blocker pharmaceutical composition OTC dispensing device 250 but that can be electronically accessed by the dihydropyridine-type calcium channel blocker pharmaceutical composition OTC dispensing device 250 over an Internet, intranet, or other form of network or electronic cable (illustrated as element 106 in FIG. 2) using network interface 284.

In some embodiments, the memory 192 of the dihydropyridine-type calcium channel blocker pharmaceutical composition OTC dispensing device 250 stores one or more of:

an operating system 202 that includes procedures for handling various basic system services;

an assessment module 252 for qualifying a subject for an initial over-the-counter delivery of a dihydropyridine-type calcium channel blocker pharmaceutical composition to lower blood pressure, e.g., treating or preventing heart disease, by communicating survey questions, obtaining results therefrom, and applying the results to qualifying filters, the assessment module including:

a first filter category class 214-1, including filters 216 (e.g., a first plurality of filters), each respective filter 216 in the first filter category class 214-1 associated with one or more survey questions 208 and one or more triggering conditions 218;

a second filter category class 220-1, including filters 222 (e.g., a second plurality of filters), each respective filter 222 in the second filter category class 220-1 associated with one or more survey questions 208, triggering conditions 224, and warnings 226;

a fulfillment module 228-1 for executing a fulfillment process when no filter 216 in the first filter category class 214-1 has been fired for a subject and the subject has acknowledged each warning 226 associated with each filter 222 in the second filter category class 220-1 that was fired as a result of answers by the subject to the survey questions 208, where the fulfillment process includes communicating an over-the-counter drug facts label 230 for the dihydropyridine-type calcium channel blocker pharmaceutical composition to the subject and receiving confirmation from the subject that the over-the-counter drug facts label has been received and read;

a reassessment module 254 for qualifying a subject for a subsequent over-the-counter delivery of a dihydropyridine-type calcium channel blocker pharmaceutical composition to lower blood pressure, e.g., treating or preventing heart disease, by communicating survey questions, obtaining results therefrom, and applying the results to qualifying filters, the assessment module including:

a first filter category class 214-2, including filters 216 (e.g., a third plurality of filters), each respective filter 216 in the first filter category class 214-2 associated with one or more survey questions 208 and one or more triggering conditions 218;

a second filter category class 220-2, including filters 222 (e.g., a second plurality of filters), each respective filter 222 in the second filter category class 220-2 associated with one or more survey questions 208, triggering conditions 224, and warnings 226;

a re-fulfillment module 228-2 for executing a re-fulfillment process when no filter 216 in the first filter category class 214-2 has been fired for a subject and the subject has acknowledged each warning 226 associated with each filter 222-2 in the second filter category class 220 that was fired as a result of answers by the subject to the survey questions 212, where the re-fulfillment process includes communicating an over-the-counter drug facts label 230 for the dihydropyridine-type calcium channel blocker pharmaceutical composition to the subject and receiving confirmation from the subject that the over-the-counter drug facts label has been received and read;

a subject profile data store 232 comprising a user profile 234 for each of a plurality of subjects, each respective user profile 234 including information (e.g., shipping information, billing information, biometric information, etc.) about a corresponding subject in the plurality of subjects, an initial order date and destination 236, and any re-order date and the destination 238 for the dihydropyridine-type calcium channel blocker pharmaceutical composition made by the corresponding subject using the dihydropyridine-type calcium channel blocker pharmaceutical composition OTC dispensing device 250;

an adverse event module 242 for identifying and aggregating records of adverse events associated with a plurality of subjects, e.g., corresponding to the firing of a filter 216 in the first filter category class 214-2 during a re-fulfillment process;

a reimbursement module 240 for determining eligibility and/or communicating an insurance claim associated with delivery of the dihydropyridine-type calcium channel blocker, e.g., based on insurance information stored in a respective user profile 234.

In some embodiments, the assessment module 252, reassessment module 254, and/or fulfillment module 228 are accessible within any browser (e.g., phone, tablet, laptop/desktop, or smartwatch). In some embodiments, the assessment module 252, reassessment module 254, and/or fulfillment module 228 run on native device frameworks, and is available for download onto a user device 102 running an operating system 202 such as Android, iOS, or WINDOWS.

In some implementations, one or more of the above identified data elements or modules (e.g., assessment module 252, fulfillment module 228-1, etc.) of the dihydropyridine-type calcium channel blocker pharmaceutical composition OTC dispensing device 250 for qualifying a human subject for over-the-counter delivery of a dihydropyridine-type calcium channel blocker pharmaceutical composition to lower blood pressure are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above.

In some embodiments, a dihydropyridine-type calcium channel blocker pharmaceutical composition OTC dispensing device 250 for qualifying a human subject for over-the-counter delivery of a dihydropyridine-type calcium channel blocker pharmaceutical composition to lower blood pressure is a smart phone (e.g., an iPhone, Blackberry, etc.), a laptop, a tablet computer, a desktop computer, a smart watch, or another form of electronic device (e.g., a gaming console). In some embodiments, the dihydropyridine-type calcium channel blocker pharmaceutical composition OTC dispensing device 250 is not mobile. In some embodiments, the dihydropyridine-type calcium channel blocker pharmaceutical composition OTC dispensing device 250 is mobile.

In some embodiments, the dihydropyridine-type calcium channel blocker pharmaceutical composition OTC dispensing device 250 is not a smart phone but rather is a tablet computer, desktop computer, emergency vehicle computer, or other form or wired or wireless networked device. In the interest of brevity and clarity, only a few of the possible components of the dihydropyridine-type calcium channel blocker pharmaceutical composition OTC dispensing device 250 are shown in FIG. 2 in order to better emphasize the additional software modules that are installed on the dihydropyridine-type calcium channel blocker pharmaceutical composition OTC dispensing device 250.

Figure 3:
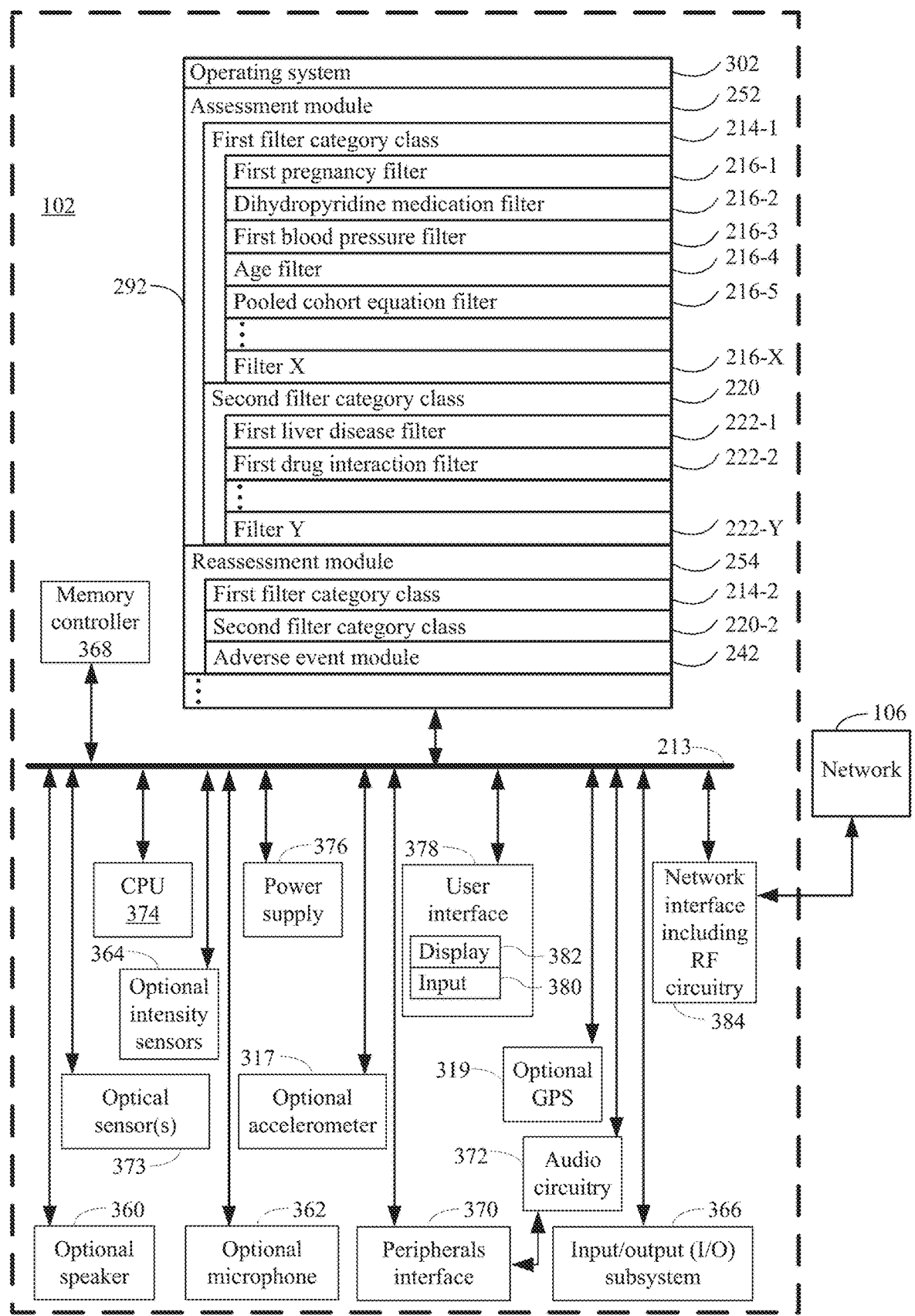
FIG. 3 illustrates an example device associated with a human subject for qualifying the human subject for over-the-counter delivery of a gliflozin Sodium-Glucose Cotransport 2 inhibitor pharmaceutical composition for lowering blood sugar, e.g., thereby treating Type 2 diabetes and/or maintaining sub-diabetic blood sugar levels, in accordance with an embodiment of the present disclosure, where it will be appreciated that the example device of FIG. 3 works in conjunction with the device of FIG. 2 to perform the methods illustrated in FIGS. 4 through 8 in some embodiments by, for instance providing the device of FIG. 2 with survey results and/or the results of firing filters of the present disclosure against such survey results but that, in alternative embodiments, the device of FIG. 2 performs all the methods of the present disclosure and the device of FIG. 3 is not used. In still further alternative embodiments, the device of FIG. 3 performs the methods of the present disclosure and the device of FIG. 2 is not used.

FIG. 3 provides a description of a user device 102 that can be used with the present disclosure. The user device 102 illustrated in FIG. 3 has one or more processing units (CPU's) 374, peripherals interface 370, memory controller 368, a network or other communications interface 384, a memory 392 (e.g., random access memory), a user interface 378, the user interface 378 including a display 382 and input 380 (e.g., keyboard, keypad, touch screen), an optional accelerometer 317, an optional GPS 319, optional audio circuitry 372, an optional speaker 360, an optional microphone 362, one or more optional intensity sensors 364 for detecting intensity of contacts on the user device 102 (e.g., a touch-sensitive surface such as a touch-sensitive display system 382 of the user device 102), an optional input/output (I/O) subsystem 366, one or more optional optical sensors 373, one or more communication busses 313 for interconnecting the aforementioned components, and a power supply 376 for powering the aforementioned components.

In some embodiments, the input 380 is a touch-sensitive display, such as a touch-sensitive surface. In some embodiments, the user interface 378 includes one or more soft keyboard embodiments. The soft keyboard embodiments may include standard (e.g., QWERTY) and/or non-standard configurations of symbols on the displayed icons.

The user device 102 illustrated in FIG. 3 optionally includes, in addition to accelerometer(s) 317, a magnetometer (not shown) and a GPS 319 (or GLONASS or other global navigation system) receiver for obtaining information concerning the location and orientation (e.g., portrait or landscape) of the user device 102 and/or for determining an amount of physical exertion by the subject.

It should be appreciated that the user device 102 illustrated in FIG. 3 is only one example of a multifunction device that may be used for performing a survey (e.g., first survey 206) in order to qualify for over-the-counter delivery of a dihydropyridine-type calcium channel blocker pharmaceutical composition to lower blood pressure, and that the user device 102 optionally has more or fewer components than shown, optionally combines two or more components, or optionally has a different configuration or arrangement of the components. The various components shown in FIG. 3 are implemented in hardware, software, firmware, or a combination thereof, including one or more signal processing and/or application specific integrated circuits.

Memory 392 of the user device 102 illustrated in FIG. 3 optionally includes high-speed random access memory and optionally also includes non-volatile memory, such as one or more magnetic disk storage devices, flash memory devices, or other non-volatile solid-state memory devices. Access to memory 392 by other components of the dihydropyridine-type calcium channel blocker pharmaceutical composition OTC dispensing device 250, such as CPU(s) 374 is, optionally, controlled by the memory controller 368. In some embodiments, the memory 392 of the user device 102 illustrated in FIG. 3 optionally includes:

- an operating system 302 that includes procedures for handling various basic system services;
- the assessment module 252 described above in conjunction with the dihydropyridine-type calcium channel blocker pharmaceutical composition OTC dispensing device 250;
- the first category class 214 described above in conjunction with the dihydropyridine-type calcium channel blocker pharmaceutical composition OTC dispensing device 250 further comprising a pregnancy filter 216-1, a dihydropyridine-type calcium channel blocker filter 216-2, a first blood pressure filter 216-3, a second blood pressure filter 216-4, an age filter 216-5, and a pooled cohort equation filter 216-6; and
- the second category class 220 described above in conjunction with the dihydropyridine-type calcium channel blocker pharmaceutical composition OTC dispensing device 250 comprising a liver disease filter 222-1, a pooled cohort equation filter 222-2, an age filter 222-3, a drug interaction filter 222-4, an alcohol consumption filter 222-5, an adverse reaction filter 222-6, and an atherosclerotic cardiovascular event filter 222-7;

In some embodiments, the optional accelerometer 317, optional GPS 319, and/or magnetometer (not shown) of the user device 102 or such components are used to recommend to qualifying subjects one or more suitable destinations for delivery of the dihydropyridine-type calcium channel blocker pharmaceutical composition over-the-counter. In some embodiments, the GPS 319 is used to determine if a subject is geographically restricted for OTC delivery of the dihydropyridine-type calcium channel blocker pharmaceutical composition. Geographical restrictions include but are not limited to a subject residing outside of delivery or shipping regions, marketing restrictions, and/or government regulations.

The peripherals interface 370 can be used to couple input and output peripherals of the device to CPU(s) 374 and memory 392. The one or more processors 374 run or execute various software programs and/or sets of instructions stored in memory 392, such as the survey module 204, to perform various functions for the user device 102 and to process data.

In some embodiments, the peripherals interface 370, CPU(s) 374, and memory controller 368 are, optionally, implemented on a single chip. In some other embodiments, they are implemented on separate chips.

RF (radio frequency) circuitry of network interface 384 receives and sends RF signals, also called electromagnetic signals. In some embodiments, the survey module 204, survey questions 208/212, answers to survey questions 208/212, and/or the over-the-counter drug facts label 230 are communicated to the subject device 102 using this RF circuitry. In some embodiments, the RF circuitry 384 converts electrical signals to/from electromagnetic signals and communicates with communications networks and other communications devices and/or the data collection device 200 and/or the dihydropyridine-type calcium channel blocker pharmaceutical composition OTC dispensing device 250 via the electromagnetic signals. The RF circuitry 384 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 384 optionally communicates with the communication network 106. In some embodiments, the circuitry 384 does not include RF circuitry and, in fact, is connected to the network 106 through one or more hard wires (e.g., an optical cable, a coaxial cable, or the like).

In some embodiments, the audio circuitry 372, the optional speaker 360, and the optional microphone 362 provide an audio interface between the subject and the user device 102. The audio circuitry 372 receives audio data from the peripherals interface 370, converts the audio data to electrical signals, and transmits the electrical signals to the speaker 360. The speaker 360 converts the electrical signals to human-audible sound waves. In some embodiments, the speaker 260 converts the electrical signals to human-inaudible sound waves. The audio circuitry 372 also receives electrical signals converted by the microphone 362 from sound waves. The audio circuitry 372 converts the electrical signal to audio data and transmits the audio data to peripherals interface 370 for processing. Audio data is, optionally, retrieved from and/or transmitted to the memory 392 and/or the RF circuitry 384 by the peripherals interface 370.

In some embodiments, the power supply 376 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

In some embodiments, the user device 102 optionally also includes one or more optical sensors 373. The optical sensor(s) 373 optionally include charge-coupled device (CCD) or complementary metal-oxide semiconductor (CMOS) phototransistors. The optical sensor(s) 373 receive light from the environment, projected through one or more lens, and converts the light to data representing an image. The optical sensor(s) 373 optionally capture still images and/or video. In some embodiments, an optical sensor is located on the back of the user device 102, opposite the display 382 on the front of the user device 102, so that the input 380 is enabled for use as a viewfinder for still and/or video image acquisition. In some embodiments, another optical sensor 373 is located on the front of the user device 102 so that the subject's image is obtained (e.g., to verify the health, condition, or identity of the subject as part of qualifying the subject for over-the-counter delivery of a dihydropyridine-type calcium channel blocker pharmaceutical composition to lower blood pressure), to help diagnose a subject's condition remotely, or to acquire visual physiological measurements of the subject, etc.)

As illustrated in FIG. 3, the user device 102 preferably comprises an operating system 302 that includes procedures for handling various basic system services. The operating system 302 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the user device 102 is a smart phone or a smart watch. In other embodiments, the user device 102 is not a smart phone or a smart watch but rather is a tablet computer, a desktop computer, an emergency vehicle computer, or other form or wired or wireless networked device. In the interest of brevity and clarity, only a few of the possible components of the user device 102 are shown in FIG. 3 in order to better emphasize the additional software modules that are installed on the user device 102.

While the system 48 disclosed in FIG. 1 can work standalone, in some embodiments it can also be linked with electronic medical record systems to exchange information in any way.

Now that details of a system 48 for qualifying a human subject for over-the-counter delivery of a dihydropyridine-type calcium channel blocker pharmaceutical composition to lower blood pressure have been disclosed, details regarding a method (400), including processes and features to be performed by the system, in accordance with an embodiment of the present disclosure, are disclosed with reference to FIGS. 4A through 4I. In some embodiments, such processes and features of the system are carried out by the assessment module 252, reassessment module 254, fulfillment module 228-1, and/or re-fulfillment module 228-2 illustrated in FIGS. 2 and 3. In some embodiments, the assessment module 252, reassessment module 254, fulfillment module 228-1, and/or re-fulfillment module 228-1 are a single software module. In the flow chart, elements in dashed boxes are considered to be optional.

Blocks 402-412. Referring to block 402 of FIG. 4A, a goal of the present disclosure is to qualify subjects for over-the-counter delivery of a dihydropyridine-type calcium channel blocker pharmaceutical composition to lower blood pressure, e.g., thereby, treating and/or preventing heart disease, using a computer system such as a dihydropyridine-type calcium channel blocker pharmaceutical composition OTC dispensing device 250. As illustrated in FIG. 2, the dihydropyridine-type calcium channel blocker pharmaceutical composition OTC dispensing device (e.g., device 250) comprises one or more processors (e.g., processor 274) and a memory (e.g., memory 192 and/or 290). The memory stores non-transitory instructions that, when executed by the one or more processors, perform a method.

Referring to block 404, in some embodiments the dihydropyridine-type calcium channel blocker pharmaceutical composition the dihydropyridine-type calcium channel blocker pharmaceutical composition has a structure of structure (I):

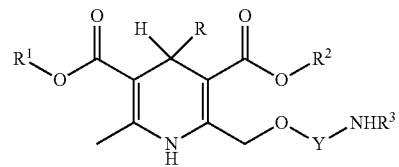

where:
Y is —$(CH_2)_2$—, —$(CH_2)_3$—, —$CH_2CH(CH_3)$—, or —$CH_2C(CH_3)_2$—;
R is aryl;
$R^1$ and $R^2$ are each independently $C_1$-$C_4$ alkyl or 2-methoxyethyl;
$R^3$ is hydrogen, $C_1$-$C_4$ alkyl, 2—($C_1$-$C_4$ alkoxy)ethyl, cyclopropylmethyl, benzyl, or —$(CH_2)_m COR^4$ where m is 1, 2 or 3 and $R^4$ is hydroxy, $C_1$-$C_4$ alkoxy or —$NR^5 R^6$ where $R^5$ and $R^6$ are each independently hydrogen or $C_1$-$C_4$ alkyl.

In some embodiments, aryl is phenyl, the phenyl substituted by one or two of nitro, halo, $C_1$-$C_4$ alkyl, $C_1$-$C_4$ alkoxy, hydroxy, trifluoromethyl or cyano, 1-naphthyl, or 2-naphthyl.

Referring to blocks 406-410, in some embodiments the dihydropyridine-type calcium channel blocker pharmaceutical composition includes amlodipine. In some embodiments, the dihydropyridine calcium channel blocker includes a pharmaceutically acceptable salt of amlodipine (e.g., mesylate, maleate). In some embodiments, the dihydropyridine-type calcium channel blocker pharmaceutical composition includes amlodipine besylate.

In some embodiments, the dihydropyridine-type calcium channel blocker pharmaceutical composition includes one of isradipine (e.g., 3-methyl 5-propan-2-yl 4-(2,1,3-benzoxadiazol-4-yl)-2,6-dimethyl-1,4-dihydropyridine-3,5-dicarboxylate), nifedipine (e.g., 3,5-dimethyl 2,6-dimethyl-4-(2-nitrophenyl)-1,4-dihydropyridine-3,5-dicarboxylate), nisoldipine (e.g., isobutyl methyl 2,6-dimethyl-4-(2-nitrophenyl)-1,4-dihydropyridine-3,5-dicarboxylate). These dihydropyridine-type calcium channel blocker compositions are described in McDonagh M S, et al., "Calcium Channel Blockers," Final Report, Portland (Oreg.): Oregon Health & Science University (2005), the content of which is hereby incorporated by reference.

In some embodiments, the dihydropyridine-type calcium channel blocker pharmaceutical composition comprises any compound disclosed in U.S. Pat. No. 4,879,303, entitled "Pharmaceutically Acceptable Salts," which is hereby incorporated by reference. In some embodiments, the dihydropyridine-type calcium channel blocker pharmaceutical composition comprises any compound disclosed in U.S. Pat. No. 4,572,909, entitled "2-(Secondary aminoalkoxymethyl) dihydropyridine derivatives as anti-ischaemic and antihypertensive agents," which is hereby incorporated by reference.

In some embodiments, the dihydropyridine-type calcium channel blocker pharmaceutical composition comprises any compound disclosed in U.S. Pat. No. 4,264,611, entitled "2,6-Dimethyl-4-2,3-disubstituted phenyl-1,4-dihydro-pyridine-3,5-dicarboxylic acid-3,5-asymmetric diesters having hypotensive properties, as well as method for treating hypertensive conditions and pharmaceutical preparations containing same," which is hereby incorporated by reference. In some embodiments, the dihydropyridine-type calcium channel blocker pharmaceutical composition comprises any compound disclosed in U.S. Pat. No. 4,803,081, entitled "New Pharmaceutical Preparations with Extended Release," which is hereby incorporated by reference.

In some embodiments, the dihydropyridine-type calcium channel blocker pharmaceutical composition comprises any compound disclosed in U.S. Pat. No. 4,412,986, entitled "Nifedipine-containing Solid Preparation Composition," which is hereby incorporated by reference. In some embodiments, the dihydropyridine-type calcium channel blocker pharmaceutical composition comprises any compound disclosed in U.S. Pat. No. 3,784,684, entitled "Coronary Dilator in a Pharmaceutical Dosage Unit Form," which is hereby incorporated by reference. In some embodiments, the dihydropyridine-type calcium channel blocker pharmaceutical composition comprises any compound disclosed in U.S. Pat. No. 3,644,627, entitled "Pharmaceutical compositions and methods for producing coronary dilation with 4-aryl-1,4-dihydropyridine derivatives," which is hereby incorporated by reference.

In some embodiments, the dihydropyridine-type calcium channel blocker pharmaceutical composition comprises any compound disclosed in U.S. Pat. No. 4,466,972, entitled "Benzoxadiazoles and Benzothiadiazoles, Their Preparation and Pharmaceutical Compositions Containing Them," which is hereby incorporated by reference.

Contraindications described in the present disclosure are non-exhaustive. The skilled artisan may know of other contraindications for a particular the dihydropyridine-type calcium channel blocker pharmaceutical composition and/or treat risk factors as contraindications dependent upon the intended use of the dihydropyridine-type calcium channel blocker pharmaceutical composition. In some embodiments, contraindications for use of a prescription-strength pharmaceutical agent are treated only as risk factors, or not at all, when qualifying a subject for a lower-dose OTC use of a dihydropyridine-type calcium channel blocker pharmaceutical composition.

Referring to block 412, in some embodiments, the lowering of blood pressure is to treat or prevent heart disease. Typically, this is accomplished by a reduction in systemic vascular resistance and/or arterial pressure.

In some embodiments, a subject that has not received an over-the-counter provision of the dihydropyridine-type calcium channel blocker will register as a new user, and the device will create a corresponding user profile (e.g., regardless of whether the subject previously received a prescription provision of the dihydropyridine-type calcium channel blocker. In some embodiments, the subject will register as a returning customer, e.g., if the subject has previously received an over-the-counter provision of the dihydropyridine-type calcium channel blocker and a corresponding user profile 234 already exists for the user.

In some embodiments, the subject is prompted (702) to confirm that they have adequate privacy to provide sensitive medical information and/or that they are in possession of medical information required to complete the qualification process. For example, in some embodiments the subject is prompted (704) to confirm that they have knowledge of their blood pressure, total cholesterol level, and HDL level.

Blocks 414-416 Referring to block 414 of FIG. 4A, the method includes conducting a first survey of the subject. By way of the first survey, a first plurality of survey results to survey questions 208, 212 (e.g., one or more of the survey questions set forth in Table 1) are obtained (e.g., the device transmits one or more survey questions to the user, prompting a response, and then receives a response to the one or more survey questions back from the subject). In some embodiments, the first survey results include some or all of the characteristics listed in Table 1. For example, in some embodiments, the first plurality of survey results includes 2, 3, 4, 5, 6, 7, 8, 9, 10, 11, 12, 13, 14, 15, or all 16 of the characteristics listed in Table 1. In one embodiment, the first survey questions 208, 212 and results include at least characteristics 1-15 as provided in Table 1.

It will be appreciated that the survey questions 208, 212 and filters 216, 222 applied to the survey answers thereof may vary depending upon the dihydropyridine-type calcium channel blocker pharmaceutical composition being distributed. This is due to differences in the contra-indication profiles of the various the dihydropyridine-type calcium channel blocker pharmaceutical compositions, e.g., due to different drug-drug interactions, routes of drug clearance, etc. of the different the dihydropyridine-type calcium channel blocker pharmaceutical compositions. For example, co-administration of 240 milliliters (mL) of grapefruit juice with a single oral dose of amlodipine 10 milligrams (mg) had no significant effect on the pharmacokinetics of amlodipine. However, co-administration of nifedipine with grapefruit juice resulted in approximately a doubling in nifedipine blood the area under the curve of blood concentration versus time (AUC) and maximum serum concentration ($C_{max}$) with no change in half-life. As such, in some embodiments, a survey qualifying a subject for OTC use of nifedipine may ask whether the subject consumes grapefruit in their diet, while a survey qualifying a subject for OTC use of amlodipine may not.

Figure 5C:
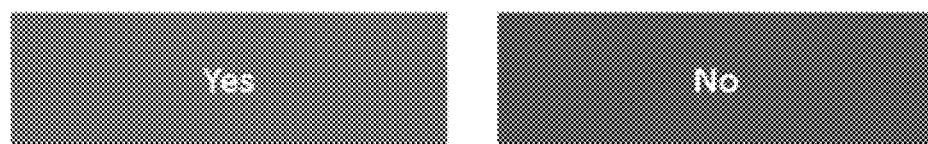
Figure 7A:
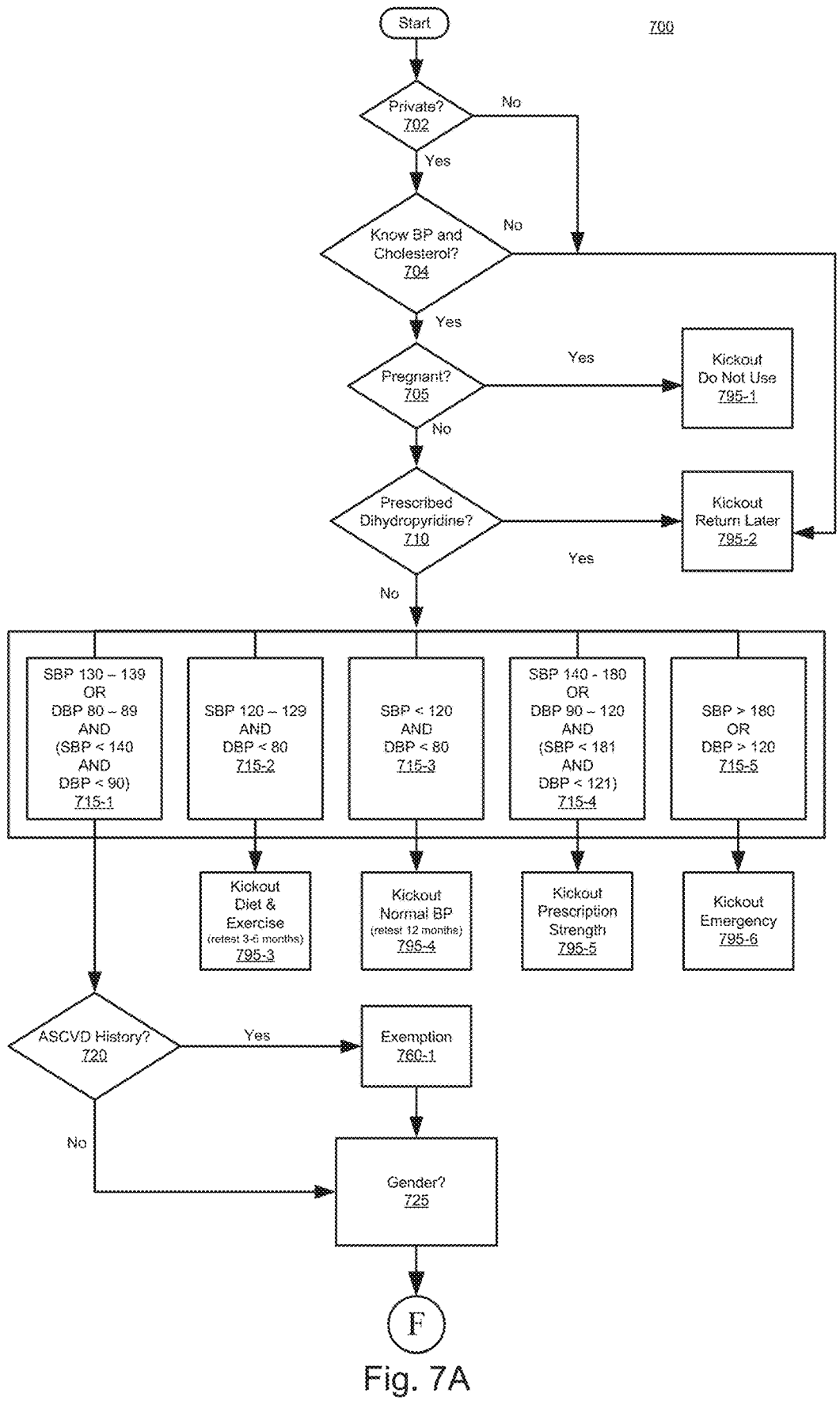
FIGS. 7A, 7B, and 7C collectively illustrate an example method for qualifying a subject for an over-the-counter provision of a dihydropyridine-type calcium channel blocker pharmaceutical composition, in accordance with an embodiment of the present disclosure.
Figure 7B:
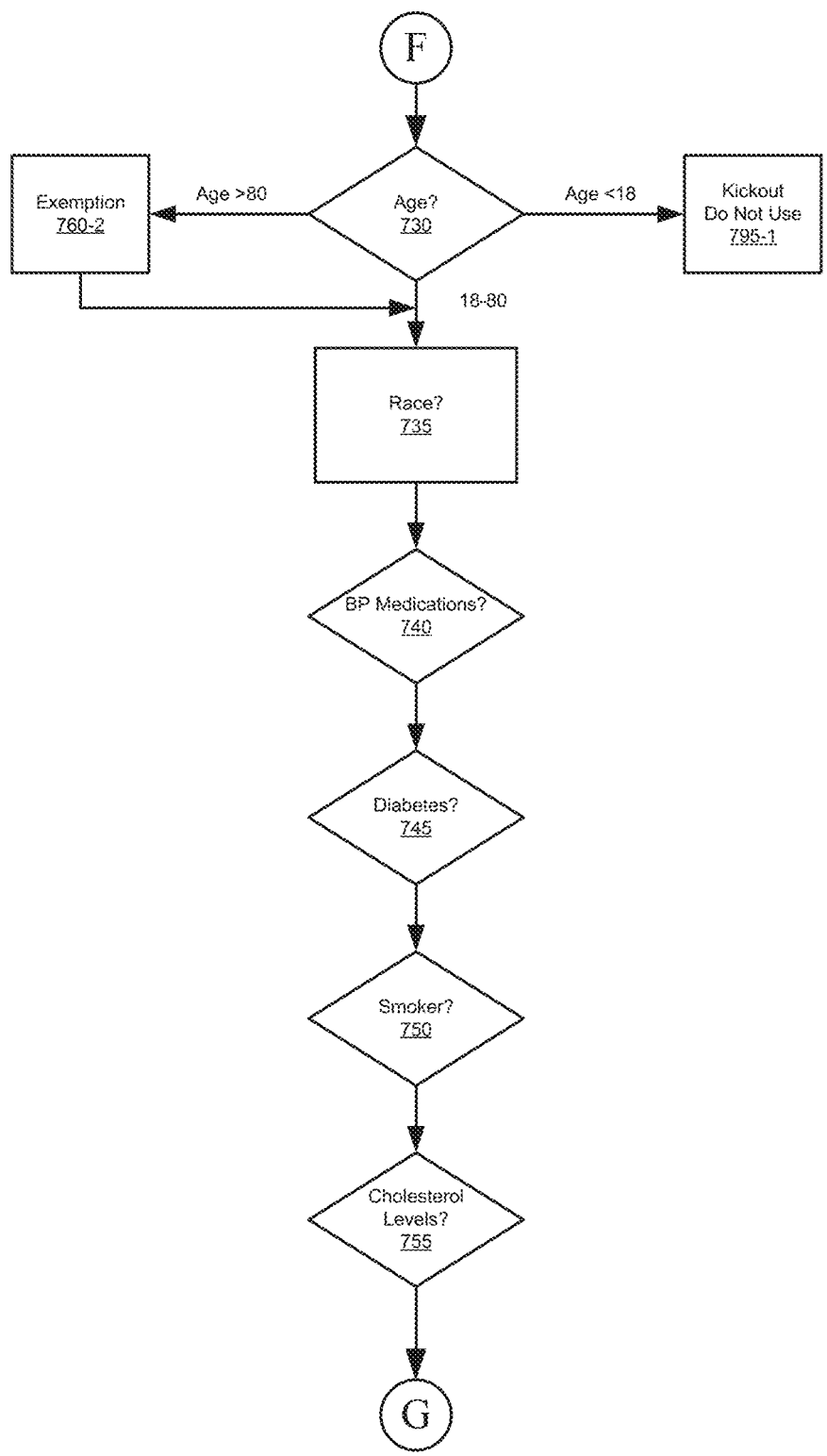

Referring to block 416, and as further illustrated in FIG. 7, in some embodiments the first survey results include whether the subject is one of pregnant, breastfeeding, or planning to become pregnant (e.g., responsive to a survey question 502 such as the one illustrated in FIG. 5A, e.g., that is associated with and/or applied to (705) a pregnancy filter 216 of a first category class), whether the subject is taking a dihydropyridine-type calcium channel blocker (e.g., responsive to a survey question 208 that is associated with and/or applied to (710) a dihydropyridine medication filter 216 of a first category class), a systolic blood pressure of the subject (e.g., responsive to a survey question 208 that is associated with and/or applied to (715, 765) a blood pressure filter 216 of a first category class and/or a pooled cohort equation filter 216 of a first category class), a diastolic blood pressure of the subject (e.g., responsive to a survey question 208 that is associated with and/or applied to (715) a blood pressure filter 216 of a first category class), whether the subject has ever had an atherosclerotic cardiovascular event (e.g., hospitalization for angina pectoris, coronary revascularization, myocardial infarction, cardiovascular death, resuscitated cardiac arrest, hospitalization for heart failure, stroke/TIA, or peripheral vascular disease) or had a heart procedure (e.g., responsive to a survey question 208 that is associated with and/or applied to (765) a pooled cohort equation filter 216 of a first category class), a gender of the subject (e.g., responsive to a survey question 208 that is associated with and/or applied to (765) a pooled cohort equation filter 216 of a first category class), an age of the subject (e.g., responsive to a survey question 208 that is associated with and/or applied to (730, 765) an age filter 216 of a first filter class category and/or a pooled cohort equation filter 216 of a first category class), a race of the subject (e.g., responsive to a survey question 208 that is associated with and/or applied to (765) a pooled cohort equation filter 216 of a first category class), whether the subject is taking any blood pressure medications (e.g., responsive to a survey question 208 that is associated with and/or applied to (765) a pooled cohort equation filter 216 of a first category class), a diabetes status of the subject (e.g., responsive to a survey question 208 that is associated with and/or applied to (765) a pooled cohort equation filter 216 of a first category class), a smoking status of the subject (e.g., responsive to a survey question 208 that is associated with and/or applied to (765) a pooled cohort equation filter 216 of a first category class), a total cholesterol level of the subject (e.g., responsive to a survey question 208 that is associated with and/or applied to (765) a pooled cohort equation filter 216 of a first category class), a high-density lipoprotein (HDL) cholesterol level of the subject (e.g., responsive to a survey question 208 that is associated with and/or applied to (765) a pooled cohort equation filter 216 of a first category class), whether the subject has ever had a liver problem (e.g., responsive to a survey question 208 that is associated with and/or applied to (770) a liver disease filter 222 of a second category class), and whether the subject is taking one or more medications that interact with the dihydropyridine-type calcium channel blocker pharmaceutical composition, (e.g., responsive to a survey question 208 that is associated with and/or applied to (775) a drug interaction filter 222 of a second category class).

In some embodiments, the first survey includes questions that elicit responses providing some or all of the characteristics listed in Table 1. In some embodiments, the survey includes questions corresponding to each of the survey results required for the methods described herein. In other embodiments, the survey includes questions corresponding to only a subset of the survey results required for the methods described herein. In such embodiments, other survey results required for the methods described herein are acquired through other means (e.g., upon registration/subscription for a service associated with qualifying the subject for over-the-counter medication, from a healthcare provider, from a prior survey, from a database associated with a pharmacy, from an electronic health record associated with the subject, from the subject profile data store 232, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a last cholesterol or blood pressure measurement determined for the subject).

TABLE 1

Exemplary First Survey Questions

| Result | Exemplary Characteristics |
|---|---|
| 1 | whether the subject pregnant or breastfeeding |
| 2 | whether the subject is already taking a dihydropyridine-type calcium channel blocker |
| 3 | a systolic blood pressure of the subject |
| 4 | a diastolic blood pressure of the subject |
| 5 | whether the subject has ever had an atherosclerotic cardiovascular event or a had a heart procedure |
| 6 | a gender of the subject |
| 7 | an age of the subject |
| 8 | a race of the subject |
| 9 | whether the subject is taking any blood pressure medications |
| 10 | a diabetes status of the subject |
| 11 | a smoking status of the subject |
| 12 | a total cholesterol of the subject |
| 13 | a HDL cholesterol level of the subject |
| 14 | whether the subject has ever had a liver problem |
| 15 | whether the subject is taking a medication that interacts with the dihydropyridine-type calcium channel blocker pharmaceutical composition |
| 16 | whether the subject is allergic to the dihydropyridine-type calcium channel blocker pharmaceutical composition |

It is contemplated that, in some embodiments, any one or more of the survey questions 208, 212 provided in Table 1 will not be included in the first survey (e.g., will not be used for the assessment. For example, in some embodiments, a characteristic associated with a particular survey questions will be informative when qualifying a subject for one particular dihydropyridine-type calcium channel blocker but not for another dihydropyridine-type calcium channel blocker. For instance, a survey question is queried for amlodipine qualifying surveys but not for isradipine qualifying surveys. The skilled artisan will recognize that different dihydropyridine-type calcium channel blockers carry different risk and drug interaction profiles. Accordingly, survey information required for qualifying a subject for access to one dihydropyridine-type calcium channel blocker with a known adverse drug interaction may not be necessary for qualifying the same subject for access to a second dihydropyridine-type calcium channel blocker.

Accordingly, it is contemplated that the first survey questions 208 include any subset of survey results provided in Table 1. For brevity, all possible combinations of the survey questions 208, 212 provided in Table 1 are not specifically delineated here. However, the skilled artisan will easily be able to envision any particular subset of the survey questions 208, 212 provided in Table 1. Likewise, the skilled artisan may know of other survey questions, not provided in Table 1, that may be combined with any subset of the survey questions provided in Table 1 to form the first survey questions used in the methods described herein.

In some embodiments, the first and/or second survey is conducted by transmitting a plurality of questions to the subject, e.g., some or all of the survey questions, and receiving answers to the plurality of survey questions before applying any of the answers to respective filters. For example, with reference to the workflow in FIG. 7, the device transmits questions relating to all of the filters of the first category class, all of the filters of the second category class, or all of the filters in the workflow (e.g., as a virtual survey where all of the questions are displayed in a single user interface, or as a series of questions displayed in consecutive user interfaces). After receiving answers to all of the survey questions, the device then applies the answers to all of the filters (e.g., sequentially or concurrently) to determine whether the subject is qualified to receive provision of the dihydropyridine-type calcium channel blocker pharmaceutical composition. In alternative embodiments, the device transmits questions relating to just those filters of the first category class for which it could not obtain answers to the questions from an electronic database associated with the subject, such as electronic health record of the subject, and just those filters of the second category class it could not obtain answers to the questions from an electronic database associated with the subject (e.g., as a virtual survey where such unanswered questions are displayed in a single user interface, or as a series of questions displayed in consecutive user interfaces). After receiving answers to all of the survey questions, the device then applies the answers to all of the filters (e.g., sequentially or concurrently) to determine whether the subject is qualified to receive provision of the dihydropyridine-type calcium channel blocker pharmaceutical composition.

In some embodiments, the first and/or second survey is conducted in a serial fashion, e.g., by transmitting a first question or a first group of survey questions (e.g., associated with a single filter) to the subject, receiving an answer to the single survey question or small group of survey questions, and applying the answer or answers to a filter, prior to transmitting a second question or second group of questions to the subject. For example, with reference to the workflow in FIG. 7, in some embodiments the device transmits a first question to the subject, relating to the pregnancy and/or breastfeeding status of the subject (e.g., question 502 'Are you or do you plan to become pregnant? Are you breastfeeding or planning to breastfeed?' in FIG. 5A). After receiving the answer to the survey question (e.g., 'yes or no'), the device applies the answer to a first pregnancy filter (705). If the first pregnancy filter is fired (e.g., in response to a "yes" answer), the device terminates (795-1) the process, and optionally provides the user with a message relating to why they are being denied a provision of the dihydropyridine-type calcium channel blocker pharmaceutical composition (e.g., as illustrated in FIG. 5B, message 504, advising the subject that taking the dihydropyridine-type calcium channel blocker pharmaceutical composition creates a risk for the fetus/baby), a suggestion for following-up with a medical professional (e.g., as illustrated in FIG. 7A, when the survey answers indicate that the subject is in hypertensive crisis (715-5), the device terminates the process (795-6) and advises that the subject seek immediate medical attention), and/or a suggestion to make a lifestyle change (e.g., as illustrated in FIG. 7A, when the survey answers indicate that the subject has slightly elevated blood pressure (715-2), the device terminates the process (795-3) and advises that the subject improve their diet or exercise routine which is consistent with current blood pressure treatment guidelines), to treat or manage their blood pressure.

In some embodiments, the first survey includes questions that elicit responses providing some or all of the characteristics listed in Table 1. In some embodiments, the survey includes questions corresponding to each of the survey results required for the methods described herein. In other embodiments, the survey includes questions corresponding to only a subset of the survey results required for the methods described herein. In such embodiments, the other survey results required for the methods described herein are acquired through other means (e.g., upon registration/subscription for a service associated with qualifying the subject for over-the-counter medication, from a healthcare provider, from a prior survey, from a database associated with a pharmacy, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a last cholesterol or blood pressure measurement determined for the subject). The same applies to the second survey 210 and corresponding results applied to the first survey 206.

Blocks 418-452. Referring to block 418 of FIG. 4B, all or a portion of the first survey results are run against a first plurality of filters of a first category class 214. As previously described, the first plurality of filters comprises a subset of filters 216 of the first filter category class 214. When a respective filter in the first plurality of filters is fired (e.g., when a survey result indicates that a triggering condition 218 has been met), the subject is deemed not qualified for delivery of the dihydropyridine-type calcium channel blocker pharmaceutical composition and the method is terminated without delivery of the dihydropyridine-type calcium channel blocker pharmaceutical composition.

In some embodiments, e.g., when the method is terminated without delivery of the dihydropyridine-type calcium channel blocker pharmaceutical composition, the subject is prevented from attempting to requalify for the dihydropyridine-type calcium channel blocker pharmaceutical composition for a predetermined period of time. This prevents the subject from abusing the systems and methods of the present disclosure.

Referring to blocks 420-452, specific filters 216 in the first plurality of filters and their exemplary triggering conditions 218 that cause the corresponding filter to fire are detailed.

In some embodiments, the first plurality of filters of the first category class 214 includes some or all of the filters 216 listed in Table 2. For example, in some embodiments, the first plurality of filters results includes 2, 3, 4, or all 5 of the filters listed in Table 2.

TABLE 2

Exemplary First Plurality of Filters of the First Category Class

| Filter | Exemplary Criteria |
| --- | --- |
| 1a | a pregnancy filter |
| 2a | a dihydropyridine medication filter |
| 3a | a blood pressure filter |
| 4a | an age filter |
| 5a | a pooled cohort equation filter |

In one embodiment, the first plurality of filters includes at least filters 1a-5a as provided in Table 2. In another embodiment, the first plurality of filters includes at least filters 1a, 2a, 3a, and 4a as provided in Table 2. In another embodiment, the first plurality of filters includes at least filters Ta, 2a, 3a, and 5a as provided in Table 2. In another embodiment, the first plurality of filters includes at least filters Ta, 2a, 4a, and 5a as provided in Table 2. In another embodiment, the first plurality of filters includes at least filters Ta, 3a, 4a, and 5a as provided in Table 2. In another embodiment, the first plurality of filters includes at least filters 2a, 3a, 4a, and 5a as provided in Table 2. In another embodiment, the first plurality of filters includes at least filters 1a, 2a, and 3a as provided in Table 2. In another embodiment, the first plurality of filters includes at least filters 1a, 2a, and 4a as provided in Table 2. In another embodiment, the first plurality of filters includes at least filters 1a, 3a, and 5a as provided in Table 2. In another embodiment, the first plurality of filters includes at least filters 2a, 3a, and 4a as provided in Table 2. In another embodiment, the first plurality of filters includes at least filters 1a and 2a as provided in Table 2. In another embodiment, the first plurality of filters includes at least filters 1a and 3a as provided in Table 2. In another embodiment, the first plurality of filters includes at least filters 1a and 4a as provided in Table 2. In another embodiment, the first plurality of filters includes at least filters 1a and 5a as provided in Table 2. In another embodiment, the first plurality of filters includes at least filters 2a and 3a as provided in Table 2. In another embodiment, the first plurality of filters includes at least filters 2a and 4a as provided in Table 2. In another embodiment, the first plurality of filters includes at least filters 2a and 5a as provided in Table 2. In another embodiment, the first plurality of filters includes at least filters 3a and 4a as provided in Table 2. In another embodiment, the first plurality of filters includes at least filters 3a and 5a as provided in Table 2. In another embodiment, the first plurality of filters includes at least filters 4a and 5a as provided in Table 2.

It is contemplated that, in some embodiments, any one or more of the filters 216 provided in Table 2 will not be included in the first plurality of filters. For example, in some embodiments, a characteristic associated with a particular survey result will be informative when qualifying a subject for one particular dihydropyridine-type calcium channel blocker but not for another dihydropyridine-type calcium channel blocker.

Accordingly, it is contemplated that the first plurality of filters includes any sub-set of filters 216 provided in Table 2. Likewise, the skilled artisan may know of other filters 216, not provided in Table 2, which may be combined with any subset of the filters 216 provided in Table 2 to form the first plurality of filters results used in the methods described herein. For brevity, all possible combinations of the filters 216 provided in Table 2 are not specifically delineated here.

Referring to blocks 420-422, in some embodiments the first plurality of filters comprises a pregnancy filter (e.g., first pregnancy filter 216-1 in FIG. 3 and/or filter 1a in Table 2). In some embodiments, the pregnancy filter is configured to be fired at least when the first plurality of survey results indicates that the subject is pregnant or the subject is breastfeeding. In some embodiments, the pregnancy filter is also configured to be fired when the subject is planning on becoming pregnant. When the pregnancy filter is fired, the subject is not permitted to obtain the dihydropyridine-type calcium channel blocker pharmaceutical composition over-the-counter (e.g., the method is terminated without authorizing provision of the dihydropyridine-type calcium channel blocker pharmaceutical composition to the subject). For example, the device transmits prompt 502, as illustrated in FIG. 5A, to the subject and the device applies the subject's answer to the pregnancy filter. If the subject's answer indicates that they are pregnant, they are planning on being pregnant, they are breastfeeding, or they are planning to breastfeeding, the pregnancy filter is fired, and the method is terminated without authorizing provision of the dihydropyridine-type calcium channel blocker pharmaceutical composition to the subject. In some embodiments, the device transmits a message explaining why authorization was denied, e.g., message 504 illustrated in FIG. 5B.

Referring to blocks 424-426, in some embodiments the first plurality of filters comprises a dihydropyridine medication filter (e.g., dihydropyridine medication filter 216-2 in FIG. 3 and/or filter 2a in Table 2). The dihydropyridine medication filter is configured to be fired at least when the first plurality of survey results indicates that the subject is taking (e.g., has a prescription for) a dihydropyridine-type calcium channel blocker. In some embodiments, the dihydropyridine medication filter is fired when the first plurality of survey results indicate that the subject is taking one or more of amlodipine, isradipine, nisoldipine, or nifedipine. If the dihydropyridine medication filter is fired, the subject is not permitted to obtain the dihydropyridine-type calcium channel blocker pharmaceutical composition pharmaceutical composition over-the-counter (e.g., the method is terminated without authorizing provision of the dihydropyridine-type calcium channel blocker pharmaceutical composition to the subject).

Referring to blocks 428-438 of FIGS. 4B and 4C, in some embodiments the first plurality of filters comprises a first blood pressure filter (e.g., first blood pressure filter 216-3 in FIG. 3 and/or filter 3a in Table 2). The first blood pressure filter is configured to be fired at least when the first plurality of survey results indicates that the subject has normal blood pressure (e.g., a systolic blood pressure less than 120 mm Hg and a diastolic blood pressure less than 80 mm Hg) or the subject has hypertension stage 2 (e.g., a systolic blood pressure greater than or equal to 140 mm Hg or a diastolic blood pressure greater than or equal to 90 mm Hg). If the blood pressure filter is fired, the subject is not permitted to obtain the dihydropyridine-type calcium channel blocker pharmaceutical composition over-the-counter (e.g., the method is terminated without authorizing provision of the dihydropyridine-type calcium channel blocker pharmaceutical composition to the subject).

In some embodiments, the first blood pressure filter is fired when the first plurality of survey results indicates that the systolic blood pressure of the subject is greater than a ceiling systolic pressure, the diastolic blood pressure of the subject is greater than a ceiling diastolic pressure, or the systolic blood pressure of the subject is less than a floor systolic pressure and the diastolic blood pressure of the subject is less than a floor diastolic pressure. In some embodiments, the ceiling systolic pressure is 139 mm Hg, the ceiling diastolic pressure is 89 mm Hg, the floor systolic pressure is 130 mm Hg, and the floor diastolic pressure is 80 mm Hg. In some embodiments, the ceiling systolic pressure is 140 mm Hg, the ceiling diastolic pressure is 90 mm Hg, the floor systolic pressure is 129 mm Hg, and the floor diastolic pressure is 79 mm Hg. In some embodiments, the blood pressure cutoffs defining when the blood pressure filter is fired and when the blood pressure filter is not fired are set according to a set of healthcare guidelines, which may change over time, and/or vary on a jurisdiction-by-jurisdiction basis. For example, in the United States, the American College of Cardiology and the American Heart Association collaborated to provide guidance on management of high blood pressure. Whelton P K, et al., J Am Coll Cardiol., S0735-1097(17)41519-1 (2017), the contents of which are hereby expressly incorporated by reference. These guidelines change over time as medical research and advances in treatment better inform management of high blood pressure.

In some embodiments, e.g., when the first plurality of survey results indicate that the subject has elevated blood pressure but is not hypertensive (e.g., a systolic blood pressure in between 120 and 129 mm Hg and a diastolic blood pressure less than 80 mm Hg), the first blood pressure filter is fired, and advice is transmitted to the subject to manage their blood pressure by eating healthy and exercising. In some embodiments, e.g., when the first plurality of survey results indicate that the subject has hypertension stage two (e.g., a systolic blood pressure greater than or equal to 140 mm Hg or a diastolic blood pressure greater than or equal to 90 mm Hg), the first blood pressure filter is fired and advice is transmitted to the subject to visit a doctor to discuss taking a prescription-strength blood pressure medication. In some embodiments, e.g., when the first plurality of survey results indicate that the subject is in hypertension crisis (e.g., a systolic blood pressure greater than 180 mm Hg and/or a diastolic blood pressure greater than 120 mm Hg), the first blood pressure filter is fired, and advice is transmitted to the subject to seek emergency medical attention.

Referring to blocks 440-442 of FIG. 4C, in some embodiments the first plurality of filters comprises an age filter (e.g., age filter 216-4 in FIG. 3 and/or filter 4a in Table 2). In some embodiments, the age filter is fired when the first plurality of survey results indicates that the subject is less than eighteen years old. If the age filter is fired, the subject is not permitted to obtain the dihydropyridine-type calcium channel blocker pharmaceutical composition pharmaceutical composition over-the-counter (e.g., the method is terminated without authorizing provision of the dihydropyridine-type calcium channel blocker pharmaceutical composition to the subject).

In some embodiments, the age filter is fired when the first plurality of survey results indicates that the subject has an age for which a risk of an atherosclerotic cardiovascular disease (ASCVD) event cannot be calculated according to a predictive algorithm (e.g., a 10-year risk estimate for a hard ASCVD event using the pooled cohort equations provided in Goff, D C Jr. et al., Circulation (2013). For example, in some embodiments, the age filter is fired when the first plurality of survey results indicates that the subject is less than forty years old, which would provide an incalculable risk using the equations in Goff et al.

Referring to blocks 444-452, in some embodiments the first plurality of filters comprises a pooled cohort equation filter (e.g., pooled cohort equation filter 216-5 in FIG. 3 and/or filter 5a in Table 2). In some embodiments the pooled cohort equation filter incorporates the gender of the subject, the race of the subject, the age of the subject, the blood pressure medication status of the subject, the total cholesterol level of the subject, the HDL cholesterol count of the subject, the systolic blood pressure of the subject, the smoking status of the subject (e.g., whether the subject currently smokes or has smoked in the past), and the diabetes status of the subject (e.g., whether the subject has Type-1 diabetes, Type-2 diabetes, etc.) to derive a risk for atherosclerotic cardiovascular disease (e.g., a risk for experiencing an atherosclerotic cardiovascular disease (ASCVD) event within a certain timeframe, such as five or ten years). In some embodiments, the pooled cohort equation also incorporates a familial history of premature heart or stroke (e.g., a history of heart attack or stroke before the age of forty-five, fifty, fifty-five, sixty, etc.). In some embodiments, the pooled cohort equation incorporates a high sensitive quantification of c-reactive protein (hsCRP) level of the subject. If the pooled cohort equation filter is fired, the subject is not permitted to obtain the dihydropyridine-type calcium channel blocker pharmaceutical composition pharmaceutical composition over-the-counter (e.g., the method is terminated without authorizing provision of the dihydropyridine-type calcium channel blocker pharmaceutical composition to the subject).

In some embodiments, the first pooled cohort equation filter is configured to be fired at least when the first plurality of survey results indicates that, despite having hypertension stage 1 (e.g., a systolic blood pressure of 130 to 139 mm HG or a diastolic blood pressure of 80 to 89 mm Hg) the subject has a risk for atherosclerotic disease that falls below a minimum risk threshold (e.g., the subject does not have a high enough risk of having an ASCVD event to justify taking a dihydropyridine-type calcium channel blocker pharmaceutical composition). In some embodiments, the risk for the atherosclerotic cardiovascular disease calculated using the pooled cohort equation is a lifetime risk, a 5-year risk, or a 10-year risk. In some embodiments, the pooled cohort equation is implemented as a multivariable Cox proportional hazard regression.

In some embodiments, the pooled cohort equation filter is fired at least when the first survey results indicate the subject has a 10-year risk for atherosclerotic cardiovascular disease (e.g., a 10-year risk of experiencing an atherosclerotic cardiovascular disease (ASCVD) event) that is less than 10%, as determined by the pooled cohort equation. In some embodiments, the first pooled cohort equation filter is also configured to be fired when one or more value provided by the subject does not enable the pooled cohort equation to calculate an ASCVD event risk for the subject (e.g., a subject age of less than forty would provide an incalculable risk using the equations in Goff et al.). In some embodiments, the pooled cohort equation filter behaves as a filter of the second category class when a value provided by the subject does not enable the pooled cohort equation to calculate an ASCVD event risk. E.g., when the pooled cohort equation filter is fired for receiving a value that is out of a range of values required to calculate an ASCVD event risk, the device issues a warning to the subject (e.g., requiring the subject discuss taking a dihydropyridine-type calcium channel blocker pharmaceutical composition with a medical professional) that must be acknowledged prior to being authorized to receive a provision of the dihydropyridine-type calcium channel blocker pharmaceutical composition, rather than automatically terminating the process, as would be done when a filter of the first category class is filtered. In some embodiments, the pooled cohort equation filter is fired when the first survey results indicate the subject is younger than forty years old.

The pooled cohort equation estimates the probability of incurring a hard atherosclerotic cardiovascular disease (ASCVD) event in a given period of time, such as in the next 5 years, the next 10 years, or in the lifetime of a subject. In some embodiments, the pooled cohort equation for the pooled cohort equation filter is calculated using the guidelines set forth in Goff, D C Jr, et al., J. Am. Coll. Cardiol., 63:2935-59 (2014), the content of which is hereby incorporated by reference. Following the Goff et al. (Id.) calculation of the 10-year risk estimate for a hard ASCVD event using the pooled cohort equations is done as a series of steps. The natural log of the age of the subject, total cholesterol, HDL-C, and systolic blood pressure are first calculated with the systolic blood pressure being either a treated or untreated value. For example, calculation of the pooled cohort equations estimate the probability of a Caucasian male subject 55 years of age with total cholesterol 213 mg/dL, HDL-C 50 mg/dL, untreated systolic blood pressure 120 mm Hg, nonsmoker, and without diabetes determine the probability of a hard ASCVD event in the next 10 years using Goff Id. begins by first taking the natural log of the subject's age (4.01), the natural log of the subject's total cholesterol (5.36), the natural log of the subject's HDL-C (3.91), and the natural log of the subject's systolic blood pressure (4.79). These values are then multiplied by the coefficients from the equation ("Coefficient" column of Table A of Goff Id.) for the specific race-sex group of the individual to obtain "coefficient x values." That is:

multiply the natural log of the subject's age (4.01) by the coefficient 12.344 to obtain the "coefficient x value" of 49.47, multiply the natural log of the subject's total cholesterol (5.36) by the coefficient 11.853 to obtain the "coefficient x value" of 63.55, multiply the natural log of the subject's HDL-C (3.91) by the coefficient −7.990 to obtain the "coefficient x value" of −31.26, and multiply the natural log of the subject's systolic blood pressure (4.79) by the coefficient 1.764 to obtain the "coefficient x value" of 8.45.

Any appropriate interaction terms are also calculated. Following Goff Id., in the case of the Caucasian male subject 55 years of age, the interaction terms are:

the Log Age (4.01) X Log total Cholesterol (5.36) multiplied by the coefficient −2.664 to obtain the "coefficient x value" of −57.24 and Log Age (4.01) X Log HDL-C (3.91) multiplied by the coefficient 1.769 to obtain the "coefficient x value" of 27.73.

The sum of these "coefficient x values" is then calculated for the individual (49.47+63.55−31.26+8.45−57.24+27.73=60.69). The estimated 10-year risk of a first hard ASCVD event is formally calculated as 1 minus the baseline survival rate at 10 years for the sex/race (in this example Caucasian male), raised to the power of the exponent of the "Coefficient x Value" sum calculated above minus the race (Caucasian) and sex (Male) specific overall mean "Coefficient x Value" sum; or, in equation form:

$$1-0.9144^{e^{(60.69-61.18)}}$$

where the number 0.9144 is the baseline survival rate at 10 years for Caucasian males from Goff Id., the number 60.69 is the "coefficient x value" calculated for the particular subject as detailed above, and the number 61.18 is the race (Caucasian) and sex (Male) specific overall mean "Coefficient x Value" from Goff Id. This equates to a 5.3% probability of a first hard ASCVD event within 10 years.

In some embodiments, the pooled cohort equation filter incorporates some or all of the characteristics listed in Table 7, e.g., as determined from a set of survey results, to derive a subject risk for atherosclerotic cardiovascular disease. For example, in some embodiments, the first plurality of survey results includes 2, 3, 4, 5, 6, 7, 8, 9, 10, or all 11 of the characteristics listed in Table 7. The pooled cohort equation filter is fired when the subject's risk for atherosclerotic cardiovascular disease exceeds a threshold level of risk.

TABLE 7

Exemplary Characteristics Used for Pooled Cohort Equation Filter

| Result | Exemplary Characteristics |
|---|---|
| 1 | a gender of the subject |
| 2 | an age of the subject |
| 3 | a total cholesterol level of the subject |
| 4 | a HDL cholesterol count of the subject |
| 5 | a systolic blood pressure of the subject |
| 6 | a race of the subject |
| 7 | whether the subject is taking one or more medications for hypertension |
| 8 | a smoking status of the subject |
| 9 | a diabetes status of the subject |
| 10 | whether the subject has a family history of heart or stroke before the age of 60 |
| 11 | a hsCRP level of the subject |

In one embodiment, the pooled cohort equation filter incorporates at least survey results 1-9 as provided in Table 7. In another embodiment, the first survey results include at least survey results 1-10 as provided in table 7. In another embodiment, the first survey results include at least survey results 1-9 and 11 as provided in Table 7. In another embodiment, the first survey results include at least survey results 1-11 as provided in Table 7.

In some embodiments, the pooled cohort equation used to calculate a risk of fatal cardiovascular disease for the pooled cohort equation filter is calculated using the guidelines set forth in Perk J. et al., European Guidelines on cardiovascular disease prevention in clinical practice, European Heart Journal 33:1635-1701 (2012), which is hereby incorporated by reference herein. In some embodiments, the pooled cohort equation filter follows a low CVD risk SCORE chart, which incorporates the sex of the subject, the age of the subject, the total cholesterol level of the subject, the systolic blood pressure of the subject, and a smoking status of the subject, as set forth in Perk J. et al., Supra. In some embodiments, the pooled cohort equation filter follows a high CVD risk SCORE chart, which incorporates the sex of the subject, the age of the subject, the total cholesterol level of the subject, the systolic blood pressure of the subject, and a smoking status of the subject, as set forth in Perk J. et al., Supra. In some embodiments, a conversion factor is used to convert a risk of fatal cardiovascular disease to a risk of fatal plus nonfatal hard cardiovascular disease events, as set forth in Catapano A L et al., 2016 ESC/EAS Guidelines for the Management of Dyslipidaemias. Eur Heart J. 2016 Oct. 14; 37(39):2999-3058, which is hereby incorporated by reference herein.

In some embodiments, using the SCORE guidelines, the risk for the fatal cardiovascular disease used in calculating the pooled cohort equation is a 10-year risk, and a first threshold value, e.g., a threshold value which when the risk of the subject is determined to be less than fires the filter, is a 3% risk. In some embodiments. In some embodiments, the risk for the fatal cardiovascular disease used in calculating the pooled cohort equation is a 10-year risk, and the first threshold value is a 5% risk. In some embodiments, the risk for the fatal cardiovascular disease used in calculating the pooled cohort equation is a 10-year risk, and a second threshold value, e.g., a threshold value which when the risk of the subject is determined to be greater than fires the filter, is a 4% risk. In some embodiments, the risk for the fatal cardiovascular disease used in calculating the pooled cohort equation is a 10-year risk, and the second threshold value is a 9% risk. In some embodiments, the risk for the fatal cardiovascular disease used in calculating the pooled cohort equation is a 10-year risk, and the second threshold value is a 14% risk. In some embodiments, the risk for the fatal cardiovascular disease used in calculating the pooled cohort equation is a 10-year risk, and a threshold range, e.g., a threshold range which when the subject is determined to have a risk above or below the range fires the filter, is a 2-14% risk. In some embodiments, the risk for the fatal cardiovascular disease used in calculating the pooled cohort equation is a 10-year risk, and the threshold range is a 3-14% risk. In some embodiments, the risk for the fatal cardiovascular disease used in calculating the pooled cohort equation is a 10-year risk, and the threshold range is a 5-14% risk. In some embodiments, the risk for the fatal cardiovascular disease used in calculating the pooled cohort equation is a 10-year risk, and the threshold range is a 10-14% risk. In some embodiments, the risk for the fatal cardiovascular disease used in calculating the pooled cohort equation is a 10-year risk, and the threshold range is a 2-9% risk. In some embodiments, the risk for the fatal cardiovascular disease used in calculating the pooled cohort equation is a 10-year risk, and the threshold range is a 3-9% risk. In some embodiments, the risk for the fatal cardiovascular disease used in calculating the pooled cohort equation is a 10-year risk, and the threshold range is a 5-9% risk. In some embodiments, the risk for the fatal cardiovascular disease used in calculating the pooled cohort equation is a 10-year risk, and the threshold range is a 2-4% risk. In some embodiments, the risk for the fatal cardiovascular disease used in calculating the pooled cohort equation is a 10-year risk, and the threshold range is a 3-4% risk. In some embodiments, the risk for the fatal cardiovascular disease used in calculating the pooled cohort equation is a 10-year risk, and the threshold range is a 2-3% risk. In some embodiments, lipid lowering therapy is not indicated, e.g., a filter of the second class type is fired, when it is determined the subject has less than a 5% ten-year risk of fatal cardiovascular disease.

In some embodiments, the pooled cohort equation used to calculate a risk of a cardiovascular disease-related death for the pooled cohort equation filter is calculated using the guidelines set forth in Teramoto et al., Japan Atherosclerosis Society. Executive summary of the Japan Atherosclerosis Society (JAS) guidelines for the diagnosis and prevention of atherosclerotic cardiovascular diseases in Japan-2012 version, J Atheroscler Thromb., 2013; 20(6):517-23, which is hereby incorporated by reference herein. In some embodiments, the pooled cohort equation filter follows the NIPPON DATA80 absolute risk assessment charts, which incorporate the sex of the subject, the age of the subject, the total cholesterol level of the subject, the systolic blood pressure of the subject, and a smoking status of the subject, as set forth in Teramoto et al., Supra. In some embodiments, the pooled cohort equation also incorporates a glucose level of the subject.

In some embodiments, using the NIPPON DATA80 guidance, the risk for the coronary artery death used in calculating the pooled cohort equation is a 10-year risk, and a first threshold value, e.g., a threshold value which when the risk of the subject is determined to be less than fires the filter, is a 0.5% risk. In some embodiments, the risk for the fatal cardiovascular disease used in calculating the pooled cohort equation is a 10-year risk, and the first threshold value is a 1% risk. In some embodiments, the risk for the fatal cardiovascular disease used in calculating the pooled cohort equation is a 10-year risk, and the first threshold value is a 2% risk. In some embodiments, the risk for the fatal cardiovascular disease used in calculating the pooled cohort equation is a 10-year risk, and a second threshold value, e.g., a threshold value which when the risk of the subject is determined to be greater than fires the filter, is a 1% risk. In some embodiments, the risk for the fatal cardiovascular disease used in calculating the pooled cohort equation is a 10-year risk, and the second threshold value is a 2% risk. In some embodiments, the risk for the fatal cardiovascular disease used in calculating the pooled cohort equation is a 10-year risk, and the second threshold value is a 5% risk. In some embodiments, the risk for the fatal cardiovascular disease used in calculating the pooled cohort equation is a 10-year risk, and the second threshold value is a 10% risk. In some embodiments, the risk for the fatal cardiovascular disease used in calculating the pooled cohort equation is a 10-year risk, and a threshold range, e.g., a threshold range which when the subject is determined to have a risk above or below the range fires the filter, is a 0.5-10% risk. In some embodiments, the risk for the fatal cardiovascular disease used in calculating the pooled cohort equation is a 10-year risk, and the threshold range is a 1-10% risk. In some embodiments, the risk for the fatal cardiovascular disease used in calculating the pooled cohort equation is a 10-year risk, and the threshold range is a 2-10% risk. In some embodiments, the risk for the fatal cardiovascular disease used in calculating the pooled cohort equation is a 10-year risk, and the threshold range is a 5-10% risk. In some embodiments, the risk for the fatal cardiovascular disease used in calculating the pooled cohort equation is a 10-year risk, and the threshold range is a 0.5-5% risk. In some embodiments, the risk for the fatal cardiovascular disease used in calculating the pooled cohort equation is a 10-year risk, and the threshold range is a 1-5% risk. In some embodiments, the risk for the fatal cardiovascular disease used in calculating the pooled cohort equation is a 10-year risk, and the threshold range is a 2-5% risk. In some embodiments, the risk for the fatal cardiovascular disease used in calculating the pooled cohort equation is a 10-year risk, and the threshold range is a 0.5-2% risk. In some embodiments, the risk for the fatal cardiovascular disease used in calculating the pooled cohort equation is a 10-year risk, and the threshold range is a 1-2% risk. In some embodiments, the risk for the fatal cardiovascular disease used in calculating the pooled cohort equation is a 10-year risk, and the threshold range is a 0.5-1% risk.

In some embodiments, the pooled cohort equation used to calculate a risk of atherosclerotic cardiovascular disease for the pooled cohort equation filter is calculated using the guidelines set forth in Yang X. et al., Predicting the 10-Year Risks of Atherosclerotic Cardiovascular Disease in Chinese Population: The China-PAR Project (Prediction for ASCVD Risk in China). Circulation. 2016 Nov. 8; 134(19):1430-1440, which is hereby incorporated by reference herein. In some embodiments, the pooled cohort equation filter follows the China-PAR gender specific equations, which incorporate the sex of the subject (e.g., to determine which equation to use), the age of the subject, the systolic blood pressure of the subject, a blood pressure treatment status of the subject, the total cholesterol level of the subject, a smoking status of the subject, a diabetes mellitus status of the subject, the waist circumference of the subject, a geographic residential-region of the subject (e.g., for Chinese residents only, either northern China or southern China), an urbanization residential-region of the subject (e.g., for men residing in China only, either urban or rural), and family history of atherosclerotic cardiovascular disease (e.g., for men only), as set forth in Yang X. et al., Supra and at Supplemental Information. In some embodiments, the pooled cohort equation also incorporates an HDL cholesterol level of the subject and/or a cholesterol treatment status of the subject.

In some embodiments, using the China-PAR guidance, the risk for the atherosclerotic cardiovascular disease used in calculating the pooled cohort equation is a 10-year risk, and a first threshold value, e.g., a threshold value which when the risk of the subject is determined to be less than fires the filter, is a 5% risk. In some embodiments, the risk for the atherosclerotic cardiovascular disease used in calculating the pooled cohort equation is a 10-year risk, and the first threshold value is a 7.5% risk. In some embodiments, the risk for the atherosclerotic cardiovascular disease used in calculating the pooled cohort equation is a 10-year risk, and a second threshold value, e.g., a threshold value which when the risk of the subject is determined to be greater than fires the filter, is a 7.5% risk. In some embodiments, the risk for the atherosclerotic cardiovascular disease used in calculating the pooled cohort equation is a 10-year risk, and the second threshold value is a 10% risk. In some embodiments, the risk for the atherosclerotic cardiovascular disease used in calculating the pooled cohort equation is a 10-year risk, and a threshold range, e.g., a threshold range which when the subject is determined to have a risk above or below the range fires the filter, is a 5-10% risk. In some embodiments, the risk for the atherosclerotic cardiovascular disease used in calculating the pooled cohort equation is a 10-year risk, and the threshold range is a 7.5-10% risk. In some embodiments, the risk for the atherosclerotic cardiovascular disease used in calculating the pooled cohort equation is a 10-year risk, and the threshold range is a 5-7.5% risk.

In some embodiments, the pooled cohort equation used to calculate a risk of atherosclerotic cardiovascular disease for the pooled cohort equation filter 222-2 is calculated using the guidelines set forth in National Vascular Disease Prevention Alliance, Guidelines for the management of absolute cardiovascular disease risk, 2012, which is hereby incorporated by reference herein. In some embodiments, the pooled cohort equation filter follows the Australian cardiovascular risk charts, which incorporate the sex of the subject, the age of the subject, the systolic blood pressure of the subject, the ratio of total cholesterol to HDL levels of the subject, and a smoking status of the subject, as set forth in Absolute cardiovascular disease risk management: Quick reference guide for health professionals, 2012, National Stroke Foundation. In some embodiments, the pooled cohort equation also incorporates the decent of the subject (e.g., in Australia only, for Aboriginal, Torres Strait Islander, or other populations).

In some embodiments, using the Australian cardiovascular risk charts, the risk for the atherosclerotic cardiovascular disease used in calculating the pooled cohort equation is a 5-year risk, and a first threshold value, e.g., a threshold value which when the risk of the subject is determined to be less than fires the filter, is a 5% risk. In some embodiments, the risk for the atherosclerotic cardiovascular disease used in calculating the pooled cohort equation is a 5-year risk, and the first threshold value is a 10% risk. In some embodiments, the risk for the atherosclerotic cardiovascular disease used in calculating the pooled cohort equation is a 5-year risk, and the first threshold value is a 16% risk. In some embodiments, the risk for the atherosclerotic cardiovascular disease used in calculating the pooled cohort equation is a 5-year risk, and the first threshold value is a 20% risk. In some embodiments, the risk for the atherosclerotic cardiovascular disease used in calculating the pooled cohort equation is a 5-year risk, and the first threshold value is a 25% risk. In some embodiments, the risk for the atherosclerotic cardiovascular disease used in calculating the pooled cohort equation is a 5-year risk, and a second threshold value, e.g., a threshold value which when the risk of the subject is determined to be greater than fires the filter, is a 30% risk. In some embodiments, the risk for the atherosclerotic cardiovascular disease used in calculating the pooled cohort equation is a 5-year risk, and the second threshold value is a 25% risk. In some embodiments, the risk for the atherosclerotic cardiovascular disease used in calculating the pooled cohort equation is a 5-year risk, and the second threshold value is a 20% risk. In some embodiments, the risk for the atherosclerotic cardiovascular disease used in calculating the pooled cohort equation is a 5-year risk, and the second threshold value is a 16% risk. In some embodiments, the risk for the atherosclerotic cardiovascular disease used in calculating the pooled cohort equation is a 5-year risk, and the second threshold value is a 10% risk. In some embodiments, the risk for the atherosclerotic cardiovascular disease used in calculating the pooled cohort equation is a 5-year risk, and the second threshold value is a 5% risk. In some embodiments, the risk for the atherosclerotic cardiovascular disease used in calculating the pooled cohort equation is a 5-year risk, and a threshold range, e.g., a threshold range which when the subject is determined to have a risk above or below the range fires the filter, is a 5-30% risk. In some embodiments, the risk for the atherosclerotic cardiovascular disease used in calculating the pooled cohort equation is a 5-year risk, and the threshold range is a 10-30% risk. In some embodiments, the risk for the atherosclerotic cardiovascular disease used in calculating the pooled cohort equation is a 5-year risk, and the threshold range is a 16-30% risk. In some embodiments, the risk for the atherosclerotic cardiovascular disease used in calculating the pooled cohort equation is a 5-year risk, and the threshold range is a 20-30% risk. In some embodiments, the risk for the atherosclerotic cardiovascular disease used in calculating the pooled cohort equation is a 5-year risk, and the threshold range is a 25-30% risk. In some embodiments, the risk for the atherosclerotic cardiovascular disease used in calculating the pooled cohort equation is a 5-year risk, and the threshold range is a 5-25% risk. In some embodiments, the risk for the atherosclerotic cardiovascular disease used in calculating the pooled cohort equation is a 5-year risk, and the threshold range is a 10-25% risk. In some embodiments, the risk for the atherosclerotic cardiovascular disease used in calculating the pooled cohort equation is a 5-year risk, and the threshold range is a 16-25% risk. In some embodiments, the risk for the atherosclerotic cardiovascular disease used in calculating the pooled cohort equation is a 5-year risk, and the threshold range is a 20-25% risk. In some embodiments, the risk for the atherosclerotic cardiovascular disease used in calculating the pooled cohort equation is a 5-year risk, and the threshold range is a 5-20% risk. In some embodiments, the risk for the atherosclerotic cardiovascular disease used in calculating the pooled cohort equation is a 5-year risk, and the threshold range is a 10-20% risk. In some embodiments, the risk for the atherosclerotic cardiovascular disease used in calculating the pooled cohort equation is a 5-year risk, and the threshold range is a 16-20% risk. In some embodiments, the risk for the atherosclerotic cardiovascular disease used in calculating the pooled cohort equation is a 5-year risk, and the threshold range is a 5-16% risk. In some embodiments, the risk for the atherosclerotic cardiovascular disease used in calculating the pooled cohort equation is a 5-year risk, and the threshold range is a 10-16% risk. In some embodiments, the risk for the atherosclerotic cardiovascular disease used in calculating the pooled cohort equation is a 5-year risk, and the threshold range is a 5-10% risk.

In some embodiments, the pooled cohort equation used to calculate a risk of atherosclerotic cardiovascular disease for the pooled cohort equation filter 222-2 is calculated using the guidelines set forth in Anderson T J et al., 2016 Canadian Cardiovascular Society Guidelines for the Management of Dyslipidemia for the Prevention of Cardiovascular Disease in the Adult, Can J Cardiol. 2016 November; 32(11):1263-1282, which is hereby incorporated by reference herein. In some embodiments, the pooled cohort equation filter follows a Framingham Heart Study Risk Score equation (FRS), which incorporates the sex of the subject, the age of the subject, the systolic blood pressure of the subject, a blood pressure treatment status of the subject, the total cholesterol level of the subject, and an HDL cholesterol level of the subject, a smoking status of the subject, a diabetes mellitus status of the subject, and a CVD event incident status of the subject, as set forth in D'Agostino R B Sr et al., General cardiovascular risk profile for use in primary care: the Framingham Heart Study. Circulation. 2008 Feb. 12; 117 (6):743-53, which is hereby incorporated by reference herein. In some embodiments, the pooled cohort equation filter follows a modified Framingham Heart Study Risk Score equation (FRS), which incorporates the sex of the subject, the age of the subject, the systolic blood pressure of the subject, a blood pressure treatment status of the subject, the total cholesterol level of the subject, and an HDL cholesterol level of the subject, a smoking status of the subject, a diabetes mellitus status of the subject, and a CVD event incident status of the subject, and a family history status of premature cardiovascular disease, as set forth in Anderson T J et al., Supra. In some embodiments, the pooled cohort equation filter follows a Cardiovascular Life Expectancy Model (CLEM), as set forth in Grover S A et al., Estimating the benefits of modifying risk factors of cardiovascular disease: a comparison of primary vs secondary prevention. Arch Intern Med. 1998 Mar. 23; 158(6):655-62, which is hereby incorporated by reference herein. Referring to block 428, in some embodiments, using the Canadian Cardiovascular Society guidance, the risk for the atherosclerotic cardiovascular disease used in calculating the pooled cohort equation is a 10-year risk, and a first threshold value, e.g., a threshold value which when the risk of the subject is determined to be less than fires the filter, is a 5% risk. In some embodiments, the risk for the atherosclerotic cardiovascular disease used in calculating the pooled cohort equation is a 10-year risk, and the first threshold value is a 10% risk. In some embodiments, the risk for the atherosclerotic cardiovascular disease used in calculating the pooled cohort equation is a 10-year risk, and a second threshold value, e.g., a threshold value which when the risk of the subject is determined to be greater than fires the filter, is a 20% risk. In some embodiments, the risk for the atherosclerotic cardiovascular disease used in calculating the pooled cohort equation is a 10-year risk, and the second threshold value is a 10% risk. In some embodiments, the risk for the atherosclerotic cardiovascular disease used in calculating the pooled cohort equation is a 10-year risk, and a threshold range, e.g., a threshold range which when the subject is determined to have a risk above or below the range fires the filter, is a 5-20% risk. In some embodiments, the risk for the atherosclerotic cardiovascular disease used in calculating the pooled cohort equation is a 10-year risk, and the threshold range is a 10-20% risk. In some embodiments, the risk for the atherosclerotic cardiovascular disease used in calculating the pooled cohort equation is a 10-year risk, and the threshold range is a 5-10% risk.

In some embodiments, a probability of the occurrence of a hard ASCVD event in a given period of time (e.g., within the next 10 years), e.g., as calculated above, is modified by considering one or both of the familial history of the subject for premature heart attacks or strokes and the hsCRP level of the subject. This inclusion is to reduce a likelihood of over-predicting adverse events, e.g., in subjects without a familial history of adverse events and/or with healthy hsCRP levels.

In some embodiments, e.g., when the first survey results indicate that the subject is at least 80 years old, that the subject has had an atherosclerotic cardiovascular event, or that the subject has had a heart procedure, the device bypasses the pooled cohort equation filter (e.g., even if the first plurality of survey results indicates that the subject has an ASCVD risk falling below a minimum threshold risk, or that the subject has an age rendering calculation of an ASCVD risk impossible, the pooled cohort equation filter is not fired). For example, as illustrated in FIG. 7, in response to determining that the subject has an ASCVD history (e.g., has experienced an ASCVD event or had a heart procedure) at 720 or determining that the subject is at least 80 years of age at 730, the device generates a record of an exempting condition (e.g., 760-1 or 760-2) and then, prior to applying one or more survey results to the pooled cohort equation at 765, the device determines whether an exempting condition is present at 762. If a condition is present, pooled cohort equation filter 765 is bypassed and the device proceeds to liver disease filter 770. In some embodiments, the exemption record is a record of survey result, e.g., the device pre-checks earlier recorded survey results associated with ASCVD history and age prior to proceeding with pooled cohort equation filter 765. In some embodiments, the exemption record is a record separate from the survey result that indicates the exempting condition, and the device checks for separate records indicating the presence of an exempting condition before proceeding with pooled cohort equation filter 765.

Referring to block 452 of FIG. 4D, in some embodiments the first plurality of survey results further comprises whether the subject is allergic to the dihydropyridine-type calcium channel blocker pharmaceutical composition, and the first plurality of filters includes an adverse reaction filter. The adverse reaction filter is fired when the first survey results indicate that the subject is allergic to the dihydropyridine-type calcium channel blocker pharmaceutical composition.

In some embodiments, the adverse reaction filter is fired when the first survey results indicate that the subject has developed an adverse reaction to a dihydropyridine-type calcium channel blocker medication in the past. In some embodiments, the adverse reaction filter is fired when the first survey results indicate that the subject has developed an adverse reaction to any dihydropyridine-type calcium channel blocker pharmaceutical composition in the past.

Figure 7C:
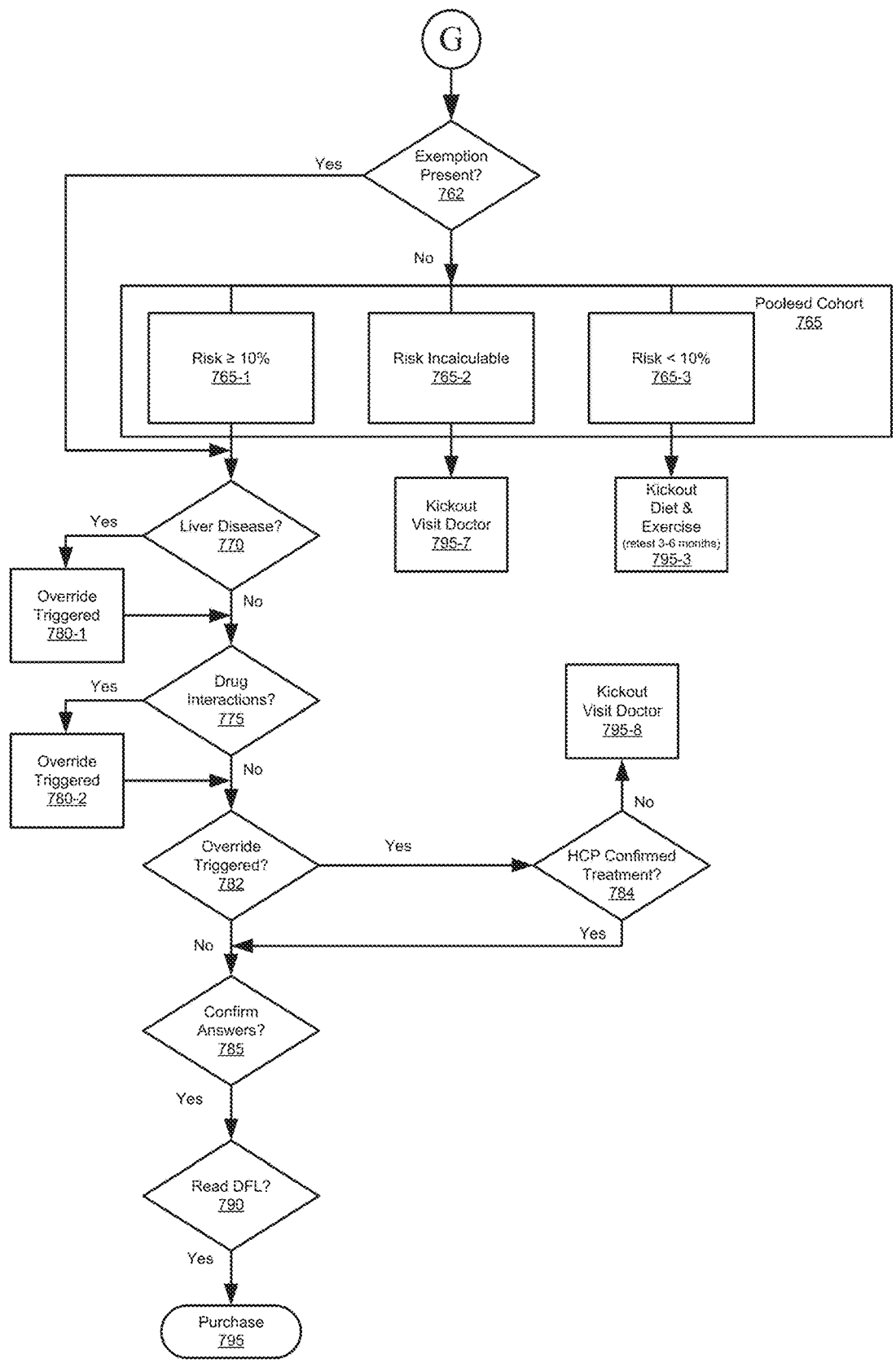

Referring to block 454 of FIG. 4D, the method also includes running all or a portion of the first survey results against a second plurality of filters of a second category class 220. When a respective filter in the second plurality of filters is fired, the subject is provided with a warning 226 corresponding to the respective filter (e.g., filter warning 228-4 corresponds to filter 222-4). In some embodiments, the warning 226 is provided as a next step, e.g., prior to applying survey results to any subsequent filters, after the corresponding filter is fired. For example, with respect to FIG. 7C, in some embodiments, e.g., when the liver disease filter is triggered at 770, the device would provide the subject with a warning prior to proceeding to the drug interaction filter at 775, e.g., requiring the subject confirm they have discussed their history of liver disease with a health care provider and the healthcare provider still recommends taking a dihydropyridine-type calcium channel blocker pharmaceutical composition. In some embodiments the warning 226 is provided after applying survey results to all subsequent filters. For example, as illustrated in FIG. 7C, in some embodiments, e.g., when the liver disease filter is triggered at 770, the device would proceed to the drug interaction filter at 775 prior to transmitting a warning to the subject, and then transmit all warnings corresponding to filters of the second category class, at 784, after survey results have been applied to all subsequent filters.

In some embodiments, the second plurality of filters 222 of the second category class 220 includes the filters listed in Table 3.

TABLE 3

Exemplary Second Plurality of Filters of the Second Category Class

| Filter | Exemplary Criteria |
|--------|--------------------|
| 1a | a first liver disease filter |
| 2a | a first drug interaction filter |

It is contemplated that, in some embodiments, any one or more of the filters provided in Table 3 will not be included in the second plurality of filters. For example, in some embodiments, a characteristic associated with a particular survey result will be informative when qualifying a subject for one particular dihydropyridine-type calcium channel blocker pharmaceutical composition but not for another dihydropyridine-type calcium channel blocker pharmaceutical composition. Accordingly, it is contemplated that the second plurality of filters includes any sub-set of filters provided in Table 3. Likewise, the skilled artisan may know of other filters, not provided in Table 3, that may be combined with any subset of the filters provided in Table 3 to form the second plurality of filters results used in the methods described herein.

Referring to block 456, in some embodiments, the second plurality of filters includes a liver disease filter (e.g., first liver disease filter 222-1 in FIG. 3 and/or filter 1a in Table 3). The liver disease filter is configured to be fired at least when the first plurality of survey results indicate that the subject has had a liver problem. In some embodiments, liver problems that are capable of triggering the first liver disease filter include impaired hepatic function, acute liver failure, and cholestasis. When the liver disease filter is fired, the device transmits a warning corresponding to the liver disease filter, and requires the user to acknowledge the warning before authorizing a provision of the dihydropyridine-type calcium channel blocker pharmaceutical composition.

Referring to block 458, in some embodiments, the second plurality of filters includes a drug interaction filter (e.g., first drug interaction filter 222-2 in FIG. 3 and/or filter 2a in Table 3). The drug interaction filter is configured to be fired at least when the first plurality of survey results indicates that the subject is taking a medication that interacts with the dihydropyridine-type calcium channel blocker pharmaceutical composition. When the drug interaction filter is fired, the device transmits a warning corresponding to the drug interaction filter, and requires the user to acknowledge the warning before authorizing a provision of the dihydropyridine-type calcium channel blocker pharmaceutical composition.

In some embodiments, the drug capable of firing the drug interaction filter is one of simvastatin, cyclosporine, tacrolimus, sildenafil, or a CYP3A inhibitor. In some embodiments, the CYP3A inhibitor includes diltiazem, itraconazole, and clarithromycin. In some embodiments, medications that are capable of firing the drug interaction filter include propranolol, cimetidine, rifampicin, and fentanyl anesthesia. In some embodiments, these predetermined medications include but are not limited to digoxin, quinidine, coumarin anticoagulants, CYP3A4 inducers, phenytoin, and grapefruit juice and/or grapefruit extract.

The identity of drugs that are capable of triggering the drug interaction filter vary from one dihydropyridine-type calcium channel blocker to another dihydropyridine-type calcium channel blocker. The skilled artisan will know of drugs that interact with one dihydropyridine-type calcium channel blocker but not another. Inclusion of a drug within the drug interaction filter is dependent upon the identity and/or the dosage of the dihydropyridine-type calcium channel blocker pharmaceutical composition being authorized for over-the-counter use.

In some implementations, a drug that interacts with a dihydropyridine-type calcium channel blocker pharmaceutical composition is included within a filter 216 in the first filter category class 214, rather than within drug interaction filter 222 of the second filter category class 220. For example, according to some implementations, a particular drug included in drug-interaction filter 222 (e.g., as a risk factor) for a first dihydropyridine-type calcium channel blocker pharmaceutical composition, but included in a filter in the first plurality of filters (e.g., as a contraindication) for a second dihydropyridine-type calcium channel blocker pharmaceutical composition. However, a person skilled in the art will know whether to include a certain drug within drug interaction filter 222 or as a separate filter 216 in the first plurality of filters, based on the severity and risk of the drug interaction with the particular identity and dosage of the dihydropyridine-type calcium channel blocker being authorized for over-the-counter use.

Figure 6:
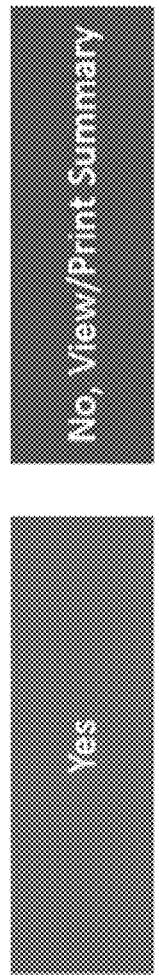
FIG. 6 illustrates feedback from a first survey in accordance with an embodiment of the present disclosure.

Referring to block 462, in some embodiments the warning 226 corresponding to a respective filter 222 in the second plurality of filters includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should take a dihydropyridine-type calcium channel blocker pharmaceutical composition in view of the underlying risk factor. Accordingly, acknowledgement is obtained from the subject when the subject indicates that they have discussed the risk factor underlying the respective filter in the second plurality of filters that was fired with a health care provider. For example, message 602 in FIG. 6 illustrates a warning that is generic to any fired filters. In some embodiments, the warning is specific to a particular filter (e.g., filter warning 226 in FIG. 2), e.g., communicating to the user why the filter was fired.

In some embodiments, an acknowledgment from the user is verified by the health care practitioner (e.g., the method requires verification in order for authorization of the provision of the dihydropyridine-type calcium channel blocker pharmaceutical composition), e.g., in order to verify an accuracy of the survey results of the subject. In some embodiments, e.g., when the acknowledgment is verified by the heath care practitioner, the subject is deemed a trusted subject, such that verification of future results is not required.

Referring to block 464 of FIG. 4D, the method includes obtaining acknowledgment from the subject for any warning 226 issued to the subject by any filter 222 in the second plurality of filters. If a filter 216 in the first plurality of filters fires, the subject is denied access to the over-the-counter dihydropyridine-type calcium channel blocker pharmaceutical composition.

Blocks 466-476. Referring to block 466 of FIG. 4E, the process control proceeds to the fulfillment process when no filter 216 in the first plurality of filters has been fired and the subject has acknowledged each warning 226 associated with each filter 222 in the second plurality of filters that was fired. In some embodiments, the fulfillment process comprises storing an indication in a user profile 234 of an initial order date and/or destination for the dihydropyridine-type calcium channel blocker pharmaceutical composition. The initial order date is utilized, for example, to verify at least a refill status of a provision of the dihydropyridine-type calcium channel blocker. The initial order date is also utilized, for example, to verify at least an elapsed period of time between an initial order and a future re-order. Such verification is required in order to ensure that certain tests (e.g., blood pressure tests) are taken regularly.

The fulfillment process further comprises communicating an over-the-counter drug facts label 230 for the dihydropyridine-type calcium channel blocker pharmaceutical composition to the subject. In some embodiments, the drug facts label is communicated to the subject in real-time, e.g., within the same user interface as used for the qualification process. In some embodiments, the over-the-counter drug facts label 230 specifies what the dihydropyridine-type calcium channel blocker pharmaceutical composition is for (e.g., to lower blood pressure, to treat heart disease, etc.) and any risks associated with taking the dihydropyridine-type calcium channel blocker pharmaceutical composition (e.g., drug-drug interactions, pharmacokinetic interactions, adverse reactions, etc.) For instance, in some embodiments, upon confirmation from the subject that the over the counter drug facts label has been received and read, the subject is authorized for provision of a dosage of from 1 mg to 10 mg of dihydropyridine-type calcium channel blocker no more than once per day (block 470). In another example embodiment upon confirmation from the subject that the over the counter drug facts label has been received and read, the subject is authorized for provision of a dosage of from 2.5 mg to 5 mg of dihydropyridine-type calcium channel blocker no more than once per day (block 472).

In some embodiments, upon confirmation from the subject that the over the counter drug facts label has been received and read, the subject is authorized for provision of a dosage of from 1 mg to 10 mg of amlodipine no more than once per day. In some embodiments, upon confirmation from the subject that the over the counter drug facts label has been received and read, the subject is authorized for provision of a dosage of from 2.5 mg to 10 mg of amlodipine no more than once per day. In some embodiments, upon confirmation from the subject that the over the counter drug facts label has been received and read, the subject is authorized for provision of a dosage of from 2.5 mg to 5 mg of amlodipine no more than once per day. In some embodiments, the dihydropyridine-type calcium channel blocker pharmaceutical composition comprises amlodipine besylate.

In some embodiments, upon confirmation from the subject that the over the counter drug facts label has been received and read, the subject is authorized for provision of a dosage of from 15 mg to 90 mg of nifedipine no more than once per day. In some embodiments, upon confirmation from the subject that the over the counter drug facts label has been received and read, the subject is authorized for provision of a dosage of from 30 mg to 60 mg of nifedipine no more than once per day. In some embodiments, upon confirmation from the subject that the over the counter drug facts label has been received and read, the subject is authorized for provision of a dosage of 30 mg of nifedipine no more than once per day. In some embodiments, upon confirmation from the subject that the over the counter drug facts label has been received and read, the subject is authorized for provision of a dosage of 60 mg of nifedipine no more than once per day.

In some embodiments, upon confirmation from the subject that the over the counter drug facts label has been received and read, the subject is authorized for provision of a dosage of from 2.5 mg to 20 mg of isradipine no more than once per day. In some embodiments, upon confirmation from the subject that the over the counter drug facts label has been received and read, the subject is authorized for provision of a dosage of from 2.5 mg to 10 mg of isradipine no more than once per day. In some embodiments, upon confirmation from the subject that the over the counter drug facts label has been received and read, the subject is authorized for provision of a dosage of from 5 mg to 10 mg of isradipine no more than once per day. In some embodiments, upon confirmation from the subject that the over the counter drug facts label has been received and read, the subject is authorized for provision of a dosage of 5 mg of isradipine no more than once per day. In some embodiments, upon confirmation from the subject that the over the counter drug facts label has been received and read, the subject is authorized for provision of a dosage of 10 mg of isradipine no more than once per day.

In some embodiments, upon confirmation from the subject that the over the counter drug facts label has been received and read, the subject is authorized for provision of a dosage of from 25 mg to 250 mg of nisoldipine no more than once per day. In some embodiments, upon confirmation from the subject that the over the counter drug facts label has been received and read, the subject is authorized for provision of a dosage of from 50 mg to 200 mg of nisoldipine no more than once per day. In some embodiments, upon confirmation from the subject that the over the counter drug facts label has been received and read, the subject is authorized for provision of a dosage of from 100 mg to 200 mg of nisoldipine no more than once per day. In some embodiments, upon confirmation from the subject that the over the counter drug facts label has been received and read, the subject is authorized for provision of a dosage of 200 mg of nisoldipine no more than once per day. In some embodiments, upon confirmation from the subject that the over the counter drug facts label has been received and read, the subject is authorized for provision of a dosage of 100 mg of nisoldipine no more than once per day.

Referring to block 474 of FIG. 4E, in some embodiments the fulfillment process further comprises authorizing provision of the dihydropyridine-type calcium channel blocker pharmaceutical composition to the subject. The authorization occurs upon confirmation from the subject that the over-the-counter drug facts label 230 has been received and read by the subject. In some embodiments, this authorization includes a destination associated with the subject. In some embodiments, the destination associated with the subject is stored in the user profile 234. In some embodiments, the destination associated with the subject is a physical address including a street address, a Post Office box, a pharmacy associated with the subject, a health care provider associated with the subject, and/or one or more coordinates (e.g., longitude, latitude, elevation). In some embodiments, the provision of the dihydropyridine-type calcium channel blocker pharmaceutical composition to the subject comprises shipping the dihydropyridine-type calcium channel blocker pharmaceutical composition to the physical address associated with the subject (block 476). In some embodiments, the provision of the dihydropyridine-type calcium channel blocker pharmaceutical composition to the subject comprises shipping the dihydropyridine-type calcium channel blocker pharmaceutical composition to a pharmacy associated and/or a location associated with a health care provider of the subject and/or an office of a medical practitioner associated with the subject.

Blocks 460-508. Referring to blocks 460-508 of FIGS. 4F-4I, a re-fulfillment process will be described infra. In some embodiments, the present disclosure provides a method for qualifying a subject for a refill of a dihydropyridine-type calcium channel blocker pharmaceutical composition. In some embodiments, the qualification for a refill of the dihydropyridine-type calcium channel blocker pharmaceutical composition follows an initial qualification of the subject, as described herein. In some embodiments, the qualification for a refill of the dihydropyridine-type calcium channel blocker pharmaceutical composition follows issuance of a prescription to the subject for the dihydropyridine-type calcium channel blocker pharmaceutical composition. For example, in some embodiments, a subject who is new to the qualification process is asked whether they previously received a prescription for the dihydropyridine-type calcium channel blocker pharmaceutical composition and, if the subject indicates that they have not previously received a prescription, the subject is directed to an initial qualification method and, if the subject indicates that they have previously received a prescription, the subject is directed to the refill qualification method, e.g., as described below.

Figure 4F:
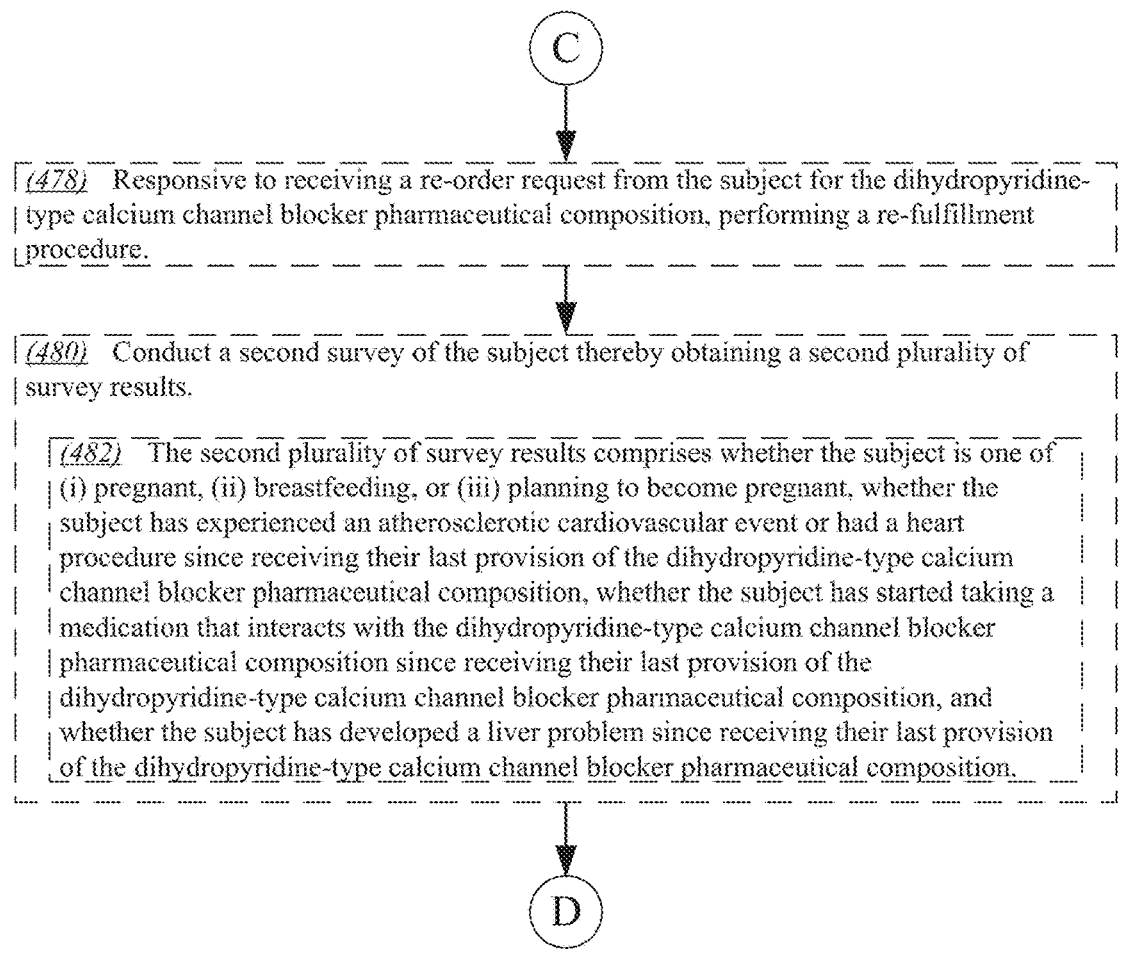

Referring to block 460 of FIG. 4F, in some embodiments a re-fulfillment procedure is performed. The re-fulfillment procedure is responsive to receiving a re-order request from the subject for the dihydropyridine-type calcium channel blocker pharmaceutical composition. In some embodiments, a prompt to initiate the re-fulfillment procedure is sent to user device 102 associated with the subject after a predetermined amount of time associated with a duration of dosages previously delivered to the subject (e.g., the user is reminded to fulfill their order of the dihydropyridine-type calcium channel blocker pharmaceutical composition just before, or just after, the user is scheduled to run out of a previously delivered provision.

Referring to blocks 480-482, in some embodiments the re-fulfillment procedure comprises conducting a second survey of the subject. The second survey is configured to obtain a second plurality of survey results. These results are derived from corresponding survey questions (e.g., the device transmits one or more survey questions to the user, prompting a response, and then receives a response to the one or more survey questions back from the subject). In some embodiments, the second plurality of survey results include some or all of the characteristics listed in Table 4. For example, in some embodiments, the second plurality of survey results includes 1, 2, 3, 4, or all 5 of the characteristic listed in Table 4. In one embodiment, the second survey questions and results include at least characteristics 1-4 as provided in Table 4.

In some embodiments, the second survey results comprises at least one of whether the subject is one of pregnant, breastfeeding, or planning to become pregnant (e.g., responsive to a survey question that is associated with and/or applied to (815) a pregnancy filter of a first category class 214-2), whether the subject has experienced an atherosclerotic cardiovascular event or had a heart procedure since receiving their last provision of the dihydropyridine-type calcium channel blocker pharmaceutical composition (e.g., responsive to a survey question that is associated with and/or applied to (820) an atherosclerotic cardiovascular event filter of a second category class 220-2), whether the subject has started taking a medication that interacts with the dihydropyridine-type calcium channel blocker pharmaceutical composition since receiving their last provision of the dihydropyridine-type calcium channel blocker pharmaceutical composition (e.g., responsive to a survey question that is associated with and/or applied to (825) a drug interaction filter of a second category class 220-2), and whether the subject has developed a liver problem since receiving their last provision of the dihydropyridine-type calcium channel blocker pharmaceutical composition (e.g., responsive to a survey question that is associated with and/or applied to (830) a liver disease filter of a second category class 220-2).

In some embodiments, the second survey includes questions that elicit responses providing some or all of the characteristics listed in Table 4. In some embodiments, the second survey includes questions corresponding to each of the survey results required for the methods described herein. In other embodiments, the second survey includes questions corresponding to only a subset of the survey results required for the methods described herein. In such embodiments, other survey results required for the methods described herein are acquired through other means (e.g., upon registration/subscription for a service associated with qualifying the subject for over-the-counter medication, from a healthcare provider, from a prior survey, from a database associated with a pharmacy, etc.) For example, in some embodiments, the subject provides a personal medical identification associated with an insurer, a hospital, or other healthcare provider and information about the subject required for the methods described herein, e.g., one or more survey results, is acquired from a preexisting database associated with the personal medical identification (e.g., a last cholesterol or blood pressure measurement determined for the subject).

TABLE 4

Exemplary Second Survey Questions

| Result | Exemplary Characteristics |
|---|---|
| 1 | whether the subject is one of (i) pregnant, (ii) breastfeeding, or (iii) planning to become pregnant |
| 2 | whether the subject has experienced an atherosclerotic cardiovascular event or had a heart procedure since receiving their last provision of the dihydropyridine-type calcium channel blocker pharmaceutical composition |
| 3 | whether the subject has started taking a medication that interacts with the dihydropyridine-type calcium channel blocker pharmaceutical composition since receiving their last provision of the dihydropyridine-type calcium channel blocker pharmaceutical composition |
| 4 | whether the subject has developed a liver problem since receiving their last provision of the dihydropyridine-type calcium channel blocker pharmaceutical composition |
| 5 | a blood pressure status of the subject |
| 6 | whether the subject has developed a side effect associated with the dihydropyridine-type calcium channel blocker since receiving their last provision of the dihydropyridine-type calcium channel blocker pharmaceutical composition |

It is contemplated that, in some embodiments, any one or more of the survey questions provided in Table 4 will not be included in the second survey (e.g., will not be used for the reassessment). For example, in some embodiments, a characteristic associated with a particular survey questions will be informative when qualifying a subject for one particular dihydropyridine-type calcium channel blocker but not for another dihydropyridine-type calcium channel blocker. For instance, a survey question is queried for isradipine qualifying surveys but not for nisoldipine qualifying surveys. The skilled artisan will recognize that different dihydropyridine-type calcium channel blockers carry different risk and drug interaction profiles. Accordingly, survey information required for qualifying a subject for access to one dihydropyridine-type calcium channel blocker with a known adverse drug interaction may not be necessary for qualifying the same subject for access to a second dihydropyridine-type calcium channel blocker.

Accordingly, it is contemplated that the second survey questions elicit responses to any sub-set of survey results provided in Table 4. For brevity, all possible combinations of the characteristics provided in Table 4 are not specifically delineated here. However, the skilled artisan will easily be able to envision any particular subset of survey questions designed to elicit responses to any subset of characteristics provided in Table 4. Likewise, the skilled artisan may know of other survey questions, not provided in Table 4, that may be combined with any subset of the survey questions provided in Table 4 to form the second survey questions used in the methods described herein.

Referring to block 484 of FIG. 4G, all or a portion the results are run against a third plurality of filters of the first category class. When a respective filter in the third plurality of filters is fired (e.g., when a survey result indicates that a triggering condition 218 has been met), the subject is deemed not qualified for the dihydropyridine-type calcium channel blocker pharmaceutical composition and the method is terminated without delivery of the dihydropyridine-type calcium channel blocker pharmaceutical composition.

Referring to blocks 486-500, specific filters in the third plurality of filters and their exemplary triggering conditions that cause the corresponding filter to fire are detailed.

In some embodiments, the third plurality of filters of the first category class includes some or all of the filters listed in Table 5. For example, in some embodiments, the third plurality of filters includes one or both of the filters listed in Table 5.

TABLE 5

Exemplary Third Plurality of Filters of the First Category Class

| Filter | Exemplary Criteria |
|---|---|
| 1a | a second pregnancy filter |
| 2a | a second blood pressure filter |

In one embodiment, the third plurality of filters includes at least filters 1a-2a as provided in Table 5. In another embodiment, the third plurality of filters includes at least filter 1a as provided in Table 5. In another embodiment, the first plurality of filters includes at least filter 2a as provided in Table 5.

It is contemplated that, in some embodiments, any one or more of the filters provided in Table 5 will not be included in the third plurality of filters. For example, in some embodiments, a characteristic associated with a particular survey result will be informative when qualifying a subject for one particular dihydropyridine-type calcium channel blocker but not for another dihydropyridine-type calcium channel blocker. Likewise, the skilled artisan may know of other filters, not provided in Table 5, which may be combined with any subset of the filters provided in Table 2 to form the third plurality of filters results used in the methods described herein. For brevity, all possible combinations of the filters provided in Table 5 are not specifically delineated here.

Referring to block 486, in some embodiments the third plurality of filters comprises a second pregnancy filter, e.g., as described above in relation to the first pregnancy filter 216-1. In some embodiments, the pregnancy filter is configured to be fired at least when the second plurality of survey results indicates that the subject is pregnant or the subject is breastfeeding. In some embodiments, the pregnancy filter is also configured to be fired when the subject is planning on becoming pregnant. When the pregnancy filter is fired, the subject is not permitted to obtain the dihydropyridine-type calcium channel blocker pharmaceutical composition over-the-counter (e.g., the method is terminated without authorizing re-provision of the dihydropyridine-type calcium channel blocker pharmaceutical composition to the subject).

Referring to blocks 488-494, in some embodiments when the subject profile for the subject does not include a recent blood pressure for the subject (e.g., a blood pressure or acknowledgement that the subject's blood pressure is below a threshold target level that was obtained by the device within a predetermined time period, such as within the past month, within the past two months, within the past three months, within the past six months, within the past year, etc.), a blood pressure status of the subject is obtained in the second survey 210 (e.g., when a subject profile stored in the subject profile data store 232, associated with the subject, does not include a recent indication of the subject's blood pressure, the device queries (810) the user to provide a blood pressure status, e.g., actual blood pressure readings or an indication of whether the subject's blood pressure is below a predetermined threshold target). In some embodiments, the predetermined time period is shorter (e.g., one month) when the user has only been authorized for a single provision of the dihydropyridine-type calcium channel blocker pharmaceutical agent than after the user has been authorized for multiple provisions of the dihydropyridine-type calcium channel blocker pharmaceutical agent (e.g., upon the first request for re-order, the user is prompted to provide a blood pressure status if the user's profile does not include a blood pressure status obtained in the past month, while upon subsequent requests for re-order, the user is prompted to provide a blood pressure status if the user's profile does not include a blood pressure status obtained in the past six months.

Accordingly, in some embodiments, the third plurality of filters of the first category class 214-2 includes a second blood pressure filter that is configured to be fired at least when the second survey results indicate that the subject has hypertension (e.g., a systolic blood pressure greater than 130 mm Hg or a diastolic blood pressure greater than 80 mm Hg). In some embodiments, the second blood pressure filter is fired when the second survey results indicate that the systolic blood pressure of the subject is above 130 mm Hg or the diastolic blood pressure of the subject is above 80 mm Hg. If the blood pressure filter is fired, the subject is not permitted to obtain the dihydropyridine-type calcium channel blocker pharmaceutical composition pharmaceutical composition over-the-counter (e.g., the method is terminated without authorizing provision of the dihydropyridine-type calcium channel blocker pharmaceutical composition to the subject). In some embodiments, the second plurality of survey results indicates that the subject has developed hypertension when the second plurality of survey results include that the subject has been diagnosed with hypertension since receiving their last provision of the dihydropyridine-type calcium channel blocker. In some embodiments, the second plurality of survey results indicates that the subject has developed hypertension when the second plurality of survey results include that the subject has experienced a symptom (e.g., a new and/or worsening symptom) of hypertension since receiving their last provision of the dihydropyridine-type calcium channel blocker.

In some embodiments, the third plurality of filters of the first category class 214-2 includes a second blood pressure filter that is configured to be fired at least when the second survey results indicate that the subject has hypertension (e.g., a systolic blood pressure greater than 130 mm Hg or a diastolic blood pressure greater than 80 mm Hg), regardless of whether the subject profile for the subject includes a recent blood pressure for the subject.

In some embodiments, e.g., when the second plurality of survey results indicate that the subject has hypertension, the device fires the second blood pressure filter and transmits, to the subject, advice to visit a doctor to discuss taking a prescription-strength blood pressure medication.

Figure 8A:
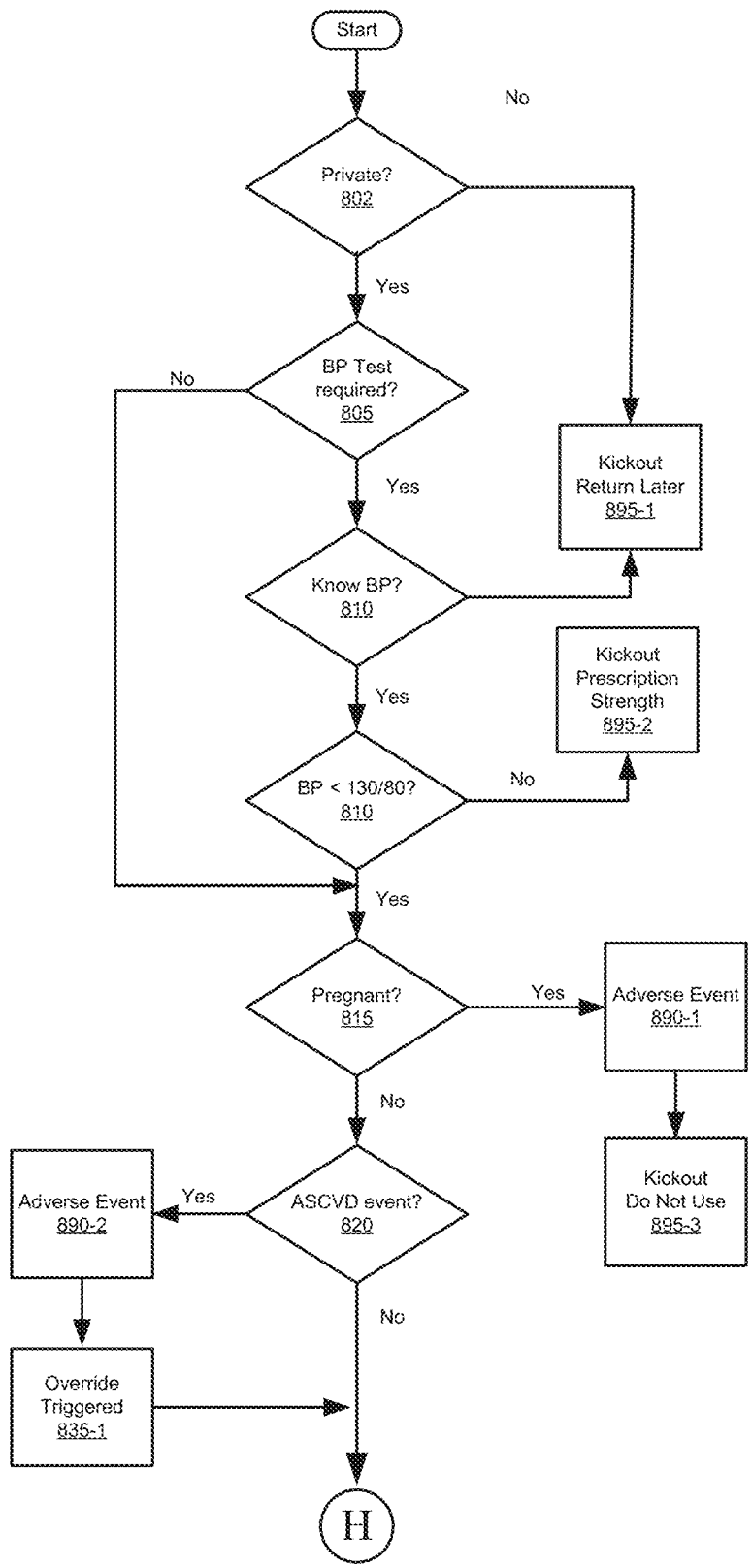
FIGS. 8A and 8B collectively illustrate an example method for qualifying a subject for a refill of an over-the-counter provision dihydropyridine-type calcium channel blocker pharmaceutical composition in accordance with an embodiment of the present disclosure.
Figure 8B:
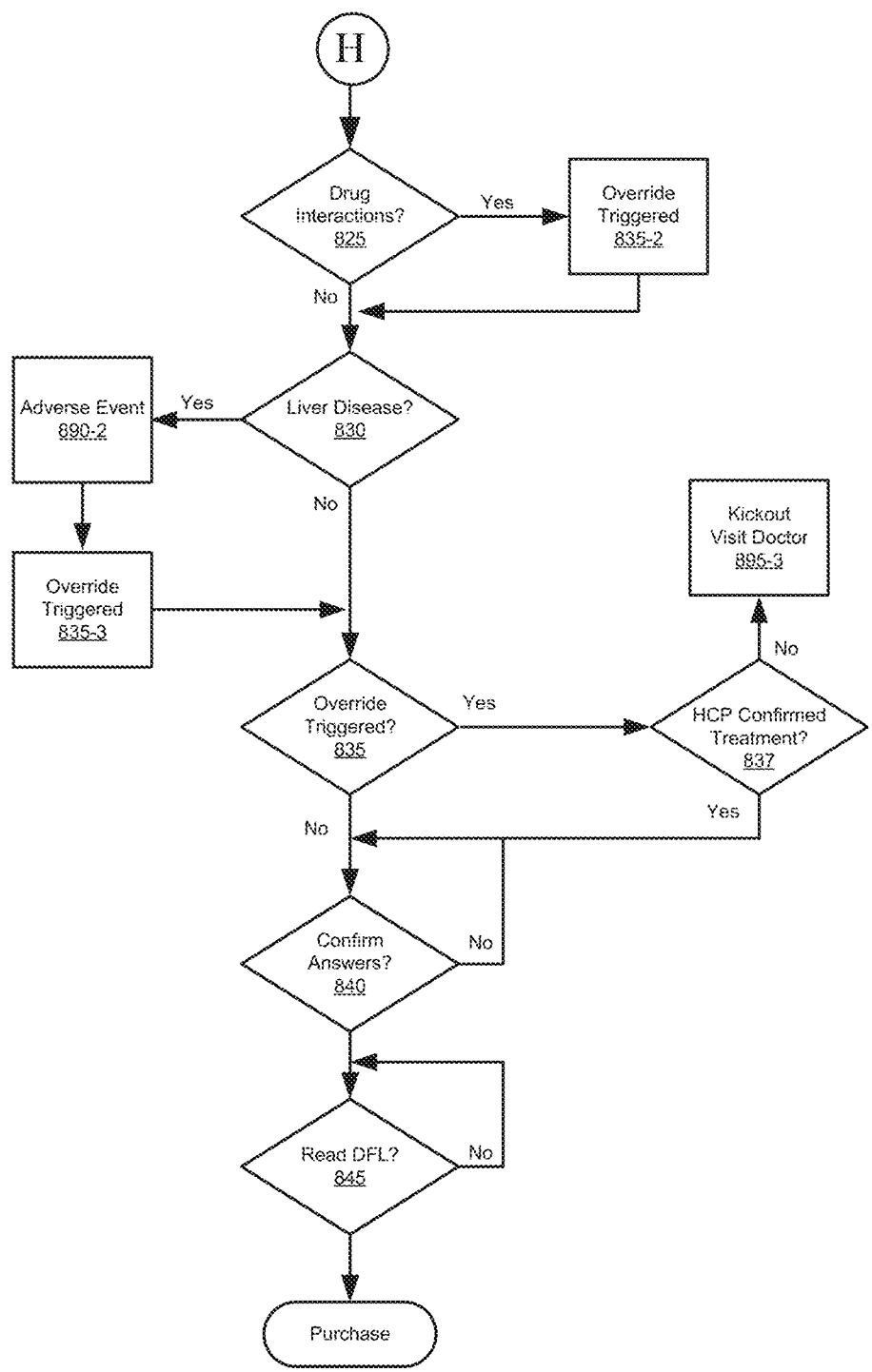

Referring to block 496 of FIG. 4H, the method also includes running all or a portion of the second survey results against a fourth plurality of filters of the second category class 220-2. When a respective filter in the fourth plurality of filters is fired, the subject is provided with a warning corresponding to the respective filter. In some embodiments, the warning is provided as a next step, e.g., prior to applying survey results to any subsequent filters, after the corresponding filter is fired. For example, with respect to FIGS. 8A-8B, in some embodiments, e.g., when the atherosclerotic cardiovascular event filter is triggered at 820, the device would provide the subject with a warning prior to proceeding to the drug interaction filter at 825, e.g., requiring the subject confirm they have discussed their atherosclerotic cardiovascular event with a health care provider and the healthcare provider still recommends taking a dihydropyridine-type calcium channel blocker pharmaceutical composition. In some embodiments the warning is provided after applying survey results to all subsequent filters. For example, with respect to FIGS. 8A-8B, in some embodiments, e.g., when the atherosclerotic cardiovascular event filter is triggered at 820, the device would proceed to the drug interaction filter at 825 prior to transmitting a warning to the subject, and then transmit all warnings corresponding to filters of the second category class, at 837, after survey results have been applied to all subsequent filters.

Referring to block 498, in some embodiments the fourth plurality of filters comprise at least an atherosclerotic cardiovascular event filter, a second drug interaction filter, and a second liver disease filter.

In some embodiments, the fourth plurality of filters of the second category class 220-2 includes some or all of the filters listed in Table 6. For example, in some embodiments, the fourth plurality of filters includes 2, 3, or all 4 of the filters listed in Table 2.

TABLE 6

Exemplary Fourth Plurality of Filters of the Second Category Class

| Filter | Exemplary Criteria |
|--------|--------------------|
| 1a | an atherosclerotic cardiovascular event filter |
| 2a | a second drug interaction filter |
| 3a | a second liver disease filter |
| 4a | a side effects filter |

In one embodiment, the fourth plurality of filters includes at least filters 1a-4a as provided in Table 6. In another embodiment, the fourth plurality of filters includes at least filters 1a, 2a, and 3a as provided in Table 6. In another embodiment, the fourth plurality of filters includes at least filters Ta, 2a, and 4a as provided in Table 6. In another embodiment, the fourth plurality of filters includes at least filters 2a, 3a, and 4a as provided in Table 6. In another embodiment, the fourth plurality of filters includes at least filters 1a and 2a as provided in Table 6. In another embodiment, the fourth plurality of filters includes at least filters 1a and 3a as provided in Table 6. In another embodiment, the fourth plurality of filters includes at least filters 1a and 4a as provided in Table 6. In another embodiment, the fourth plurality of filters includes at least filters 2a and 3a as provided in Table 6. In another embodiment, the fourth plurality of filters includes at least filters 2a and 4a as provided in Table 6. In another embodiment, the fourth plurality of filters includes at least filters 3a and 4a as provided in Table 6.

It is contemplated that, in some embodiments, any one or more of the filters provided in Table 6 will not be included in the fourth plurality of filters. For example, in some embodiments, a characteristic associated with a particular survey result will be informative when qualifying a subject for one particular dihydropyridine-type calcium channel blocker pharmaceutical composition but not for another dihydropyridine-type calcium channel blocker pharmaceutical composition. Accordingly, it is contemplated that the fourth plurality of filters includes any sub-set of filters provided in Table 6. Likewise, the skilled artisan may know of other filters, not provided in Table 6, that may be combined with any subset of the filters 222 provided in Table 6 to form the fourth plurality of filters results used in the methods described herein.

Referring to block 498, in some embodiments, the fourth plurality of filters includes an atherosclerotic cardiovascular event filter that is configured to be fired at least when the second survey results indicate that the subject has experienced an atherosclerotic cardiovascular event or the subject has had a heart procedure since receiving their last provision of the dihydropyridine-type calcium channel blocker pharmaceutical composition. Atherosclerotic cardiovascular events, capable of firing the atherosclerotic cardiovascular event filter, include hospitalization for angina pectoris, coronary revascularization, myocardial infarction, cardiovascular death, resuscitated cardiac arrest, hospitalization for heart failure, stroke, TIA, or peripheral vascular disease. Similarly, heart procedures include pace maker installment, arrhythmia treatment, and aneurysm repair. In some embodiments, the second plurality of survey results indicates that the subject has developed an atherosclerotic cardiovascular event when the second plurality of survey results include that the subject has been diagnosed with an atherosclerotic cardiovascular event since receiving their last provision of the dihydropyridine-type calcium channel blocker. In some embodiments, the second plurality of survey results indicates that the subject has developed an atherosclerotic cardiovascular event when the second plurality of survey results include that the subject has experienced a symptom (e.g., a new and/or worsening symptom) of an atherosclerotic cardiovascular event since receiving their last provision of the dihydropyridine-type calcium channel blocker.

Referring to block 498, in some embodiments, the fourth plurality of filters includes a second drug interaction filter that is configured to be fired at least when the second plurality of survey results indicates that the subject has started taking a medication that interacts with the dihydropyridine-type calcium channel blocker pharmaceutical composition since receiving their last provision of the dihydropyridine-type calcium channel blocker pharmaceutical composition. As previously described, these interactions can be pharmacodynamic drug-drug interactions or pharmacokinetic drug-drug interactions. Typically, the interactions (e.g., triggering conditions 224) that are capable of firing the second drug interaction filter are the same as the interactions that are capable of firing the first drug interaction filter assuming that the dihydropyridine-type calcium channel blocker pharmaceutical composition is the same between the fulfillment process and the re-fulfillment process.

Referring to block 498, in some embodiments, the fourth plurality of filters includes a second liver disease filter that is configured to be fired at least when the second survey results indicate that the subject has developed symptoms of liver disease since receiving their last provision of the dihydropyridine-type calcium channel blocker pharmaceutical composition. In some embodiments, the second plurality of survey results indicates that the subject has developed liver disease when the second plurality of survey results include that the subject has been diagnosed with a liver disease since receiving their last provision of the dihydropyridine-type calcium channel blocker. In some embodiments, the second plurality of survey results indicates that the subject has developed a liver disease when the second plurality of survey results include that the subject has experienced a symptom (e.g., a new and/or worsening symptom) of a liver disease since receiving their last provision of the dihydropyridine-type calcium channel blocker e.g., hepatic enzyme elevations (e.g., which are mostly consistent with cholestasis or hepatitis, jaundice, abdominal pain and/or swelling, swelling in the legs and/or ankles, irritated skin, a dark urine color, a pale, bloody, or tar-colored stool, chronic fatigue, nausea and/or vomiting, loss of appetite, and a tendency to bruise easily.

Referring to block 500, in some embodiments the second survey results further comprise whether the subject has developed a side effect associated with the dihydropyridine-type calcium channel blocker pharmaceutical composition since receiving their last provision of the dihydropyridine-type calcium channel blocker pharmaceutical composition. Accordingly, in some embodiments, the fourth plurality of filters further comprises a side effect filter that is configured to be fired at least when the second survey results indicate that the subject has developed a side effect since receiving their last provision of the dihydropyridine-type calcium channel blocker pharmaceutical composition. Side effects that are capable of triggering (e.g., triggering condition) the side effect filter include swelling of the legs, swelling of the ankles, tiredness, extreme sleepiness, stomach pain, nausea, dizziness, flushing, arrhythmia or an irregular heartbeat, heart palpitations, muscle rigidity, tremors, and abnormal muscle movement. In some embodiments, side effects that are capable of triggering the side effect filter include constipation, headache, edema, gingival overgrowth, and/or an increase or decrease in heart rate. In some embodiments, side effects that are capable of triggering the side effect filter include fatigue, dyspnea, tachycardia, pollakiuria, and vomiting. In some embodiments, side effects that are capable of triggering the side effect filter mood changes (e.g., nervousness), nasal congestion, sore throat, and peripheral edema.

Referring to block 502, in some embodiments when a respective filter in the third plurality of filters or fourth plurality of filters is fired, a record associated with the firing of the respective filter is stored (e.g., memorializing an adverse event that is required to be reported to a regulatory agency). This record is stored in an adverse event module 242 which comprises records of filter firing events associated with a plurality of subjects (e.g., an aggregation of adverse events associated with the dihydropyridine-type calcium channel blocker pharmaceutical composition across a population of subjects taking the dihydropyridine-type calcium channel blocker pharmaceutical composition over-the-counter). In some embodiments, an indication of the adverse event is communicated to a third party (e.g., a medical practitioner associated with the subject, a health care provider of the subject, and/or a manufacturer/promoter of the dihydropyridine-type calcium channel blocker pharmaceutical composition). In some embodiments, the indication is automatically stored in the adverse event module 242 when submitted by a subject as part of the second survey.

Referring to block 504, in some embodiments the method also includes obtaining acknowledgment from the subject for each warning issued to the subject by any filter in the fourth plurality of filters. As described with respect to the warnings issued in conjunction with the second plurality of filters of the second category class, in some embodiments, the warning includes a prompt for the subject to indicate whether they have discussed the risk factor underlying the respective filter in the second plurality of filters that was fired with a health care practitioner (e.g., a licensed medical practitioner), e.g., and the health care practitioner indicated that the subject should take a dihydropyridine-type calcium channel blocker pharmaceutical composition in view of the underlying risk factor. Accordingly, acknowledgement is obtained from the subject when the subject indicates that they have discussed the risk factor underlying the respective filter in the fourth plurality of filters that was fired with a health care provider.

Referring to block 506 of FIG. 4I, in some embodiments the procedure further comprises proceeding with the re-fulfillment process when the re-fulfillment process is not already terminated by the firing of a filter in the third plurality of filters (e.g., the second pregnancy filter). In order for the re-fulfillment process to complete the subject is required to acknowledge each warning associated with each filter 222-2 in the fourth plurality of filters that was fired.

Referring to block 508, in some embodiments the re-fulfillment process also includes storing an indication in the user profile 234 of the subject of a re-order 238 for the dihydropyridine-type calcium channel blocker pharmaceutical composition. The re-fulfillment process further comprises communicating an over-the-counter drug facts label 230 for the dihydropyridine-type calcium channel blocker pharmaceutical composition to the subject. As previously described, the communication of the over-the-counter drug facts label 230 can occur in a variety of means. Upon confirmation from the subject that the over-the-counter drug facts label 230 has been received and read, the method includes authorizing a re-order provision of the dihydropyridine-type calcium channel blocker pharmaceutical composition to the subject. In some embodiments, this re-order provision includes the destination of the subject.

FIG. 7 illustrates an example method (700) (e.g., performed at an electric device) for qualifying a subject for an over-the-counter dihydropyridine-type calcium channel blocker pharmaceutical composition. In some embodiments, the method of FIG. 7 is utilized when the subject has not been previously qualified for the medication. In some embodiments, the method of FIG. 7 is utilized when the subject was previously qualified for the dihydropyridine-type calcium channel blocker pharmaceutical composition but a predetermined period of time elapsed since the previous qualification occurred (e.g., the most recent qualification of the subject was greater than one year ago).

Referring to FIG. 7, the device prompts (702) the subject to acknowledge a privacy notice. Since the present disclosure requires the subject to know and input sensitive medical information (e.g., information only the subject and a medical practitioner have access to), privacy of this information is important. Once the subject has acknowledged they have the requisite privacy for continuing, the device prompts (704) the user to confirm that they know their blood pressure and cholesterol levels (e.g., because the subject must know their blood pressure and their total cholesterol, including their HDL, values in order to complete the qualification process). If the subject indicates they do not know their blood pressure or cholesterol level, the process terminates 795-2 without authorizing provision of the dihydropyridine-type calcium channel blocker pharmaceutical agent, and optionally transmits advice to the user to return later, e.g., once they know their blood pressure and cholesterol levels. If the subject indicates they know their blood pressure and cholesterol levels, the process continues.

The device prompts the subject to provide information about their pregnancy status and then applies (705) the answer received from the subject to a pregnancy filter. When the pregnancy filter is fired (e.g., when the answer indicates the subject is pregnant, breastfeeding, or planning to become pregnant), the device terminates (795-1) the qualification process without authorizing provision of the dihydropyridine-type calcium channel blocker pharmaceutical agent and, optionally, transmits advice to the user as to why they should not take the dihydropyridine-type calcium channel blocker pharmaceutical agent.

When the pregnancy filter is not fired, the device proceeds with the qualification process, prompting the subject to indicate whether they are taking a dihydropyridine-type calcium channel blocker and then applies (710) the answer received from the subject to a dihydropyridine medication filter. When the dihydropyridine medication filter is fired (e.g., when the answer indicates the subject is taking a dihydropyridine-type calcium channel blocker), the device terminates (795-2) the qualification process without authorizing provision of the dihydropyridine-type calcium channel blocker pharmaceutical agent and, optionally, transmits advice to the user to return later (e.g., when they are not taking a dihydropyridine-type calcium channel blocker pharmaceutical agent).

When the dihydropyridine medication filter is not fired, the device proceeds with the qualification process, prompting the subject to provide their blood pressure and then applies (715) the answer received from the subject to a blood pressure filter. When the blood pressure filter is fired (e.g., when the answer indicates the subject has normal blood pressure, slightly elevated blood pressure, stage 2 hypertension, or is in hypertensive crisis), the device terminates (795-3 through 795-6) the qualification process without authorizing provision of the dihydropyridine-type calcium channel blocker pharmaceutical agent. Optionally, when the device terminates the process in response to determining (715-2) the subject has slightly elevated blood pressure, the device transmits (795-3) advice for the subject to maintain a healthy diet and to exercise. Optionally, when the device terminates the process in response to determining (715-3) the subject has normal blood pressure, the device transmits (795-4) advice for the subject that they do not need a dihydropyridine-type calcium channel blocker pharmaceutical agent. Optionally, when the device terminates the process in response to determining (715-4) the subject has hypertension stage 2, the device transmits (795-5) advice for the subject to discuss obtaining a prescription for a dihydropyridine-type calcium channel blocker pharmaceutical agent with a medical professional. Optionally, when the device terminates the process in response to determining (715-4) the subject is in hypertensive crisis, the device transmits (795-6) advice for the subject to seek emergency medical care.

When the blood pressure filter is not fired, the device proceeds with the qualification process, prompting the subject to provide information about their cardiovascular history. When the answer to the prompt indicates the subject has had a cardiovascular problem or heart procedure, the device creates a record of an exemption condition (760-1). The device proceeds with the qualification process, prompting (725) the subject to provide information about their gender. The device proceeds with the qualification process, prompting the subject to provide their age and then applies (730) this information to an age filter. When the age filter is fired (e.g., when the subject is less than eighteen years old), the device terminates (795-1) the qualification process without authorizing provision of the dihydropyridine-type calcium channel blocker pharmaceutical agent and, optionally, transmits advice to the user as to why they should not take the dihydropyridine-type calcium channel blocker pharmaceutical agent. When the subject answers that they are eighty years old or greater, the device creates a record of an exemption condition (760-2).

When the age filter is not fired, the device proceeds with the qualification process, prompting the subject to provide their race (735), whether they are currently taking blood pressure medication (740), whether they have diabetes (745), their history of smoking (750), and their cholesterol levels (755). If no record of an exemption condition was created (e.g., the subject has not had a cardiovascular problem or heart procedure and is younger than 80), the device calculates an atherosclerotic cardiovascular disease (ASCVD) event risk for the subject (e.g., based on the answers to prompts (715-755) and applies (765) the calculated risk to a pooled cohort equation filter. When the pooled cohort equation filter is fired (e.g., when the risk of an ASCVD event is less than 10 percent or is incalculable), the device terminates (795-3, 795-7) the qualification process without authorizing provision of the dihydropyridine-type calcium channel blocker pharmaceutical agent. Optionally, when the device terminates the process in response to determining (765-2) the subject has an incalculable risk for an ASCVD event, the device transmits (795-7) advice for the subject to visit a medical professional to discuss whether taking a dihydropyridine-type calcium channel blocker pharmaceutical agent is appropriate. Optionally, when the device terminates the process in response to determining (765-3) that the subject has a low risk of an ASCVD event (e.g., less than 10%), the device transmits (795-3) advice for the subject to maintain a healthy diet and to exercise.

When the pooled cohort equation filter is not fired, the device proceeds with the qualification process, prompting the subject to indicate whether they have had liver problems and then applies (770) the answer received from the subject to a liver disease filter. When the liver disease filter is fired (e.g., when the answer indicates the subject has had a liver problem), the device initiates (780-1) an override procedure (e.g., creates a record indicating that the user must confirm they have discussed taking a dihydropyridine-type calcium channel blocker pharmaceutical composition with a health care provider).

The device proceeds with the qualification process, prompting the subject to provide information about their current medications (e.g., whether they're currently taking a medication that interacts with the dihydropyridine-type calcium channel blocker pharmaceutical composition) and then applies (775) the answer received from the subject to a drug interaction filter. When the drug interaction filter is fired (e.g., when the answer indicates the subject is taking a medication that interactions with the dihydropyridine-type calcium channel blocker pharmaceutical composition), the device initiates (780-2) an override procedure (e.g., creates a record indicating that the user must confirm they have discussed taking a dihydropyridine-type calcium channel blocker pharmaceutical composition with a health care provider).

The device proceeds with the qualification process, determining (782) whether the override procedure has been triggered (e.g., by firing of either of the liver disease or drug interaction filters). If the override procedure has been triggered, the device prompts (784) the user to confirm that they have spoken with a medical professional about taking a dihydropyridine-type calcium channel blocker pharmaceutical composition (e.g., in view of the underlying risk factor that triggered the liver disease and/or drug interaction filter) and the medical professional recommended taking the dihydropyridine-type calcium channel blocker pharmaceutical composition. If the user's response indicates they have not spoken with a medical professional or the medical professional did not recommend taking the dihydropyridine-type calcium channel blocker pharmaceutical composition, the device terminates (795-8) the process and, optionally, transmits advice for the subject to consult a medical professional.

If the override procedure was not triggered, or the override procedure was triggered and the subject's response indicated that a medical professional recommended they take a dihydropyridine-type calcium channel blocker pharmaceutical composition (e.g., in view of the underlying risk factor triggering the override procedure), the device proceeds with the qualification process, prompting (785) the subject to confirm their answers. If the user confirms their answers, the device transmits (790) a drug facts label for the dihydropyridine-type calcium channel blocker pharmaceutical composition and prompts the user to read the drug facts label. If the subject confirms they have read the drug facts label, the device proceeds to authorize (795) purchase of the dihydropyridine-type calcium channel blocker pharmaceutical composition.

FIG. 8 illustrates an example method for qualifying a subject for a refill of an over-the-counter dihydropyridine-type calcium channel blocker pharmaceutical composition (e.g., following a prescription from a medical professional or initial qualification by a method described herein). Referring to FIG. 8, the device prompts (802) the subject to acknowledge a privacy notice. Once the subject has acknowledged they have the requisite privacy for continuing, the device determines (805) whether a blood pressure input for the subject is required. When a new blood pressure input is required (e.g., when the subject's profile does not include a record of the subject's blood pressure taken within the past month, e.g., for a first reorder process, or within the past six months, e.g., for a subsequent reorder process), the device prompts (810) the subject to confirm they know their blood pressure. When the user indicates they do not know their blood pressure, the device terminates (895-1) the process without authorizing provision of the dihydropyridine-type calcium channel blocker pharmaceutical agent, optionally transmitting advice for the user to return once they know their blood pressure. When the user indicates they do know their blood pressure, the device proceeds with the process, prompting the user to indicate whether their blood pressure is below a threshold target level (e.g., under 130/80, evidencing the efficacy of the dihydropyridine-type calcium channel blocker pharmaceutical agent) and applies (810) the answer received from the subject to a blood pressure filter. When the blood pressure filter is fired (e.g., when the answer indicates the subject has a blood pressure is not below a threshold target level, e.g., 130/80), the device terminates (895-2) the qualification process, optionally transmitting advice for the subject to discuss taking a prescription-strength dihydropyridine-type calcium channel blocker pharmaceutical agent with a medical professional.

When the blood pressure filter is not fired, or the subject's answer indicates their blood pressure is below the threshold target level, the device proceeds with the qualification process, prompting the subject to provide information about their pregnancy status and then applies (815) the answer received from the subject to a pregnancy filter. When the pregnancy filter is fired (e.g., when the answer indicates the subject is pregnant, breastfeeding, or planning to become pregnant), the device creates (890-1) a record of an adverse event (e.g., aggregated in an adverse event data store having records of adverse events from a plurality of users), terminates (895-3) the qualification process and, optionally, transmits advice to the user as to why they should not take the dihydropyridine-type calcium channel blocker pharmaceutical composition.

When the pregnancy filter is not fired, the device proceeds with the qualification process, prompting the subject to provide information about their cardiovascular history and applies (820) the answer to an atherosclerotic cardiovascular event filter. When the atherosclerotic cardiovascular event filter is fired (e.g., when the subject's answer indicates the subject has developed a cardiovascular problem or had a heart procedure since receiving their last provision of the dihydropyridine-type calcium channel blocker pharmaceutical composition), the device creates (890-2) a record of an adverse event (e.g., aggregated in an adverse event data store having records of adverse events from a plurality of users) and initiates (835-1) an override procedure (e.g., creates a record indicating that the user must confirm they have discussed taking a dihydropyridine-type calcium channel blocker pharmaceutical composition with a health care professional).

The device proceeds with the qualification process, prompting the subject to provide information about their current medications and then applies (825) the answer received from the subject to a drug interaction filter. When the drug interaction filter is fired (e.g., when the answer indicates the subject has started taking a medication that interactions with the dihydropyridine-type calcium channel blocker pharmaceutical composition), the device initiates (835-2) an override procedure (e.g., creates a record indicating that the user must confirm they have discussed taking a dihydropyridine-type calcium channel blocker pharmaceutical composition with a health care professional).

The device proceeds with the qualification process, prompting the subject to indicate whether they have developed a liver problem and then applies (830) the answer received from the subject to a liver disease filter. When the liver disease filter is fired (e.g., when the answer indicates the subject has developed a liver problem since receiving their last provision of the dihydropyridine-type calcium channel blocker pharmaceutical composition), the device creates (890-2) a record of an adverse event (e.g., aggregated in an adverse event data store having records of adverse events from a plurality of users) and initiates (835-3) an override procedure (e.g., creates a record indicating that the user must confirm they have discussed taking a dihydropyridine-type calcium channel blocker pharmaceutical composition with a health care professional).

The device proceeds with the qualification process, determining (835) whether the override procedure has been triggered (e.g., by firing of any one of the atherosclerotic cardiovascular event filter, the liver disease filter, or the drug interaction filter). If the override procedure has been triggered, the device prompts (837) the user to confirm that they have spoken with a medical professional about taking a dihydropyridine-type calcium channel blocker pharmaceutical composition (e.g., in view of the underlying risk factor that triggered the atherosclerotic cardiovascular event, liver disease, and/or drug interaction filter) and the medical professional recommended taking the dihydropyridine-type calcium channel blocker pharmaceutical composition. If the user's response indicates they have not spoken with a medical professional or the medical professional did not recommend taking the dihydropyridine-type calcium channel blocker pharmaceutical composition, the device terminates (895-3) the process and, optionally, transmits advice for the subject to consult a medical professional.

If the override procedure was not triggered, or the override procedure was triggered and the subject's response indicated that a medical professional recommended they take a dihydropyridine-type calcium channel blocker pharmaceutical composition (e.g., in view of the underlying risk factor triggering the override procedure), the device proceeds with the re-qualification process, prompting (840) the subject to confirm their answers. If the user confirms their answers, the device transmits (845) a drug facts label for the dihydropyridine-type calcium channel blocker pharmaceutical composition and prompts the user to read the drug facts label. If the subject confirms they have read the drug facts label, the device proceeds to authorize purchase of the dihydropyridine-type calcium channel blocker pharmaceutical composition Specific Embodiments In one aspect, the disclosure provides methods, software, and computer systems for qualifying a human subject for over-the-counter delivery of a dihydropyridine-type calcium channel blocker pharmaceutical composition to lower blood pressure, e.g., treating or preventing heart disease. In one embodiment, a computer system (e.g., computer system 250 in FIG. 2) includes instructions for conducting a survey of the subject (e.g., survey module 204 in FIG. 2) to obtain information about the subject necessary to run against at least two series of filters (e.g., first filter category class 214 in FIG. 2 and second filter category class 220 in FIG. 2). The computer system also includes instructions for running the survey results against the filters. Filters 216 in the first series of filters prevent authorization for delivery of the OTC dihydropyridine-type calcium channel blocker where the subject's survey results identify a contraindication for the OTC dihydropyridine-type calcium channel blocker. Filters 222 in the second series of filters generate a warning 226 where the subject's survey results identify a risk factor for the OTC dihydropyridine-type calcium channel blocker. In some embodiments, the warning 226 includes a prompt requiring the subject to confirm they have discussed the risk factor with a physician in order to proceed with qualification for the OTC dihydropyridine-type calcium channel blocker.

In one aspect, the disclosure provides methods, software, and computer systems for qualifying a human subject for a re-order for over-the-counter delivery of a dihydropyridine-type calcium channel blocker pharmaceutical composition to lower blood pressure, e.g., treating or preventing heart disease. In one embodiment, a computer system includes instructions, responsive to receiving a re-order request from the subject for the dihydropyridine-type calcium channel blocker pharmaceutical composition, performing a re-fulfillment procedure comprising, for conducting a second survey of the subject to obtain survey results for qualifying the subject for the re-order, e.g., associated with at least two series of filters (e.g., a third series of filters of a first category class 214-2 in FIG. 2 and fourth series of filters of a second category class 220-2 in FIG. 2). The computer system also includes instructions for running the survey results against the filters. Filters 216 in the third series of filters prevent authorization for delivery of the OTC dihydropyridine-type calcium channel blocker where the subject's survey results identify a contraindication for the OTC dihydropyridine-type calcium channel blocker. Filters 222 in the fourth series of filters generate a warning 226 where the subject's survey results identify a risk factor for the OTC dihydropyridine-type calcium channel blocker. In some embodiments, the warning 226 includes a prompt requiring the subject to confirm they have discussed the risk factor with a physician in order to proceed with qualification for the OTC dihydropyridine-type calcium channel blocker.

The computer system includes instructions for proceeding with a re-fulfillment process only when no filters in the third series of filters was fired and the subject acknowledged each warning associated with each filter in the fourth plurality of filters that was fired. The computer system also includes instructions for storing an indication in a subject profile of a re-order for the dihydropyridine-type calcium channel blocker pharmaceutical composition The computer system also includes instructions for communicating an over-thecounter drug facts label 230 for the dihydropyridine-type calcium channel blocker pharmaceutical composition to the subject and, upon confirmation that the over-the-counter drug facts label has been received and read, authorizing provision of the OTC dihydropyridine-type calcium channel blocker pharmaceutical composition to the subject.

In one aspect, the disclosure provides a computer system for qualifying a human subject for over-the-counter delivery of a dihydropyridine-type calcium channel blocker pharmaceutical composition to lower blood pressure. The computer system comprising one or more processors and a memory, the memory comprising non-transitory instructions which, when executed by the one or more processor, perform a method for qualifying a human subject for over-the-counter delivery of the dihydropyridine-type calcium channel blocker pharmaceutical composition. The method includes conducting a first survey of the subject thereby obtaining a first plurality of survey results necessary to run against a first plurality of filters of a first category class and a second plurality of filters of a second category class. The method then includes running all or a portion of the first plurality of survey results against a first plurality of filters of a first category class, wherein, when a respective filter in the first plurality of filters is fired, the subject is deemed not qualified for delivery of the dihydropyridine-type calcium channel blocker pharmaceutical composition and the method is terminated without delivery of the dihydropyridine-type calcium channel blocker pharmaceutical composition to the subject. The method then includes running all or a portion of the first plurality of survey results against a second plurality of filters of a second category class, wherein, when a respective filter in the second plurality of filters is fired, the subject is provided with a warning corresponding to the respective filter. The method also includes obtaining acknowledgment from the subject for the warning issued to the subject by any filter in the second plurality of filters. The method also includes proceeding with a fulfillment process when no filter in the first plurality of filters has been fired and the subject has acknowledged each warning associated with each filter in the second plurality of filters that was fired. The fulfillment process includes: storing an indication in a subject profile of an initial order for the dihydropyridine-type calcium channel blocker pharmaceutical composition, communicating an over-the-counter drug facts label for the dihydropyridine-type calcium channel blocker pharmaceutical composition to the subject, and authorizing, upon confirmation from the subject that the over-the-counter drug facts label has been received and read, provision of the dihydropyridine-type calcium channel blocker pharmaceutical composition to the subject. In some embodiments, the authorization includes a destination associated with the subject.

In some embodiments, the first plurality of survey results includes a plurality of survey results selected from the survey results listed in Table 1. In one embodiment, the first plurality of survey results includes: whether the subject is one of (i) pregnant, (ii) breastfeeding, or (iii) planning to become pregnant, whether the subject is taking a dihydropyridine-type calcium channel blocker, a systolic blood pressure of the subject, a diastolic blood pressure of the subject, whether the subject has ever had an atherosclerotic cardiovascular event or had a heart procedure, a gender of the subject, an age of the subject, a race of the subject, whether the subject is taking any blood pressure medications, a diabetes status of the subject, a smoking status of the subject, a total cholesterol level of the subject, a high-density lipoprotein (HDL) cholesterol level of the subject, whether the subject has ever had a liver problem, and whether the subject is taking a medication that interacts with the dihydropyridine-type calcium channel blocker pharmaceutical composition.

In some embodiments, the first plurality of filters includes a plurality of filters selected from the filters listed in Table 2. In one embodiment, the first plurality of filters includes a pregnancy filter, a dihydropyridine medication filter, a blood pressure filter, an age filter, and a pooled cohort equation filter.

In some embodiments, the second plurality of filters includes a plurality of filters selected from the filters listed in Table 3. In one embodiment, the second plurality of filters includes a liver disease filter and a drug interaction filter.

In some embodiments, the first and second plurality of filters includes filters selected from the filters listed in Table 8. In some embodiments, the first plurality of filters of the first category class include a first sub-plurality of the filters listed in Table 8, for example, 2, 3, 4, 5, 6, 7, or all 8 of the filters listed in Table 8, and the second plurality of filters of the first category class include a second sub-plurality of the filters listed in Table 8, which is different from the first sub-plurality of filters, for example, 2, 3, 4, 5, 6, 7, or all 8 of the filters listed in Table 8. In some embodiments, each of the filters in the first sub-plurality of filters is different from each of the filters in the second sub-plurality of filters (e.g., no filter listed in Table 8 is included in both the first sub-plurality and the second sub-plurality of filters). In some embodiments, a system for qualifying a subject for delivery of an over-the-counter dihydropyridine-type calcium channel blocker pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 8, e.g., at least 2, 3, 4, 5, 6, 7, or all 8 of the filters listed in Table 8. In some embodiments, where a filter listed in Table 8 corresponds to a filter listed in Table 2 or Table 3, a threshold level sufficient to fire the corresponding filter listed in Table 2 or Table 3, as described in detail above, is sufficient to fire the filter listed in Table 8.

TABLE 8

Exemplary Filters

| Filter | Exemplary Criteria |
| --- | --- |
| 1b | a pregnancy filter |
| 2b | a dihydropyridine medication filter |
| 3b | a blood pressure filter |
| 4b | an age filter |
| 5b | a pooled cohort equation filter |
| 6b | a dihydropyridine allergy filter |
| 7b | a liver disease filter |
| 8b | a drug interaction filter |

In one aspect, the disclosure provides methods, software, and computer systems for qualifying a human subject for a re-order for over-the-counter delivery of a dihydropyridine-type calcium channel blocker pharmaceutical composition to lower blood pressure, e.g., treating or preventing heart disease. In one embodiment, a computer system includes instructions, responsive to receiving a re-order request from the subject for the dihydropyridine-type calcium channel blocker pharmaceutical composition, performing a re-fulfillment procedure comprising conducting a second survey of the subject thereby obtaining a second plurality of survey results necessary to run against a third plurality of filters of a first category class and a fourth plurality of filters of a second category class. The method then includes running all or a portion of the second plurality of survey results against a third plurality of filters of a first category class, wherein, when a respective filter in the third plurality of filters is fired, the subject is deemed not qualified for delivery of the dihydropyridine-type calcium channel blocker pharmaceutical composition and the method is terminated without delivery of the dihydropyridine-type calcium channel blocker pharmaceutical composition to the subject. The method then includes running all or a portion of the second plurality of survey results against a fourth plurality of filters of a second category class, wherein, when a respective filter in the fourth plurality of filters is fired, the subject is provided with a warning corresponding to the respective filter. The method also includes obtaining acknowledgment from the subject for the warning issued to the subject by any filter in the fourth plurality of filters. The method also includes proceeding with a re-fulfillment process when no filter in the third plurality of filters has been fired and the subject has acknowledged each warning associated with each filter in the fourth plurality of filters that was fired. The re-fulfillment process includes: storing an indication in a subject profile of a re-order for the dihydropyridine-type calcium channel blocker pharmaceutical composition, communicating the over-the-counter drug facts label for the dihydropyridine-type calcium channel blocker pharmaceutical composition to the subject, and authorizing, upon confirmation from the subject that the over-the-counter drug facts label has been received and read, provision of the dihydropyridine-type calcium channel blocker pharmaceutical composition to the subject.

In some embodiments, the third series of filters includes one or more filters listed in Table 5. In some embodiments, the third plurality of filters includes a pregnancy filter and a blood pressure filter.

In some embodiments, the fourth series of filters includes one or more filters listed in Table 6. In some embodiments, the fourth plurality of filters includes an atherosclerotic cardiovascular event filter, a drug interaction filter, and a liver disease filter.

In some embodiments, the third and fourth plurality of filters includes filters selected from the filters listed in Table 9. In some embodiments, the third plurality of filters of the first category class include a third sub-plurality of the filters listed in Table 9, for example, 2, 3, 4, 5, or all 6 of the filters listed in Table 9, and the fourth plurality of filters of the first category class include a fourth sub-plurality of the filters listed in Table 9, which is different from the third sub-plurality of filters, for example, 2, 3, 4, 5, or all 6 of the filters listed in Table 9. In some embodiments, each of the filters in the third sub-plurality of filters is different from each of the filters in the fourth sub-plurality of filters (e.g., no filter listed in Table 9 is included in both the first sub-plurality and the second sub-plurality of filters). In some embodiments, a system for qualifying a subject for delivery of an over-the-counter dihydropyridine-type calcium channel blocker pharmaceutical composition includes instructions for applying only one plurality of filters, e.g., only filters of a single category class of filters. In some embodiments, where the method, system, or software applies a single plurality of filters, the plurality of filters includes a plurality of filters selected from the filters listed in Table 9, e.g., at least 2, 3, 4, 5, or all 6 of the filters listed in Table 9. In some embodiments, where a filter listed in Table 9 corresponds to a filter listed in Table 2, Table 3, Table 5, or Table 6, a threshold level sufficient to fire the corresponding filter listed in Table 2, Table 3, Table 5, or Table 6, as described in detail above, is sufficient to fire the filter listed in Table 9.

TABLE 9

Exemplary Filters

| Filter | Exemplary Criteria |
| --- | --- |
| 1b | a pregnancy filter |
| 2b | a blood pressure filter |
| 3b | an atherosclerotic cardiovascular event filter |
| 4b | a drug interaction filter |
| 5b | a liver disease filter |
| 6b | a side-effect filter |

In one aspect, the present disclosure provides a computer system for qualifying a human subject for over-the-counter delivery of a dihydropyridine-type calcium channel blocker pharmaceutical composition for lowering blood pressure, the computer system comprising one or more processors and a memory, the memory comprising non-transitory instructions which, when executed by the one or more processor, perform a method comprising: a) conducting a first survey of the subject thereby obtaining a first plurality of survey results, wherein the first plurality of survey results comprises: whether the subject is one of (i) pregnant, (ii) breastfeeding, or (iii) planning to become pregnant, whether the subject is taking a dihydropyridine-type calcium channel blocker, a systolic blood pressure of the subject, a diastolic blood pressure of the subject, whether the subject has ever had an atherosclerotic cardiovascular event or had a heart procedure, a gender of the subject, an age of the subject, a race of the subject, whether the subject is taking any blood pressure medications, a diabetes status of the subject, a smoking status of the subject, a total cholesterol level of the subject, a high-density lipoprotein (HDL) cholesterol level of the subject, whether the subject has ever had a liver problem, and whether the subject is taking a medication that interacts with the dihydropyridine-type calcium channel blocker pharmaceutical composition; b) running all or a portion of the first plurality of survey results against a first plurality of filters of a first category class, wherein, when a respective filter in the first plurality of filters is fired, the subject is deemed not qualified for delivery of the dihydropyridine-type calcium channel blocker pharmaceutical composition and the method is terminated without delivery of the dihydropyridine-type calcium channel blocker pharmaceutical composition to the subject, wherein the first plurality of filters comprises: a first pregnancy filter that is fired at least when the first plurality of survey results indicates that the subject is pregnant or the subject is breastfeeding, a dihydropyridine medication filter that is fired at least when the first plurality of survey results indicates that the subject is taking a dihydropyridine-type calcium channel blocker, a first blood pressure filter that is fired at least when the first plurality of survey results indicates the subject has normal blood pressure or the subject has hypertension stage 2, an age filter, and a pooled cohort equation filter that incorporates the gender of the subject, the age of the subject, the race of the subject, the blood pressure medication status of the subject, the diabetes status of the subject, the smoking status of the subject, the total cholesterol level of the subject, the HDL cholesterol level of the subject, and the systolic blood pressure of the subject to derive a risk for atherosclerotic cardiovascular disease; c) running all or a portion of the first plurality of survey results against a second plurality of filters of a second category class, wherein, when a respective filter in the second plurality of filters is fired, the subject is provided with a warning corresponding to the respective filter, and wherein the second plurality of filters comprises: a first liver disease filter that is fired at least when the first plurality of survey results indicates that the subject has had a liver problem, and a first drug interaction filter that is fired at least when the first plurality of survey results indicates that the subject is taking a medication that interacts with the dihydropyridine-type calcium channel blocker pharmaceutical composition; d) obtaining acknowledgment from the subject for the warning issued to the subject by any filter in the second plurality of filters; and e) proceeding with a fulfillment process when (i) no filter in the first plurality of filters has been fired and (ii) the subject has acknowledged each warning associated with each filter in the second plurality of filters that was fired, wherein the fulfillment process comprises: storing an indication in a subject profile of an initial order for the dihydropyridine-type calcium channel blocker pharmaceutical composition, communicating an over-the-counter drug facts label for the dihydropyridine-type calcium channel blocker pharmaceutical composition to the subject, and authorizing, upon confirmation from the subject that the over-the-counter drug facts label has been received and read, provision of the dihydropyridine-type calcium channel blocker pharmaceutical composition to the subject.

In some embodiments of the aspects disclosed above, the dihydropyridine-type calcium channel blocker pharmaceutical composition has the structure:

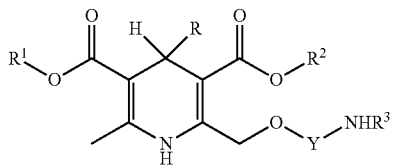

where: Y is —(CH$_2$)$_2$—, —(CH$_2$)$_3$—, —CH$_2$CH(CH$_3$)—, or —CH$_2$C(CH$_3$)$_2$—; R is aryl; R$^1$ and R$^2$ are each independently C$_1$-C$_4$ alkyl or 2-methoxyethyl; and R$^3$ is hydrogen, C$_1$-C$_4$ alkyl, 2-(C$_1$-C$_4$ alkoxy)ethyl, cyclopropylmethyl, benzyl, or —(CH$_2$)$_m$COR$_4$ where m is 1, 2 or 3 and R$^4$ is hydroxy, C$_1$-C$_4$ alkoxy or —NR$^5$R$^6$ where R$^5$ and R$^6$ are each independently hydrogen or C$_1$-C$_4$ alkyl; wherein aryl is phenyl; phenyl substituted by one or two of nitro, halo, C$_1$-C$_4$ alkyl, C$_1$-C$_4$ alkoxy, hydroxy, trifluoromethyl or cyano; 1-naphthyl; or 2-naphthyl.

In some embodiments of the aspects disclosed above, the dihydropyridine-type calcium channel blocker pharmaceutical composition includes amlodipine or a pharmaceutically acceptable salt thereof.

In some embodiments of the aspects disclosed above, the dihydropyridine-type calcium channel blocker pharmaceutical composition includes amlodipine besylate.

In some embodiments of the aspects disclosed above, upon confirmation from the subject that the over the counter drug facts label has been received and read, the subject is authorized for provision of a dosage of from 1 mg to 10 mg of the dihydropyridine-type calcium channel blocker pharmaceutical no more than once per day.

In some embodiments of the aspects disclosed above, upon confirmation from the subject that the over the counter drug facts label has been received and read, the subject is authorized for provision of a dosage of from 2.5 mg to 5 mg of the dihydropyridine-type calcium channel blocker pharmaceutical no more than once per day.

In some embodiments of the aspects disclosed above, the dihydropyridine-type calcium channel blocker pharmaceutical composition includes a composition selected from the group consisting of isradipine, nifedipine, and nisoldipine.

In some embodiments of the aspects disclosed above, the first pregnancy filter is also fired when the first plurality of survey results indicates that the subject is planning to become pregnant.

In some embodiments of the aspects disclosed above, the dihydropyridine medication filter is fired when the first plurality of survey results indicates that the subject is taking amlodipine, isradipine, nisoldipine, or nifedipine.

In some embodiments of the aspects disclosed above, the first blood pressure filter is fired when the first plurality of survey results indicates that: A) the systolic blood pressure of the subject is greater than a ceiling systolic pressure; B) the diastolic blood pressure of the subject is greater than a ceiling diastolic pressure; or C) the systolic blood pressure of the subject is less than a floor systolic pressure and the diastolic blood pressure of the subject is less than a floor diastolic pressure. In some embodiments of the aspects disclosed above, the ceiling systolic pressure is 139 mm Hg; the ceiling diastolic pressure is 89 mm Hg; the floor systolic pressure is 130 mm Hg; and the floor diastolic pressure is 80 mm Hg.

In some embodiments of the aspects disclosed above, when the first plurality of survey results indicate that the subject has elevated blood pressure but is not hypertensive, the method includes: firing the first blood pressure filter; and transmitting, to the subject, advice to manage their blood pressure by eating healthy and exercising.

In some embodiments of the aspects disclosed above, when the first plurality of survey results indicate that the subject has hypertension stage two, the method includes: firing the first blood pressure filter; and transmitting, to the subject, advice to visit a doctor to discuss taking a prescription-strength blood pressure medication.

In some embodiments of the aspects disclosed above, when the first plurality of survey results indicate that the subject is in hypertension crisis, the method includes: firing the first blood pressure filter; and transmitting, to the subject, advice to seek emergency medical attention.

In some embodiments of the aspects disclosed above, the age filter is fired when the first plurality of survey results indicates that the subject is less than eighteen years old.

In some embodiments of the aspects disclosed above, the pooled cohort equation filter is fired when the first plurality of survey results indicates: A) the subject is younger than forty years old; or B) the subject has a 10-year risk for atherosclerotic cardiovascular disease, as determined using the pooled cohort equation, that is less than 10%.

In some embodiments of the aspects disclosed above, the pooled cohort equation is implemented as a multivariable Cox proportional hazard regression.

In some embodiments of the aspects disclosed above, when the first plurality of survey results indicate that the subject is at least 80 years old, that the subject has had an atherosclerotic cardiovascular event, or that the subject has had a heart procedure, the method includes bypassing the pooled cohort equation filter.

In some embodiments of the aspects disclosed above, the drug interaction filter is fired when the first plurality of survey results indicates that the subject is taking a medication selected from the group consisting of simvastatin, cyclosporine, tacrolimus, sildenafil, and a CYP3A inhibitor.

In some embodiments of the aspects disclosed above, the first plurality of survey results further comprises whether the subject is allergic to the dihydropyridine-type calcium channel blocker pharmaceutical composition, and the first plurality of filters includes an adverse reaction filter that is fired when the first plurality of survey results indicates that the subject is allergic to the dihydropyridine-type calcium channel blocker pharmaceutical composition.

In some embodiments of the aspects disclosed above, the warning corresponding to a respective filter in the second plurality of filters comprises a prompt for the subject to indicate whether they have discussed the risk factor underlying the respective filter in the second plurality of filters that was fired with a health care provider; and acknowledgement is obtained from the subject when the subject indicates that they have discussed the risk factor underlying the respective filter in the second plurality of filters that was fired with a health care provider.

In some embodiments of the aspects disclosed above, the fulfillment process further comprises: storing a destination associated with the subject in the subject profile.

In some embodiments of the aspects disclosed above, the fulfillment process further comprises: coordinating shipping of the dihydropyridine-type calcium channel blocker pharmaceutical composition to a physical address associated with the subject.

In some embodiments of the aspects disclosed above, the method further comprises: f) responsive to receiving a re-order request from the subject for the dihydropyridine-type calcium channel blocker pharmaceutical composition, performing a re-fulfillment procedure comprising: (i) conducting a second survey of the subject thereby obtaining a second plurality of survey results, wherein the second plurality of survey results comprises: whether the subject is one of (i) pregnant, (ii) breastfeeding, or (iii) planning to become pregnant, whether the subject has experienced an atherosclerotic cardiovascular event or had a heart procedure since receiving their last provision of the dihydropyridine-type calcium channel blocker pharmaceutical composition, whether the subject has started taking a medication that interacts with the dihydropyridine-type calcium channel blocker pharmaceutical composition since receiving their last provision of the dihydropyridine-type calcium channel blocker pharmaceutical composition, and whether the subject has developed a liver problem since receiving their last provision of the dihydropyridine-type calcium channel blocker pharmaceutical composition; (ii) running all or a portion of the second plurality of survey results against a third plurality of filters of the first category class, wherein, when a respective filter in the third plurality of filters is fired, the subject is deemed not qualified for the dihydropyridine-type calcium channel blocker pharmaceutical composition and the re-fulfillment process is terminated without delivery of the dihydropyridine-type calcium channel blocker pharmaceutical composition to the subject, wherein the third plurality of filters comprise: a second pregnancy filter that is fired at least when the second plurality of survey results indicates that the subject is pregnant or the subject is breastfeeding; and (iii) running all or a portion of the second plurality of survey results against a fourth plurality of filters of the second category class, wherein, when a respective filter in the fourth plurality of filters is fired, the subject is provided with a warning corresponding to the respective filter, and wherein the fourth plurality of filters comprises: an atherosclerotic cardiovascular event filter that is fired at least when the second plurality of survey results indicates that the subject has experienced an atherosclerotic cardiovascular event or the subject has had a heart procedure since receiving their last provision of the dihydropyridine-type calcium channel blocker pharmaceutical composition, a second drug interaction filter that is fired at least when the second plurality of survey results indicates that the subject has started taking a medication that interacts with the dihydropyridine-type calcium channel blocker pharmaceutical composition since receiving their last provision of the dihydropyridine-type calcium channel blocker pharmaceutical composition, and a second liver disease filter that is fired at least when the second plurality of survey results indicates that the subject has developed symptoms of liver disease since receiving their last provision of the dihydropyridine-type calcium channel blocker pharmaceutical composition; (iv) obtaining acknowledgment from the subject for the warning issued to the subject by any filter in the fourth plurality of filters; (v) proceeding with the re-fulfillment process when (a) the re-fulfillment process is not already terminated by the firing of a filter in the third plurality of filters and (b) the subject has acknowledged each warning associated with each filter in the fourth plurality of filters that was fired, wherein the re-fulfillment process further comprises: storing an indication in the subject profile of a re-order for the dihydropyridine-type calcium channel blocker pharmaceutical composition, communicating the over-the-counter drug facts label for the dihydropyridine-type calcium channel blocker pharmaceutical composition to the subject, and authorizing, upon confirmation from the subject that the over-the-counter drug facts label has been received and read, a re-order provision of the dihydropyridine-type calcium channel blocker pharmaceutical composition to the subject.

In some embodiments of the aspects disclosed above, the re-fulfillment procedure further comprises, when the subject profile for the subject does not include a recent blood pressure for the subject: obtaining, in the second plurality of survey results, a blood pressure status of the subject; and including, in the third plurality of filters of the first category class, a second blood pressure filter that is fired at least when the second plurality of survey results indicates that the subject has hypertension.

In some embodiments of the aspects disclosed above, the re-fulfillment procedure further comprises: obtaining, in the second plurality of survey results, a blood pressure status of the subject; and including, in the third plurality of filters of the first category class, a second blood pressure filter that is fired at least when the second plurality of survey results indicates that the subject has hypertension.

In some embodiments of the aspects disclosed above, the second blood pressure filter is fired when the second plurality of survey results indicates that: A) the systolic blood pressure of the subject is above 130 mm Hg, or B) the diastolic blood pressure of the subject is above 80 mm Hg.

In some embodiments of the aspects disclosed above, when the second plurality of survey results indicates that the subject has hypertension, the method includes: firing the second blood pressure filter; and transmitting, to the subject, advice to visit a doctor to discuss taking a prescription-strength blood pressure medication.

In some embodiments of the aspects disclosed above, the second plurality of survey results further comprises whether the subject has developed a side effect associated with the dihydropyridine-type calcium channel blocker pharmaceutical composition since receiving their last provision of the dihydropyridine-type calcium channel blocker pharmaceutical composition, and the fourth plurality of filters further comprises a side effect filter that is fired at least when the second plurality of survey results indicates that the subject has developed, since receiving their last provision of the dihydropyridine-type calcium channel blocker pharmaceutical composition, a side effect selected from the group consisting of swelling of the legs, swelling of the ankles, tiredness, extreme sleepiness, stomach pain, nausea, dizziness, flushing, arrhythmia, heart palpitations, muscle rigidity, tremors, and abnormal muscle movement.

In some embodiments of the aspects disclosed above, the re-fulfillment process further comprises, when a respective filter in the third plurality of filters or fourth plurality of filters is fired, storing a record associated with the firing of the respective filter in an adverse event profile comprising records of filter firing events associated with a plurality of subjects.

In some embodiments of the aspects disclosed above, the lowering blood pressure is to treat or prevent a heart disease.

In one aspect, the disclosure provides a method for lowering blood pressure in a subject in need thereof, the method comprising: administering a (e.g., low-dose) dihydropyridine-type calcium channel blocker pharmaceutical composition to a subject qualified for over-the-counter access to the dihydropyridine-type calcium channel blocker pharmaceutical composition. In some embodiments, the subject is qualified for the over-the-counter access to the dihydropyridine-type calcium channel blocker pharmaceutical composition using a method, system, or computer readable medium disclosed herein.

In some embodiments, the dihydropyridine-type calcium channel blocker pharmaceutical composition comprises 3-O-ethyl 5-O-methyl 2-(2-aminoethoxymethyl)-4-(2-chlorophenyl)-6-methyl-1,4-dihydropyridine-3,5-dicarboxylate or a pharmaceutically acceptable salt thereof.

In some embodiments of the aspects disclosed above, the dihydropyridine-type calcium channel blocker pharmaceutical composition (e.g., an active ingredient of the composition) has the structure:

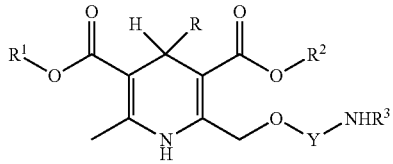

where: Y is —(CH$_2$)$_2$—, —(CH$_2$)$_3$—, —CH$_2$CH(CH$_3$)—, or —CH$_2$C(CH$_3$)$_2$—; R is aryl; R$^1$ and R$^2$ are each independently C$_1$-C$_4$ alkyl or 2-methoxyethyl; and R$^3$ is hydrogen, C$_1$-C$_4$ alkyl, 2-(C$_1$-C$_4$ alkoxy)ethyl, cyclopropylmethyl, benzyl, or —(CH$_2$)$_m$COR$_4$ where m is 1, 2 or 3 and R$^4$ is hydroxy, C$_1$-C$_4$ alkoxy or —NR$^5$R$^6$ where R$^5$ and R$^6$ are each independently hydrogen or C$_1$-C$_4$ alkyl; wherein aryl is phenyl; phenyl substituted by one or two of nitro, halo, C$_1$-C$_4$ alkyl, C$_1$-C$_4$ alkoxy, hydroxy, trifluoromethyl or cyano; 1-naphthyl; or 2-naphthyl.

In some embodiments of the aspects disclosed above, the dihydropyridine-type calcium channel blocker pharmaceutical composition includes amlodipine or a pharmaceutically acceptable salt thereof.

In some embodiments of the aspects disclosed above, the dihydropyridine-type calcium channel blocker pharmaceutical composition includes amlodipine besylate.

In some embodiments of the aspects disclosed above, upon confirmation from the subject that the over the counter drug facts label has been received and read, the subject is authorized for provision of a dosage of from 1 mg to 10 mg of amlodipine besylate per day.

In some embodiments of the aspects disclosed above, upon confirmation from the subject that the over the counter drug facts label has been received and read, the subject is authorized for provision of a dosage of from 2.5 mg to 5 mg of amlodipine per day.

In some embodiments of the aspects disclosed above, upon confirmation from the subject that the over the counter drug facts label has been received and read, the subject is authorized for provision of a dosage of 5 mg of amlodipine besylate per day.

In some embodiments of the aspects disclosed above, the dihydropyridine-type calcium channel blocker pharmaceutical composition includes a composition selected from the group consisting of isradipine, nifedipine, and nisoldipine.

In some embodiments of the aspects disclosed above, upon confirmation from the subject that the over the counter drug facts label has been received and read, the subject is authorized for provision of a dosage of from 15 mg to 90 mg per day of nifedipine. In some embodiments, the dosage of nifedipine is of from 30 mg to 60 mg per day. In some embodiments, the dosage of nifedipine is 30 mg per day. In some embodiments, the dosage of nifedipine is 60 mg per day.

In some embodiments of the aspects disclosed above, upon confirmation from the subject that the over the counter drug facts label has been received and read, the subject is authorized for provision of a dosage of from 1 mg to 20 mg per day of isradipine. In some embodiments, the dosage of isradipine is from 5 mg to 10 mg per day. In some embodiments, the dosage of isradipine is 5 mg per day. In some embodiments, the dosage of isradipine is 10 mg per day.

In some embodiments of the aspects disclosed above, upon confirmation from the subject that the over the counter drug facts label has been received and read, the subject is authorized for provision of a dosage of from 8.5 mg to 17 mg of nisoldipine per day. In some embodiments, the dosage of nisoldipine is 8.5 mg per day. In some embodiments, the dosage of nisoldipine is 17 mg per day.

In some embodiments, the disclosure provides methods for lowering blood pressure with an over the counter dihydropyridine-type calcium channel blocker pharmaceutical composition. The method includes providing a first survey for obtaining a first information set from the human, via a computer system having a processor programed to perform the first survey, where the first information set includes information about the human that relates to potential risk factors and contraindications for the dihydropyridine-type calcium channel blocker pharmaceutical composition, as described herein. The method also includes applying an algorithm to the first information set, via a computer system having a processor programed to perform the algorithm. The algorithm runs all or a portion of the first information set against a first plurality of filters, where the human is deemed not qualified for a dihydropyridine-type calcium channel blocker treatment for lowering blood pressure when a respective filter in the first plurality of filters is fired and the method is terminated without authorizing provision of the dihydropyridine-type calcium channel blocker pharmaceutical composition to the human, where the first plurality of filters includes filters related to contraindications of the dihydropyridine-type calcium channel blocker pharmaceutical composition as described herein. The algorithm also runs all or a portion of the first information set against a second plurality of filters, where, when a respective filter in the second plurality of filters is fired, the human is provided with a warning corresponding to the respective filter, and where the second plurality of filters includes filters related to risk factors for the dihydropyridine-type calcium channel blocker pharmaceutical composition as described herein. The algorithm also obtains acknowledgment from the human of the risk factor associated with each warning issued to the human by any filter in the second plurality of filters. In some embodiments, the acknowledgement includes confirmation that the human has discussed the risk factor with a physician. The algorithm proceeds with a fulfillment process when (a) no filter in the first plurality of filters has been fired and (b) the human has acknowledged each warning associated with each filter in the second plurality of filters that was fired. The fulfillment process includes storing an indication in a subject profile of an initial order for the dihydropyridine-type calcium channel blocker pharmaceutical composition, communicating an over the counter drug facts label for the dihydropyridine-type calcium channel blocker pharmaceutical composition to the human, and authorizing, upon confirmation from the subject that the over the counter drug facts label has been received and read, provision of the dihydropyridine-type calcium channel blocker pharmaceutical composition to the human, where the authorization includes a destination associated with the subject. In some embodiments, the method also includes treating the human to lower the blood pressure of the human, upon authorization of the provision e.g., by providing access to the dihydropyridine-type calcium channel blocker pharmaceutical composition to the human and/or by administering the dihydropyridine-type calcium channel blocker pharmaceutical composition to lower blood pressure in the human.

Examples

Example 1: A computer system is configured for qualifying a subject for over-the-counter delivery of an amlodipine pharmaceutical composition (e.g., (RS)-3-ethyl 5-methyl 2-[(2-aminoethoxy)methyl]-4-(2-chlorophenyl)-6-methyl-1,4-dihydropyridine-3,5-dicarboxylate) to treat or prevent heart disease (e.g., by lowering blood pressure). The computer system includes instructions for conducting a survey of the subject. The survey is utilized to obtain one or more results of: whether the subject is one of pregnant, breastfeeding, or planning to become pregnant, whether the subject is taking a dihydropyridine-type calcium channel blocker including but not limited to amlodipine, nifedipine, and/or isradipine, a systolic blood pressure of the subject, a diastolic blood pressure of the subject, whether the subject has ever had an atherosclerotic cardiovascular event (e.g., heart problems) or had a heart procedure, a gender of the subject, an age of the subject (e.g., if the subject is greater than or equal to eighteen years old), a race of the subject, whether the subject is taking any blood pressure medications, a diabetes status of the subject, a smoking status of the subject, a total cholesterol level of the subject, a high-density lipoprotein (HDL) cholesterol level of the subject, whether the subject has ever had a liver problem, and whether the subject is taking a medication that interacts with the amlodipine pharmaceutical composition.

The computer system runs survey results against a first series of filters that are each associated with a first filter category class. The first filter category class is configured to prevent authorization for OTC delivery of the OTC amlodipine when the subject's survey results identify a contraindication for the amlodipine. In some embodiments, the first series of filters includes one or more of a first pregnancy filter, a dihydropyridine medication filter, a first blood pressure filter, an age filter, and a pooled cohort equation filter. The pregnancy filter is configured to ensure the subject is not pregnant, breastfeeding, or planning to become pregnant. The dihydropyridine medication filter is configured to ensure the subject is not taking a medication that has a same mechanism of action as amlodipine. The first blood pressure filter is configured to ensure the subject is in a need to lower blood pressure. The age filter is configured to ensure the subject is greater than or equal to eighteen years old. Furthermore, the pooled cohort equation filter is configured to ensure the subject has a certain risk for heart disease.

The computer system runs survey results against a second series of filters that each generates a warning where the subject's survey results identify a risk factor for the OTC amlodipine. In some embodiments, the second series of filters comprises a first liver disease filter, a first drug interaction filter, and an optional adverse reaction filter. The first liver disease filter is configured to ensure the subject has not ever had a liver problem. The first drug interaction filter is configured to ensure the subject is not taking a substance that interacts with amlodipine. Substances that interact with amlodipine, and are therefore capable of firing the first drug interaction filter, include but are not limited to a statin utilized to treat cholesterol such as simvastatin, an immune system medicine such as cyclosporine and/or tacrolimus, an erectile dysfunction medication such as sildenafil, and a CYP3A inhibitor such as diltiazem, itraconazole, and clarithromycin.

The computer system then prompts the subject to acknowledge or deny having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC amlodipine in a subject profile, and communicates an over-the-counter drug facts label for the amlodipine pharmaceutical composition to the subject. Upon confirmation from the subject that they have received and read the over-the-counter drug facts label, the computer system authorizes provision of the OTC amlodipine pharmaceutical composition to the subject.

In some embodiments, the computer system includes instructions for conducting another survey of the subject responsive to a re-order request of the amlodipine pharmaceutical composition. This survey is utilized to obtain one or more results of: whether the subject is one of pregnant, breastfeeding, or planning to become pregnant, whether the subject has experienced an atherosclerotic cardiovascular event or had a heart procedure since receiving their last provision of the amlodipine pharmaceutical composition, whether the subject has started taking a medication that interacts with the amlodipine pharmaceutical composition since receiving their last provision of the amlodipine pharmaceutical composition, and whether the subject has developed a liver problem since receiving their last provision of the amlodipine pharmaceutical composition.

The computer system runs survey results against a third series of filters that are each associated with the first filter category class. In some embodiments, the third series of filters includes one or more of a second pregnancy filter. This pregnancy filter is fired at least when the second plurality of survey results indicates that the subject is pregnant or the subject is breastfeeding.

The computer system runs survey results against a fourth series of filters that each generates a warning where the subject's survey results identify a risk factor for the OTC amlodipine. In some embodiments, the fourth series of filters comprises an atherosclerotic cardiovascular event filter, a second drug interaction filter, and a second liver disease filter. The atherosclerotic cardiovascular event filter is configured to be fired at least when the survey results indicates that the subject has experienced an atherosclerotic cardiovascular event or the subject has had a heart procedure since receiving their last provision of the amlodipine pharmaceutical composition. The second drug interaction filter is configured to be fired at least when the survey results indicates that the subject has started taking a medication that interacts with the amlodipine pharmaceutical composition since receiving their last provision of the amlodipine pharmaceutical composition. The second liver disease filter is configured to be fired at least when the survey results indicates that the subject has developed symptoms of liver disease since receiving their last provision of the amlodipine pharmaceutical composition The computer system then prompts the subject to acknowledge or deny having discussed these warnings with a medical professional (e.g., their physician or healthcare provider). The computer system then proceeds with a re-fulfillment process only when none of the third series of filters was fired the subject acknowledged that they discussed each warning issued in association with the fourth series of filters that was fired.

The computer system stores an indication of a re-order of the OTC amlodipine in the subject profile, and communicates the over-the-counter drug facts label for the amlodipine pharmaceutical composition to the subject. Upon confirmation from the subject that they have received and read the over-the-counter drug facts label, the computer system authorizes provision of the OTC amlodipine pharmaceutical composition to the subject.

Example 2: A computer system is configured for qualifying a subject for over-the-counter delivery of a nisoldipine pharmaceutical composition (e.g., isobutyl methyl 2,6-dimethyl-4-(2-nitrophenyl)-1,4-dihydropyridine-3,5-dicarboxylate) to treat or prevent heart disease (e.g., by lowering blood pressure). The computer system includes instructions for conducting a survey of the subject. The survey is utilized to obtain one or more results of: whether the subject is one of pregnant, breastfeeding, or planning to become pregnant, whether the subject is taking a dihydropyridine-type calcium channel blocker including but not limited to amlodipine, nifedipine, nisoldipine, and/or isradipine, a systolic blood pressure of the subject, a diastolic blood pressure of the subject, whether the subject has ever had an atherosclerotic cardiovascular event (e.g., heart problems) or had a heart procedure, a gender of the subject, an age of the subject (e.g., if the subject is greater than or equal to eighteen years old), a race of the subject, whether the subject is taking any blood pressure medications, a diabetes status of the subject, a smoking status of the subject, a total cholesterol level of the subject, a high-density lipoprotein (HDL) cholesterol level of the subject, whether the subject has ever had a liver problem, and whether the subject is taking a medication that interacts with the nisoldipine pharmaceutical composition.

The computer system runs survey results against a first series of filters that are each associated with a first filter category class. The first filter category class is configured to prevent authorization for OTC delivery of the OTC nisoldipine when the subject's survey results identify a contraindication for the nisoldipine. In some embodiments, the first series of filters includes one or more of a first pregnancy filter, a dihydropyridine medication filter, a first blood pressure filter, an age filter, and a pooled cohort equation filter. The pregnancy filter is configured to ensure the subject is not pregnant, breastfeeding, or planning to become pregnant. The dihydropyridine medication filter is configured to ensure the subject is not taking a medication that has a same mechanism of action as nisoldipine. The first blood pressure filter is configured to ensure the subject is in a need to lower blood pressure. The age filter is configured to ensure the subject is greater than or equal to eighteen years old. Furthermore, the pooled cohort equation filter is configured to ensure the subject has a certain risk for heart disease.

The computer system runs survey results against a second series of filters that each generates a warning where the subject's survey results identify a risk factor for the OTC nisoldipine. In some embodiments, the second series of filters comprises a first liver disease filter, a first drug interaction filter, and an optional adverse reaction filter. The first liver disease filter is configured to ensure the subject has not ever had a liver problem. The first drug interaction filter is configured to ensure the subject is not taking a substance that interacts with nisoldipine.

The computer system then prompts the subject to acknowledge or deny having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC nisoldipine in a subject profile, and communicates an over-the-counter drug facts label for the nisoldipine pharmaceutical composition to the subject. Upon confirmation from the subject that they have received and read the over-the-counter drug facts label, the computer system authorizes provision of the OTC nisoldipine pharmaceutical composition to the subject.

In some embodiments, the computer system includes instructions for conducting another survey of the subject responsive to a re-order request of the nisoldipine pharmaceutical composition. This survey is utilized to obtain one or more results of: whether the subject is one of pregnant, breastfeeding, or planning to become pregnant, whether the subject has experienced an atherosclerotic cardiovascular event or had a heart procedure since receiving their last provision of the nisoldipine pharmaceutical composition, whether the subject has started taking a medication that interacts with the nisoldipine pharmaceutical composition since receiving their last provision of the nisoldipine pharmaceutical composition, and whether the subject has developed a liver problem since receiving their last provision of the nisoldipine pharmaceutical composition.

The computer system runs survey results against a third series of filters that are each associated with the first filter category class. In some embodiments, the third series of filters includes one or more of a second pregnancy filter. This pregnancy filter is fired at least when the second plurality of survey results indicates that the subject is pregnant or the subject is breastfeeding.

The computer system runs survey results against a fourth series of filters that each generates a warning where the subject's survey results identify a risk factor for the OTC nisoldipine. In some embodiments, the fourth series of filters comprises an atherosclerotic cardiovascular event filter, a second drug interaction filter, and a second liver disease filter. The atherosclerotic cardiovascular event filter is configured to be fired at least when the survey results indicates that the subject has experienced an atherosclerotic cardiovascular event or the subject has had a heart procedure since receiving their last provision of the nisoldipine pharmaceutical composition. The second drug interaction filter is configured to be fired at least when the survey results indicates that the subject has started taking a medication that interacts with the nisoldipine pharmaceutical composition since receiving their last provision of the nisoldipine pharmaceutical composition. The second liver disease filter is configured to be fired at least when the survey results indicates that the subject has developed symptoms of liver disease since receiving their last provision of the nisoldipine pharmaceutical composition The computer system then prompts the subject to acknowledge or deny having discussed these warnings with a medical professional (e.g., their physician or healthcare provider). The computer system then proceeds with a re-fulfillment process only when none of the third series of filters was fired the subject acknowledged that they discussed each warning issued in association with the fourth series of filters that was fired.

The computer system stores an indication of a re-order of the OTC nisoldipine in the subject profile, and communicates the over-the-counter drug facts label for the nisoldipine pharmaceutical composition to the subject. Upon confirmation from the subject that they have received and read the over-the-counter drug facts label, the computer system authorizes provision of the OTC nisoldipine pharmaceutical composition to the subject.

Example 3: A computer system is configured for qualifying a subject for over-the-counter delivery of an isradipine pharmaceutical composition (e.g., 3-methyl 5-propan-2-yl 4-(2,1,3-benzoxadiazol-4-yl)-2,6-dimethyl-1,4-dihydropyridine-3,5-dicarboxylate). The computer system includes instructions for conducting a survey of the subject. The survey is utilized to obtain one or more results of: whether the subject is one of pregnant, breastfeeding, or planning to become pregnant, whether the subject is taking a dihydropyridine-type calcium channel blocker including but not limited to amlodipine, nifedipine, and/or isradipine, a systolic blood pressure of the subject, a diastolic blood pressure of the subject, whether the subject has ever had an atherosclerotic cardiovascular event (e.g., heart problems) or had a heart procedure, a gender of the subject, an age of the subject (e.g., if the subject is greater than or equal to eighteen years old), a race of the subject, whether the subject is taking any blood pressure medications, a diabetes status of the subject, a smoking status of the subject, a total cholesterol level of the subject, a high-density lipoprotein (HDL) cholesterol level of the subject, whether the subject has ever had a liver problem, and whether the subject is taking a medication that interacts with the isradipine pharmaceutical composition.

The computer system runs survey results against a first series of filters that are each associated with a first filter category class. The first filter category class is configured to prevent authorization for OTC delivery of the OTC isradipine when the subject's survey results identify a contraindication for the isradipine. In some embodiments, the first series of filters includes one or more of a first pregnancy filter, a dihydropyridine medication filter, a first blood pressure filter, an age filter, and a pooled cohort equation filter.

The pregnancy filter is configured to ensure the subject is not pregnant, breastfeeding, or planning to become pregnant. The dihydropyridine medication filter is configured to ensure the subject is not taking a medication that has a same mechanism of action as isradipine. The first blood pressure filter is configured to ensure the subject is in a need to lower blood pressure. The age filter is configured to ensure the subject is greater than or equal to eighteen years old. Furthermore, the pooled cohort equation filter is configured to ensure the subject has a certain risk for heart disease.

The computer system runs survey results against a second series of filters that each generates a warning where the subject's survey results identify a risk factor for the OTC isradipine. In some embodiments, the second series of filters comprises a first liver disease filter, a first drug interaction filter, and an optional adverse reaction filter. The first liver disease filter is configured to ensure the subject has not ever had a liver problem. The first drug interaction filter is configured to ensure the subject is not taking a substance that interacts with isradipine.

The computer system then prompts the subject to acknowledge or deny having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC isradipine in a subject profile, and communicates an over-the-counter drug facts label for the isradipine pharmaceutical composition to the subject. Upon confirmation from the subject that they have received and read the over-the-counter drug facts label, the computer system authorizes provision of the OTC isradipine pharmaceutical composition to the subject.

In some embodiments, the computer system includes instructions for conducting another survey of the subject responsive to a re-order request of the isradipine e pharmaceutical composition. This survey is utilized to obtain one or more results of: whether the subject is one of pregnant, breastfeeding, or planning to become pregnant, whether the subject has experienced an atherosclerotic cardiovascular event or had a heart procedure since receiving their last provision of the isradipine pharmaceutical composition, whether the subject has started taking a medication that interacts with the isradipine pharmaceutical composition since receiving their last provision of the isradipine pharmaceutical composition, and whether the subject has developed a liver problem since receiving their last provision of the isradipine pharmaceutical composition.

The computer system runs survey results against a third series of filters that are each associated with the first filter category class. In some embodiments, the third series of filters includes one or more of a second pregnancy filter. This pregnancy filter is fired at least when the second plurality of survey results indicates that the subject is pregnant or the subject is breastfeeding.

The computer system runs survey results against a fourth series of filters that each generates a warning where the subject's survey results identify a risk factor for the OTC isradipine. In some embodiments, the fourth series of filters comprises an atherosclerotic cardiovascular event filter, a second drug interaction filter, and a second liver disease filter. The atherosclerotic cardiovascular event filter is configured to be fired at least when the survey results indicates that the subject has experienced an atherosclerotic cardiovascular event or the subject has had a heart procedure since receiving their last provision of the isradipine pharmaceutical composition. The second drug interaction filter is configured to be fired at least when the survey results indicates that the subject has started taking a medication that interacts with the isradipine pharmaceutical composition since receiving their last provision of the isradipine pharmaceutical composition. The second liver disease filter is configured to be fired at least when the survey results indicates that the subject has developed symptoms of liver disease since receiving their last provision of the isradipine pharmaceutical composition The computer system then prompts the subject to acknowledge or deny having discussed these warnings with a medical professional (e.g., their physician or healthcare provider). The computer system then proceeds with a re-fulfillment process only when none of the third series of filters was fired the subject acknowledged that they discussed each warning issued in association with the fourth series of filters that was fired.

The computer system stores an indication of a re-order of the OTC isradipine in the subject profile, and communicates the over-the-counter drug facts label for the isradipine e pharmaceutical composition to the subject. Upon confirmation from the subject that they have received and read the over-the-counter drug facts label, the computer system authorizes provision of the OTC isradipine pharmaceutical composition to the subject.

Example 4: A computer system is configured for qualifying a subject for over-the-counter delivery of an nifedipine pharmaceutical composition (e.g., 3,5-dimethyl 2,6-dimethyl-4-(2-nitrophenyl)-1,4-dihydropyridine-3,5-dicarboxylate) to treat or prevent heart disease (e.g., by lowering blood pressure). The computer system includes instructions for conducting a survey of the subject. The survey is utilized to obtain one or more results of: whether the subject is one of pregnant, breastfeeding, or planning to become pregnant, whether the subject is taking a dihydropyridine-type calcium channel blocker including but not limited to amlodipine, nifedipine, and/or isradipine, a systolic blood pressure of the subject, a diastolic blood pressure of the subject, whether the subject has ever had an atherosclerotic cardiovascular event (e.g., heart problems) or had a heart procedure, a gender of the subject, an age of the subject (e.g., if the subject is greater than or equal to eighteen years old), a race of the subject, whether the subject is taking any blood pressure medications, a diabetes status of the subject, a smoking status of the subject, a total cholesterol level of the subject, a high-density lipoprotein (HDL) cholesterol level of the subject, whether the subject has ever had a liver problem, and whether the subject is taking a medication that interacts with the nifedipine pharmaceutical composition.

The computer system runs survey results against a first series of filters that are each associated with a first filter category class. The first filter category class is configured to prevent authorization for OTC delivery of the OTC nifedipine when the subject's survey results identify a contraindication for the nifedipine. In some embodiments, the first series of filters includes one or more of a first pregnancy filter, a dihydropyridine medication filter, a first blood pressure filter, an age filter, and a pooled cohort equation filter. The pregnancy filter is configured to ensure the subject is not pregnant, breastfeeding, or planning to become pregnant. The dihydropyridine medication filter is configured to ensure the subject is not taking a medication that has a same mechanism of action as nifedipine. The first blood pressure filter is configured to ensure the subject is in a need to lower blood pressure. The age filter is configured to ensure the subject is greater than or equal to eighteen years old. Furthermore, the pooled cohort equation filter is configured to ensure the subject has a certain risk for heart disease.

The computer system runs survey results against a second series of filters that each generates a warning where the subject's survey results identify a risk factor for the OTC nifedipine. In some embodiments, the second series of filters comprises a first liver disease filter, a first drug interaction filter, and an optional adverse reaction filter. The first liver disease filter is configured to ensure the subject has not ever had a liver problem. The first drug interaction filter is configured to ensure the subject is not taking a substance that interacts with nifedipine.

The computer system then prompts the subject to acknowledge or deny having discussed these warnings with a medical professional (e.g., their physician or healthcare provider). The computer system then proceeds with a fulfillment process only when none of the first series of filters was fired and the subject acknowledged that they discussed each warning issued in association with the second series of filters that was fired.

The computer system stores an indication of an initial order of the OTC nifedipine in a subject profile, and communicates an over-the-counter drug facts label for the nifedipine pharmaceutical composition to the subject. Upon confirmation from the subject that they have received and read the over-the-counter drug facts label, the computer system authorizes provision of the OTC nifedipine pharmaceutical composition to the subject.

In some embodiments, the computer system includes instructions for conducting another survey of the subject responsive to a re-order request of the nifedipine pharmaceutical composition. This survey is utilized to obtain one or more results of: whether the subject is one of pregnant, breastfeeding, or planning to become pregnant, whether the subject has experienced an atherosclerotic cardiovascular event or had a heart procedure since receiving their last provision of the nifedipine pharmaceutical composition, whether the subject has started taking a medication that interacts with the nifedipine pharmaceutical composition since receiving their last provision of the nifedipine pharmaceutical composition, and whether the subject has developed a liver problem since receiving their last provision of the nifedipine pharmaceutical composition.

The computer system runs survey results against a third series of filters that are each associated with the first filter category class. In some embodiments, the third series of filters includes one or more of a second pregnancy filter. This pregnancy filter is fired at least when the second plurality of survey results indicates that the subject is pregnant or the subject is breastfeeding.

The computer system runs survey results against a fourth series of filters that each generates a warning where the subject's survey results identify a risk factor for the OTC nifedipine. In some embodiments, the fourth series of filters comprises an atherosclerotic cardiovascular event filter, a second drug interaction filter, and a second liver disease filter. The atherosclerotic cardiovascular event filter is configured to be fired at least when the survey results indicates that the subject has experienced an atherosclerotic cardiovascular event or the subject has had a heart procedure since receiving their last provision of the nifedipine pharmaceutical composition. The second drug interaction filter is configured to be fired at least when the survey results indicates that the subject has started taking a medication that interacts with the nifedipine pharmaceutical composition since receiving their last provision of the nifedipine pharmaceutical composition. The second liver disease filter is configured to be fired at least when the survey results indicates that the subject has developed symptoms of liver disease since receiving their last provision of the nifedipine pharmaceutical composition The computer system then prompts the subject to acknowledge or deny having discussed these warnings with a medical professional (e.g., their physician or healthcare provider). The computer system then proceeds with a re-fulfillment process only when none of the third series of filters was fired the subject acknowledged that they discussed each warning issued in association with the fourth series of filters that was fired.

The computer system stores an indication of a re-order of the OTC nifedipine in the subject profile, and communicates the over-the-counter drug facts label for the nifedipine pharmaceutical composition to the subject. Upon confirmation from the subject that they have received and read the over-the-counter drug facts label, the computer system authorizes provision of the OTC nifedipine pharmaceutical composition to the subject.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

Figure 5D:
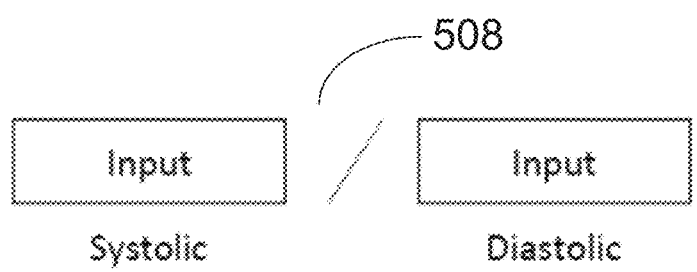

The present invention can be implemented as a computer program product that comprises a computer program mechanism embedded in a non-transitory computer readable storage medium. For instance, the computer program product could contain the program modules shown in any combination of FIGS. 1, 2, and 3 and/or described in FIG. 4 or 5. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method of managing blood pressure in a human subject who was previously qualified to receive a drug, wherein the drug is a dihydropyridine-type calcium channel blocker pharmaceutical composition, the method comprising, responsive to receiving a re-order request:
   a) obtaining an information set about the subject, via a computer system having a processor programed to obtain the information set, the information set comprising:
      whether the subject is pregnant or breastfeeding,
      whether the subject has experienced an atherosclerotic cardiovascular event or had a heart procedure since receiving their last provision of the drug,
      whether the subject has started taking a medication that interacts with the drug since receiving their last provision of the drug, and
      whether the subject has developed a liver problem since receiving their last provision of the drug;
   b) applying an algorithm to the information set, via a computer system having a processor programed to perform the algorithm, wherein the algorithm:
      i) runs all or a portion of the information set against a first set of filters of a first category class wherein, when a respective filter in the first set of filters is fired, the subject is deemed not qualified for treatment with the drug, and wherein the first set of filters comprises:
         a pregnancy filter that is fired at least when the information set indicates that the subject is pregnant or the subject is breastfeeding;
      ii) runs all or a portion of the information set against a second set of filters of a second category class wherein, when a respective filter in the second set of filters is fired, the subject is provided with a warning corresponding to the respective filter, and wherein the second set of filters comprises:
         an atherosclerotic cardiovascular event filter that is fired at least when the information set indicates that the subject has experienced an atherosclerotic cardiovascular event or the subject has had a heart procedure since receiving their last provision of the drug,
         a drug interaction filter that is fired at least when the information set indicates that the subject has started taking a medication that interacts with the drug since receiving their last provision of the drug, and
         a liver disease filter that is fired at least when the information set indicates that the subject has developed symptoms of liver disease since receiving their last provision of the drug;
      iii) obtains acknowledgment from the subject for each warning issued to the subject by any filter in the second set of filters;
      iv) proceeds with a re-fulfillment process when i) a filter in the first set of filters has not been fired and ii) the subject has acknowledged each warning associated with each filter in the second set of filters that was fired, wherein the re-fulfilment process comprises:
         storing an indication in the subject profile of a re-order for the drug,
         communicating a drug facts label for the drug, and
         authorizing, upon confirmation from the subject that the drug facts label has been received and read, a re-order provision of the drug to the subject; and
   c) administering the drug to the subject after authorization of the re-order provision, to manage blood pressure in the subject.

2. The method of claim 1, wherein, when the subject profile for the subject does not include a recent blood pressure for the subject:
   the information set further comprises a blood pressure status of the subject; and
   the first set of filters of the first category class further comprises a blood pressure filter that is fired at least when the information set indicates that the subject is hypertensive.

3. The method of claim 2, wherein the blood pressure filter is fired when the information set indicates that:

A) the systolic blood pressure of the subject is above 130 mm Hg, or

B) the diastolic blood pressure of the subject is above 80 mm Hg.

4. The method of claim 2, wherein the method further comprises, when the blood pressure filter is fired, transmitting advice to the subject to visit a doctor to discuss taking a prescription-strength blood pressure medication.

5. The method of claim 1, wherein:
the information set further comprises a blood pressure status of the subject; and
the first set of filters of the first category class further comprises a blood pressure filter that is fired at least when the information set indicates that the subject is hypertensive.

6. The method of claim 5, wherein the blood pressure filter is fired when the information set indicates that:

A) the systolic blood pressure of the subject is above 130 mm Hg, or

B) the diastolic blood pressure of the subject is above 80 mm Hg.

7. The method of claim 1, wherein:
the information set further comprises whether the subject has experienced a side effect associated with the drug since receiving their last provision of the drug, and
the second set of filters further comprises a side effect filter that is fired at least when the second plurality of survey results indicates that the subject has experienced a side effect associated with the drug.

8. The method of claim 7, wherein the side effect is selected from the group consisting of swelling of the legs, swelling of the ankles, tiredness, extreme sleepiness, stomach pain, nausea, dizziness, flushing, arrhythmia, heart palpitations, muscle rigidity, tremors, and abnormal muscle movement.

9. The method of claim 1, wherein the re-fulfillment process further comprises, when a respective filter in the first set of filters or second set of filters is fired, storing a record associated with the firing of the respective filter in an adverse event profile comprising records of filter firing events associated with a plurality of subjects.

10. The method of claim 1, wherein the administering of the drug to the subject after authorization of the re-order provision to manage blood pressure in the subject is to treat or prevent a heart disease in the subject.

11. The method of claim 1, wherein the drug comprises 3-O-ethyl 5-O-methyl 2-(2-aminoethoxymethyl)-4-(2-chlorophenyl)-6-methyl-1,4-dihydropyridine-3,5-dicarboxylate, or a pharmaceutically acceptable salt thereof, as an active ingredient.

12. The method of claim 1, wherein the drug comprises an active ingredient having the structure:

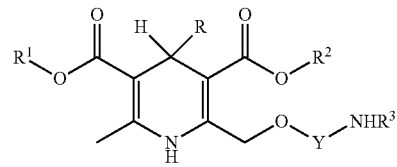

wherein:

Y is $-(CH_2)_2-$, $-(CH_2)_3-$, $-CH_2CH(CH_3)-$, or $-CH_2C(CH_3)_2-$

R is aryl;

$R^1$ and $R^2$ are each independently $C_1$-$C_4$ alkyl or 2-methoxyethyl; and $R^3$ is hydrogen, $C_1$-$C_4$ alkyl, 2—($C_1$-$C_4$ alkoxy)ethyl, cyclopropylmethyl, benzyl, or $-(CH_2)_m COR^4$ where m is 1, 2 or 3 and $R^4$ is hydroxy, $C_1$-$C_4$ alkoxy or $-NR^5R^6$ where $R^5$ and $R^6$ are each independently hydrogen or $C_1$-$C_4$ alkyl; wherein aryl is phenyl; phenyl substituted by one or two of nitro, halo, $C_1$-$C_4$ alkyl, $C_1$-$C_4$ alkoxy, hydroxy, trifluoromethyl or cyano;

1-naphthyl; or 2-naphthyl.

13. The method of claim 1, wherein the drug comprises amlodipine besylate as an active ingredient.

14. The method of claim 13, wherein the administering comprises administering to the subject the drug in the form of a dosage of from 1 mg to 10 mg per day of amlodipine besylate.

15. The method of claim 13, wherein the administering comprises administering to the subject the drug in the form of a dosage of from 2.5 mg to 5 mg per day of amlodipine besylate.

16. The method of claim 1, wherein the drug comprises an active ingredient selected from the group consisting of isradipine, nifedipine, and nisoldipine.

17. The method of claim 16, wherein the administering comprises administering to the subject the drug in the form of a dosage of from 15 mg to 60 mg of nifedipine per day.

18. The method of claim 16, wherein the administering comprises administering to the subject the drug in the form of a dosage of from 1 mg to 10 mg of isradipine per day.

19. The method of claim 16, wherein the administering comprises administering to the subject the drug in the form of a dosage of from 8.5 mg to 17 mg of nisoldipine per day.

\* \* \* \* \*